United States Patent
Kambe et al.

(10) Patent No.: US 7,256,211 B1
(45) Date of Patent: *Aug. 14, 2007

(54) 8-AZAPROSTAGLANDIN DERIVATIVES AND MEDICAL USE THEREOF

(75) Inventors: Tohru Kambe, Mishima-gun (JP); Toru Maruyama, Mishima-gun (JP); Kaoru Kobayashi, Mishima-gun (JP); Kousuke Tani, Mishima-gun (JP); Yoshihiko Nakai, Mishima-gun (JP); Toshihiko Nagase, Mishima-gun (JP); Takayuki Maruyama, Mishima-gun (JP); Kiyoto Sakata, Mishima-gun (JP); Hideyuki Yoshida, Mishima-gun (JP); Shinsei Fujimura, Mishima-gun (JP); Akio Nishiura, Mishima-gun (JP); Nobutaka Abe, Mishima-gun (JP)

(73) Assignee: ONO Pharmaceutical Co., Ltd., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/542,724

(22) PCT Filed: Jan. 20, 2004

(86) PCT No.: PCT/JP2004/000419

§ 371 (c)(1),
(2), (4) Date: Jul. 20, 2005

(87) PCT Pub. No.: WO2004/065365

PCT Pub. Date: Aug. 5, 2004

(30) Foreign Application Priority Data

Jan. 21, 2003 (JP) .............. 2003-011936
Aug. 8, 2003 (JP) .............. 2003-289954

(51) Int. Cl.
*A61K 31/40* (2006.01)
*A61K 31/426* (2006.01)
*C07D 207/12* (2006.01)
*C07D 207/36* (2006.01)

(52) U.S. Cl. ............... 514/422; 514/424; 514/369; 548/524; 548/543; 548/182; 548/201; 548/202

(58) Field of Classification Search ............... 514/369, 514/422; 548/188, 518, 527, 543
See application file for complete search history.

(56) References Cited

U.S. PATENT DOCUMENTS

| 4,177,346 | A | 12/1979 | Nelson |
| 6,552,067 | B2* | 4/2003 | Cameron et al. ............ 514/424 |
| 2003/0207925 | A1* | 11/2003 | Cameron et al. ............ 514/424 |
| 2005/0020686 | A1* | 1/2005 | Maruyama et al. ......... 514/573 |

FOREIGN PATENT DOCUMENTS

EP  1 110 949 B1  6/2001
EP  1 121 939 A2  8/2001
EP  1 132 086 A2  9/2001
JP  5-321159 A   12/1993
JP  2001-181210   7/2001
JP  2001-220357 A  8/2001
JP  2001-233792 A  8/2001
WO  WO 03/009872 A  2/2003
WO  WO 03/047417 A2  6/2003
WO  WO 03/047513 A2  6/2003
WO  WO 03/077908 A1  9/2003
WO  WO 03/077910 A1  9/2003
WO  WO 03/097596 A1  11/2003
WO  WO 03/103604 A2  12/2003

OTHER PUBLICATIONS

International Search Report dated Mar. 16, 2004.

* cited by examiner

*Primary Examiner*—Kamal A. Saeed
*Assistant Examiner*—Yong Chu
(74) *Attorney, Agent, or Firm*—Sughrue Mion, PLLC

(57) ABSTRACT

The pharmaceutical composition comprising the compound of the invention having 8-azaprostaglandin skeleton represented by formula (I)

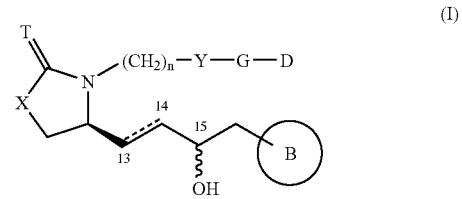

(wherein, all the symbols have the same meanings as that of the specification) a salt thereof, a solvate thereof or a cyclodextrin clathrate thereof, or a prodrug thereof and them as active ingredient have $EP_4$ agonistic action and thus are considered useful for the prevention and/or treatment of immunological diseases, asthma, neuronal cell death, arthritis, lung failure, pulmonary fibrosis, pulmonary emphysema, bronchitis, chronic obstructive pulmonary disease, liver damage, acute hepatitis, nephritis, renal insufficiency, hypertension, myocardial ischemia, systemic inflammatory response syndrome, sepsis, hemophagous syndrome, macrophage activation syndrome, Still's disease, Kawasaki disease, burn, systemic granulomatosis, ulcerative colitis, Crohn's disease, hypercytokinemia at dialysis, multiple organ failure, shock and glaucoma, etc. Furthermore, the compounds also have an action of accelerating bone formation, so it is expected to be useful for the prevention and/or treatment of diseases associated with loss in bone mass, for example, primary osteoporosis, secondary osteoporosis, bone metastasis of cancer, hypercalcemia, Paget's disease, bone loss, osteonecrosis, bone formation after bone operation, alternative treatment for bone grafting.

7 Claims, No Drawings

8-AZAPROSTAGLANDIN DERIVATIVES AND MEDICAL USE THEREOF

This is a National Stage application of PCT Application No. PCT/JP04/000419, filed Jan. 20, 2004, which claims priority from Japanese Patent Application Nos. JP 2003-11936, filed Jan. 21, 2003, and JP 2003-289954, filed Aug. 8, 2003.

TECHNICAL FIELD

The present invention relates to the compounds having 8-azaprostaglandin skeleton useful for pharmaceuticals and the pharmaceutical composition comprising them as an active ingredient.

BACKGROUND ART

Prostaglandin $E_2$ (abbreviated as $PGE_2$) has been known as a metabolite in the arachidonate cascade. It has been known that $PGE_2$ possesses cyto-protective activity, uterine contractive activity, a pain-inducing effect, a promoting effect on peristaltic movement, an awakening effect, a suppressive effect on gastric acid secretion, hypotensive activity and diuretic activity and so on.

A recent study has proved existence of various PGE subtype receptors possessing a different physical role from each other. At present, four receptor subtypes are known and they are called $EP_1$, $EP_2$, $EP_3$, and $EP_4$ (Negishi M., et al., *J. Lipid Mediators Cell Signaling*, 12, 379–391 (1995)).

Among these, it is thought that $EP_4$ subtype receptor relates to inhibition of TNF-α production and acceleration of IL-10 production. Therefore, the compounds which can bind on $EP_4$ subtype receptor are expected to be useful for the prevention and/or treatment of immunological diseases (autoimmune disease such as amyotrophic lateral sclerosis (ALS), multiple sclerosis, Sjoegren's syndrome, chronic rheumarthrosis and systemic lupus erythematosus, etc., and rejection after organ transplantation, etc.), asthma, neuronal cell death, arthritis, lung failure, pulmonary fibrosis, pulmonary emphysema, bronchitis, chronic obstructive pulmonary disease, liver damage, acute hepatitis, nephritis (acute nephritis, chronic nephritis), renal insufficiency, hypertension, myocardial ischemia, systemic inflammatory response syndrome, sepsis, hemophagous syndrome, macrophage activation syndrome, Still's disease, Kawasaki disease, burn, systemic granulomatosis, ulcerative colitis, Crohn's disease, hypercytokinemia at dialysis, multiple organ failure, shock and glaucoma, etc. It is also thought that $EP_4$ subtype receptor relates to protecting of mucosa. Therefore, the compounds which can bind on $EP_4$ subtype receptor are expected to be useful for the prevention and/or treatment of ulcer of gastrointestinal tract such as gastric ulcer and duodenal ulcer, etc. and stomatitis. It is also thought that $EP_4$ subtype receptor relates to hair growth function. Therefore, the compounds which can bind on $EP_4$ subtype receptor are expected to be useful for the prevention and/or treatment of hair-disadvantaged and alopecia. Furthermore, it is also thought that $EP_4$ subtype receptor relates to maturation of cervix. Therefore, the compounds which can bind on $EP_4$ subtype receptor are expected to be useful for the promoter of (maturation of) cervix.

Furthermore, the compounds which can bind on $EP_4$ subtype receptor also have an action of accelerating bone formation, so it is expected to be useful for the prevention and/or treatment of diseases associated with loss in bone mass, for example, 1) primary osteoporosis (e.g., primary osteoporosis followed by aging, postmenopausal primary osteoporosis, primary osteoporosis followed by ovariectomy, etc.), 2) secondary osteoporosis (e.g., glucocorticoid-induced osteoporosis, hyperthyroidism-induced osteoporosis, immobilization-induced osteoporosis, heparin-induced osteoporosis, immunosuppressive-induced osteoporosis, osteoporosis due to renal failure, inflammatory osteoporosis, osteoporosis followed by Cushing's syndrome, rheumatoid osteoporosis, etc.), 3) bone diseases such as bone metastasis of cancer, hypercalcemia, Paget's disease, bone loss (alveolar bone loss, mandibular bone loss, childhood idiopathic bone loss, etc.), osteonecrosis, etc. Besides treatment of the above diseases, the present invention also includes a pharmaceutical composition for accelerating bone formation after bone operation (e.g., bone formation after fractures, bone formation after bone grafting, bone formation after operation of artificial joint, bone formation after spinal fusion and bone formation after the other operation for bone regeneration, etc.), or promoting treatment thereof, or alternative treatment for bone grafting.

It is also thought that $EP_4$ subtype receptor relates to induction of physiological sleeping and suppression of blood platelet aggregation, so the compounds which can bind on $EP_4$ subtype receptor are expected to be useful for the prevention and/or treatment of sleep disorder and thrombosis.

The compounds which can bind on $EP_4$ subtype receptor selectively do not have inducing pain which may be caused by EP, and uterine contraction which may be caused by $EP_3$, so they are thought to be agents having no effect on the above actions.

As the EP4 agonistic compound, reported is the compound represented by formula (Ia) (cf. WO03/009872):

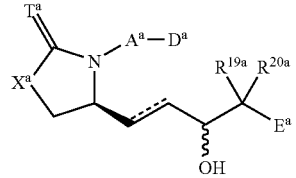

(Ia)

wherein ⋯ is a single bond or a double bond, $R^{19a}$ and $R^{20a}$ are each independently, a hydrogen atom, C1–10 alkyl or a halogen atom, $T^a$ is oxygen or sulfur, $X^a$ is —$CH_2$—, —O— or —S—, $A^a$ is $A^{1a}$ or $A^{2a}$, $A^{1a}$ is C2–8 straight-chain alkylene optionally substituted with 1–2 of C1–4 alkyl, C2–8 straight-chain alkenylene optionally substituted with 1–2 of C1–4 alkyl or C2–8 straight-chain alkynylene optionally substituted with 1–2 of C1–4 alkyl, $A^{2a}$ is -$G^{1a}$-$G^{2a}$-$G^{3a}$-, $G^{1a}$ is C1–4 straight-chain alkylene optionally substituted with 1–2 of C1–4 alkyl, C2–4 straight-chain alkenylene optionally substituted with 1–2 of C1–4 alkyl or C2–4 straight-chain alkynylene optionally substituted with 1–2 of C1–4 alkyl, $G^{2a}$ is —$Y^a$—, -(ring1$^a$)-, —$Y^a$-(ring1$^a$)-, -(ring1$^a$)-$Y^a$— or —$Y^a$-(C1–4 alkylene)-(ring1$^a$)-, $Y^a$ is —S—, —SO—, —SO$_2$—, —O— or —NR$^{1a}$—, $R^{1a}$ is a hydrogen atom, C1–10 alkyl or C2–10 acyl, $G^{3a}$ is a bond, C1–4 straight-chain alkylene optionally substituted with 1–2 of C1–4 alkyl, C2–4 straight-chain alkenylene optionally substituted with 1–2 of C1–4 alkyl or C2–4 straight-chain alkynylene optionally substituted with 1–2 of C1–4 alkyl, $D^a$ is $D^{1a}$ or $D^{2a}$, $D^{1a}$ is —COOH, —COOR$^{2a}$, tetrazol-5-yl or CONR$^{3a}$SO$_2$R$^{4a}$, $R^{2a}$ is C1–10 alkyl, phenyl, C1–10 alkyl substituted with phenyl or biphenyl, $R^{3a}$ is a hydrogen atom or C1–10 alkyl, $R^{4a}$ is C1–10 alkyl or phenyl, $D^{2a}$ is (1) —CH$_2$OH, (2) —CH$_2$OR$^{5a}$, (3) hydroxy, (4) —OR$^{5a}$, (5) formyl, (6) —CONR$^{6a}$R$^{7a}$, (7) —CONR$^{6a}$SO$_2$R$^{8a}$, (8) —CO—(NH-amino acid residue-CO)$_m$—OH, (9) —O—(CO— amino acid residue —NH)$_m$—H, (10) —COOR$^{9a}$, (11) —OCO—R$^{10a}$, (12) —COO—Z$^{1a}$—Z$^{2a}$—Z$^{3a}$, or (13)

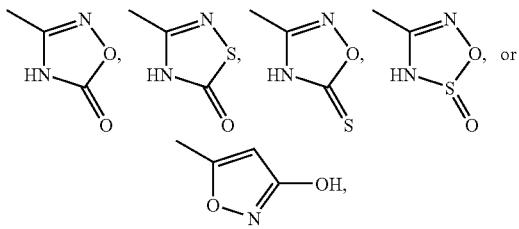

$R^{5a}$ is C1–10 alkyl, $R^{6a}$ and $R^{7a}$ are each independently, a hydrogen atom or C1–10 alkyl, $R^{8a}$ is C1–10 alkyl substituted with phenyl, $R^{9a}$ is (1) C1–10 alkyl substituted with biphenyl optionally substituted with 1–3 of C1–10 alkyl, C1–10 alkoxy or a halogen atom or (2) biphenyl substituted with 1–3 of C1–10 alkyl, C1–10 alkoxy or a halogen atom, $R^{10a}$ is phenyl or C1–10 alkyl, m is 1 or 2, $Z^{1a}$ is C1–15 alkylene, C2–15 alkenylene or C2–15 alkynylene, $Z^{2a}$ is (1) —CO—, (2) —OCO—, (3) —COO—, (4) —CONR$^{11a}$—, (5) —NR$^{12a}$CO—, (6) —O—, (7) —S—, (8) —SO—, (9) —SO$_2$—, (10) —NR$^{13a}$—, (11) —NR$^{14a}$CONR$^{15a}$—, (12) —NR$^{16a}$COO—, (13) —OCONR$^{17a}$— or (14) —OCOO—, $Z^{3a}$ is (1) a hydrogen atom, (2) C1–15 alkyl, (3) C2–15 alkenyl, (4) C2–15 alkynyl, (5) ring2$^a$ or (6) C1–10 alkyl substituted with C1–10 alkoxy, C1–10 alkylthio, C1–10 alkyl-NR$^{18a}$— or ring2$^a$, $R^{11a}$, $R^{12a}$, $R^{13a}$, $R^{14a}$, $R^{15a}$, $R^{16a}$, $R^{17a}$ and $R^{18a}$ are each independently, a hydrogen atom or C1–15 alkyl, $R^{11a}$ and $Z^{3a}$ may be taken together with the nitrogen atom to which they are attached to form 5- to 7-membered saturated monoheterocyclic ring, and said heterocyclic ring may contain other one hetero atom selected from oxygen, nitrogen and sulfur atom, $E^a$ is $E^{1a}$ or $E^{2a}$, $E^{1a}$ is C3–7 cycloalkyl or ring3$^a$, $E^{2a}$ is C3–7 cycloalkyl, ring4$^a$ or ring5$^a$, ring1$^a$ and ring5$^a$ are optionally substituted with 1–3 of $R^{21a}$ and/or $R^{22a}$, ring3$^a$ is optionally substituted with 1–2 $R^{21a}$, C3–7 cycloalkyl represented by $E^{2a}$ is substituted with one of $R^{21a}$ or $R^{22a}$, and optionally substituted with another 1–2 of $R^{21a}$ and/or $R^{22a}$, ring4$^a$ is substituted with one of $R^{22a}$, optionally substituted with another 1–2 of $R^{21a}$ and/or $R^{22a}$, and optionally substituted with a heterocyclic ring formed by $R^{11a}$, $Z^{3a}$ and the nitrogen to which $Z^{3a}$ is attached or ring2$^a$ may be substituted with $R^{23a}$, $R^{21a}$ is C1–10 alkyl, C1–10 alkoxy, a halogen atom, nitro, C1–10 alkyl substituted with 1–3 of halogen atom(s) or phenyl, $R^{22a}$ is (1) C2–10 alkenyl, (2) C2–10 alkynyl, (3) C1–10 alkylthio, (4) hydroxy, (5) —NR$^{24a}$R$^{25a}$, (6) C1–10 alkyl substituted with C1–10 alkoxy, (7) C1–10 alkyl substituted with C1–10 alkoxy substituted with 1–3 of halogen atom(s), (8) C1–10 alkyl substituted with —NR$^{24a}$R$^{25a}$, (9) ring6$^a$, (10) —O-ring7$^a$, (11) C1–10 alkyl substituted with ring7$^a$, (12) C2–10 alkenyl substituted with ring7$^a$, (13) C2–10 alkynyl substituted with ring7$^a$, (14) C1–10 alkoxy substituted with ring7$^a$, (15) C1–10 alkyl substituted with —O—ring7$^a$, (16) —COOR$^{26a}$ or (17) C1–10 alkoxy substituted with 1–3 of halogen atom(s), $R^{24a}$, $R^{25a}$ and $R^{26a}$ are each independently, a hydrogen atom or C1–10 alkyl, $R^{23a}$ is (1) C1–15 alkyl, (2) C2–15 alkenyl, (3) C2–15 alkynyl or (4) C1–10 alkyl substituted with C1–10 alkoxy, C1–10 alkylthio or C1–10 alkyl-NR$^{27a}$-, $R^{27a}$ is a hydrogen atom or C1–10 alkyl, ring1$^a$, ring2$^a$, ring5$^a$, ring6$^a$ and ring7$^a$ are (1) C3–15 mono-, bi- or tri-carbocyclic aryl which may be partially or fully saturated or (2) 3- to 15-membered mono-, bi- or tri-heterocyclic aryl containing 1 to 4 hetero atom(s) selected from oxygen, nitrogen and sulfur atom(s) which may be partially or fully saturated, ring3$^a$ and ring4$^a$ are thienyl, phenyl or furyl, ring6$^a$ and ring7$^a$ may be substituted with 1–3 of $R^{28a}$, $R^{28a}$ is (1) C1–10 alkyl, (2) C2–10 alkenyl, (3) C2–10 alkynyl, (4) C1–10 alkoxy, (5) C1–10 alkyl substituted with C1–10 alkoxy, (6) halogen atom, (7) hydroxy, (8) C1–10 alkyl substituted with 1–3 of halogen atom(s) or (9) C1–10 alkyl substituted with C1–10 alkoxy substituted with 1–3 of halogen atom(s), and wherein (1) when $T^a$ is an oxygen atom, $X^a$ is CH$_2$—, $A^a$ is $A^{1a}$, and $D^a$ is $D^{1a}$, then $E^a$ is $E^{2a}$, (2) ring5$^a$ is not C3–7 cycloalkyl, phenyl, thienyl nor furyl, (3) ring6$^a$ is phenyl, then phenyl have at least one $R^{28a}$.

The present invention is the selective invention in the WO03/009872 and the compounds in the present invention are included within the compound represented by formula (Ia).

In addition, the specification of U.S. Pat. No. 4,177,346 discloses the compound represented by formula (A)

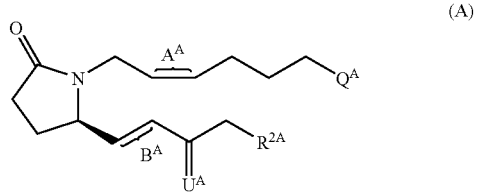

wherein $Q^A$ is selected from the group consisting of —COOR$^{3A}$, tetrazol-5-yl and —CONHR$^{4A}$;

$A^A$ is a single bond or a cis-double bond;

$B^A$ is a single bond or a trans-double bond;

$U^A$ is

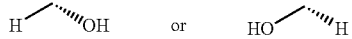

$R^{2A}$ is selected from the group consisting of α-thienyl, phenyl, phenoxy, mono-substituted phenyl and mono-substituted phenoxy, and said substituent is selected from the group consisting of chlorine, fluorine, phenyl, methoxy, trifluoromethyl and C1–3 alkyl;

$R^{3A}$ is selected from the group consisting of hydrogen, C1–5 alkyl, phenyl and p-biphenyl;

$R^{4A}$ is selected from the group consisting of —$COR^{5A}$ and —$SO_2R^{5A}$;

$R^{5A}$ is selected from the group consisting of phenyl and C1–5 alkyl, and a C5 epimer thereof, the salt of alkali metal and alkaline earth metals and ammonium salt of the compound which have carboxylate or tetrazol-5-yl.

And in the specification of JP-A-2001-181210, it is disclosed that the selective $EP_4$ receptor agonist represented by above-mentioned formula (A) is useful for the treatment of osteoporosis.

And the specification of United Kingdom Patent No. 1,553,595 discloses the pyrrolidone derivatives represented by formula (B)

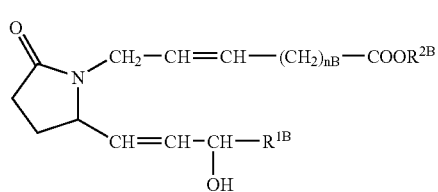

wherein $R^{1B}$ is a straight- or branched-chain, saturated or unsaturated, aliphatic hydrocarbon radical having up to 10 carbon atoms, or a cycloaliphatic hydrocarbon radical having 3 to 7 carbon atoms, which radicals may be unsubstituted or substituted with one or more of the following: e) a cycloalkyl group of 3 to 7 carbon atoms, f) a phenyl, thienyl or furyl group which may carry one or two substituents selected from optionally halogenated alkyl group of 1 to 3 carbon atoms, halogen atoms and alkoxy group of 1 to 4 carbon atoms, $R^{2B}$ is a straight- or branched-chain, saturated or unsaturated, aliphatic or cycloaliphatic hydrocarbon radical having up to 6 carbon atoms, or an araliphatic hydrocarbon radical having 7 or 8 carbon atoms, and nB is the integer 2, 3 or 4, and a free acid, and the physiologically acceptable e.g. metal or amine, a salt thereof.

In the specifications of United Kingdom Patent No. 1,569,982, and United Kingdom Patent No. 1,583,163, the compound close to the compound represented by formula (B) is disclosed.

Further, the specification of U.S. Pat. No. 4,320,136 discloses the compound represented by formula (C)

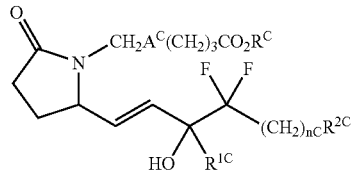

wherein $A^C$ is —CH=CH— (cis or trans), —C≡C— or —$CH_2CH_2$—;

$R^C$ is hydrogen, C1–C12 n-alkyl, branched alkyl or cycloalkyl, etc.;

$R^{1C}$ is hydrogen, methyl or ethyl;

$R^{2C}$ is phenyl or mono- or di-substituted phenyl, said substituent is selected from the group consisting of, fluorine, chlorine, methyl, methoxy, nitro or trifuloromethyl;

when $R^{2C}$ is phenyl or substituted phenyl, nC is 0–2, the definitions of the symbols are excerpt.

Further, in the specification of WO02/042268 it was disclosed that the compound is $EP_4$ receptor subtype agonist.

DISCLOSURE OF THE INVENTION $PGE_2$ receptors have four subtypes, they are called $EP_1$, $EP_2$, $EP_3$ and $EP_4$ respectively, and they have different pharmacological action respectively. Thus, if new compound can be found out to specifically bind on EP4 receptor and to weakly bind on the other subtypes, the compound does not express other action. So, it is possible for the compound to be drug having little side effect and it is necessary to found out such a drug.

In contrast, a lot of EP4 agonistic compounds have ever found out, but they have prostanoic acid skeleton, and when they are administered by systemic administration, such as oral administration, intravenous administration, etc., there is concern about side effect, such as the effect on circulatory systems, e.g. blood pressure decreased, heart rate increase, etc., diarrhea, etc. Therefore, there was large problem that the dosage capable of safety administration is limited.

As a result of the present inventors made further investigation to find out the compound which specifically binds on $EP_4$ receptor, averts the above-mentioned side effect and shows strong agonistic activity, they found out that the compound represented by formula (I) accomplished these purposes and completed the present invention.

The present inventors also thought that the therapeutic agent (treatment of diseases associated with loss in bone mass, particularly) without side-effect in systemic administration can be created, if $EP_4$ agonist which is the compound of the invention can be administered topically. They also conceived that the therapeutic agent (treatment of diseases associated with decrease in bone mass, particularly) without side-effect in systemic administration and with less frequency of administration can be created, if the $EP_4$ agonist which can be a sustained release formulation in the topical administration can be found out.

Further, the present inventors found out the compound which binds on both $EP_4$ and $EP_2$ subtype receptor. The compound which binds to both $EP_4$ and $EP_2$ subtype receptor is expected additive or multiplier effect when treatment of the disease associated with both subtype receptors.

The present invention relates to the followings:

1. A compound represented by formula (I)

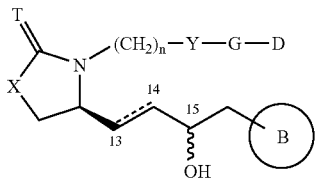

wherein ⌇ is a single bond or double bond,

⌇ is α-configuration, β-configuration or a voluntary mixture of α-configuration and β-configuration, D is —COOR$^1$ or tetrazoryl, R$^1$ is hydrogen or C1–4 alkyl, G is ringA or C1–4 alkylene, ringA is

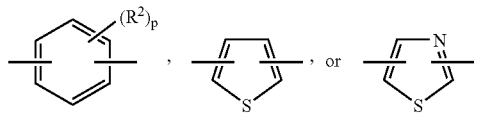

R$^2$ is a halogen atom, C1–4 alkyl or C1–4 alkoxy, p is 0 or an integer of 1–4, when p is 2 or more, plural R$^2$'s are the same or different, Y is a single bond or —S—, T is oxygen or sulfur, X is —CH$_2$—, —O— or —S—, ringB is C3–7 cycloalkyl optionally substituted,

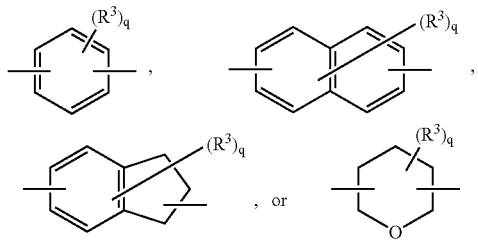

wherein R$^3$ is (1) a halogen atom, (2) C1–4 alkyl optionally substituted with 1–5 of halogen atom(s), (3) C1–4 alkoxy optionally substituted with 1–5 of halogen atom(s), (4) C1–4 alkyl substituted with C1–4 alkoxy, (5) phenyl or (6) 3- to 15-membered mono-, bi- or tri-heterocyclic aryl containing 1 to 4 hetero atom(s) selected from oxygen, nitrogen and sulfur atom(s) which may be partially or fully saturated, and (5) phenyl or (6) heterocyclic aryl in R$^3$ is optionally substituted with 1–3 of (a) halogen atom(s), (b) C1–4 alkyl, (c) C1–4 alkoxy and/or (d) nitro, q is 0 or an integer of 1–5, when q is 2 or more, plural R$^3$'s are the same or different, n is an integer of 1–4, a salt thereof, a solvate thereof, a cyclodextrin clathrate thereof, or a prodrug thereof.

2. The compound according to above-mentioned 1, which is selected from the group consisting of:

(1) 4-[(2-{(4S)-4-[(1E,3S)-4-(3-ethylphenyl)-3-hydroxybut-1-enyl]-2-oxo-1,3-thiazolidine-3-yl]ethyl)sulfanyl]butanoic acid, (2) 4-[(2-{(4S)-4-[(1E,3S)-3-hydroxy-4-phenylbut-1-enyl]-2-oxo-1,3-thiazolidine-3-yl}ethyl)sulfanyl]butanoic acid, (3) 4-{[2-((4S)-4-{(1E,3S)-4-[4-fuloro-3-(trifuloromethyl)phenyl]-3-hydroxybut-1-enyl]-2-oxo-1,3-thiazolidine-3-yl)ethyl]sulfanyl}butanoic acid, (4) 4-[(2-{(4S)-4-[(1E,3S)-4-(3,5-difulorophenyl)-3-hydroxybut-1-enyl]-2-oxo-1,3-thiazolidine-3-yl}ethyl)sulfanyl]butanoic acid, (5) 4-[(2-{(4S)-4-[(1E,3S)-3-hydroxy-4-(3-propylphenyl)but-1-enyl]-2-oxo-1,3-thiazolidine-3-yl]ethyl)sulfanyl]butanoic acid, (6) 4-[(2-{(4S)-4-[(1E,3S)-4-(3-ethyl-4-fulorophenyl)-3-hydroxybut-1-enyl]-2-oxo-1,3-thiazolidine-3-yl}ethyl)sulfanyl]butanoic acid, (7) 4-[(2-{(4S)-4-[(1E,3S)-4-(3,4-difulorophenyl)-3-hydroxybut-1-enyl]-2-oxo-1,3-thiazolidine-3-yl}ethyl)sulfanyl)butanoic acid.

(8) 4-{[2-((4S)-4-{(1E,3S)-3-hydroxy-4-[3-(trifuloromethyl)phenyl]but-1-enyl]-2-oxo-1,3-thiazolidine-3-yl}ethyl)sulfanyl]butanoic acid, (9) 4-[2-{(4S)-4-[(1E,3S)-4-(4-fuloro-3-methylphenyl)-3-hydroxybut-1-enyl]-2-oxo-1,3-thiazolidine-3-yl}ethyl)sulfanyl]butanoic acid,

(10) 4-[(2-{(4S)-4-[(1E,3S)-4-(3-fulorophenyl)-3-hydroxybut-1-enyl]-2-oxo-1,3-thiazolidine-3-yl}ethyl)sulfanyl]butanoic acid,

(11) 4-[(2-{(4S)-4-[(1E,3S)-4-(3-chloro-4-fulorophenyl)-3-hydroxybut-1-enyl]-2-oxo-1,3-thiazolidine-3-yl}ethyl)sulfanyl]butanoic acid,

(12) 4-{[2-((4S)-4-{(1E,3S)-3-hydroxy-4-[3-(methoxymethyl)phenyl]but-1-enyl}-2-oxo-1,3-thiazolidine-3-yl)ethyl]sulfanyl}butanoic acid,

(13) 7-{(2R)-2-[(1E,3S)-4-(4-fulorophenyl)-3-hydroxybut-1-enyl]-5-thioxopyrrolidine-1-yl}heptanoic acid,

(14) 7-{(2R)-2-[(1E,3S)-4-(3,5-difulorophenyl)-3-hydroxybut-1-enyl]-5-thioxopyrrolidine-1-yl}heptanoic acid,

(15) 7-((2R)-2-{(1E,3S)-4-[4-fuloro-3-(trifuloromethyl)phenyl]-3-hydroxybut-1-enyl}-5-thioxopyrrolidine-1-yl)heptanoic acid,

(16) 7-{(2R)-2-[(1E,3S)-4-(4-fuloro-3-methylphenyl)-3-hydroxybut-1-enyl]-5-thioxopyrrolidine-1-yl}heptanoic acid,

(17) 7-{(2R)-2-[(1E,3S)-4-(3-ethyl-4-fulorophenyl)-3-hydroxybut-1-enyl]-5-thioxopyrrolidine-1-yl}heptanoic acid,

(18) 7-((2R)-2-{(1E,3S)-3-hydroxy-4-[3-(trifluoromethyl)phenyl]but-1-enyl}-5-thioxopyrrolidine-1-yl)heptanoic acid,

(19) 7-{(2R)-2-[(1E,3S)-4-(3-fulorophenyl)-3-hydroxybut-1-enyl]-5-thioxopyrrolidine-1-yl}heptanoic acid,

(20) 7-{(2R)-2-[(1E,3S)-3-hydroxy-4-phenylbut-1-enyl]-5-thioxopyrrolidine-1-yl}heptanoic acid,

(21) 7-{(2R)-2-[(1E,3S)-4-(3,4-difulorophenyl)-3-hydoroxybut-1-enyl]-5-thioxopyrrolidine-1-yl}heptanoic acid,

(22) 7-{(2R)-2-[(1E,3S)-4-(3-chloro-4-fulorophenyl)-3-hydroxybut-1-enyl]-5-thioxiopyrrolidine-1-yl}heptanoic acid,

(23) 7-{(2R)-2-[(1E,3S)-4-(3-ethylphenyl)-3-hydroxybut-1-enyl]-5-thioxopyrrolidine-1-yl}heptanoic acid,

(24) 7-{(2R)-2-[(1E,3S)-3-hydroxy-4-(3-propylphenyl)but-1-enyl]-5-thioxopyrrolidine-1-yl}heptanoic acid.

3. The compound according to above-mentioned 1, which is represented by formula (I-1):

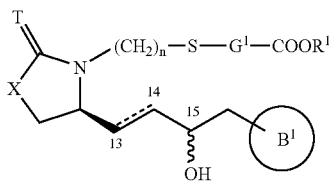

(I-1)

wherein $G^1$ is ringA$^1$ or C1–4 alkylene,
ringA$^1$ is

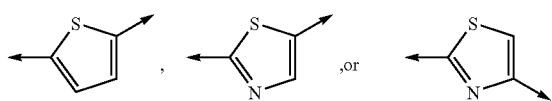

wherein left-pointing arrow represents binding to S, and right-pointing arrow represents binding to COOR$^1$,
ringB$^1$ is C3–7 cycloalkyl,

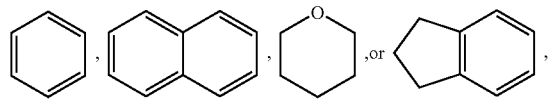

ringB$^1$ may be substituted with a halogen atom, C1–4 alkyl, phenyl, methoxymethyl, trifluoromethyl and/or trifuloromethoxy, other symbols have the same meanings as described in above-mentioned 1, and wherein when T is oxygen, X is —CH$_2$—, and
when n is an integer of 2–4, $G^1$ is ringA$^1$.

4. The compound according to above-mentioned 3, which is selected from the group consisting of:

(1) (15α,13E)-9-oxo-15-hydroxy-16-(3-phenylphenyl)-17,18,19,20-tetranol-5-thia-8-aza-10-oxaprost-13-enoic acid, (2) (15α,13E)-9-oxo-15-hydroxy-16-(3-ethylphenyl)-17,18,19,20-tetranol-5-thia-8-aza-10-oxaprost-13-enoic acid, (3) (15α,13E)-9-oxo-15-hydroxy-16-(3-chloro-4-fulorophenyl)-17,18,19,20-tetranol-5-thia-8-aza-10-oxaprost-13-enoic acid, (4) (15α,13E)-9-oxo-15-hydroxy-16-(naphthalene-2-yl)-17,18,19,20-tetranol-5-thia-8-aza-10-oxaprost-13-enoic acid, (5) (15α,13E)-9-oxo-15-hydroxy-16-(3-trifuloromethoxyphenyl)-17,18,19,20-tetranol-5-thia-8-aza-10-oxaprost-13-enoic acid, (6) (15α,13E)-9-oxo-15-hydroxy-16-(4-fuloro-3-phenylphenyl)-17,18,19,20-tetranol-5-thia-8-aza-10-oxaprost-13-enoic acid, (7) (15α,13E)-9-oxo-15-hydroxy-16-(4-fuloro-3-methylphenyl)-17,18,19,20-tetranol-5-thia-8-aza-10-oxaprost-13-enoic acid, (8) (15α,13E)-9-oxo-15-hydroxy-16-(3,5-difulorophenyl)-17,18,19,20-tetranol-5-thia-8-aza-10-oxaprost-13-enoic acid, (9) (15α,13E)-9-oxo-15-hydroxy-16-(3-fulorophenyl)-17,18,19,20-tetranol-5-thia-8-aza-10-oxaprost-13-enoic acid,

(10) (15α,13E)-9-oxo-15-hydroxy-16-(4-fuloro-3-trifuloromethylphenyl)-17,18,19,20-tetranol-5-thia-8-aza-10-oxaprost-13-enoic acid,

(11) (15α,13E)-9-oxo-15-hydroxy-16-(3-trifuloromethylphenyl)-17,18,19,20-tetranol-5-thia-8-aza-10-oxaprost-13-enoic acid,

(12) (15α,13E)-9-oxo-15-hydroxy-16-(3,4-difulorophenyl)-17,18,19,20-tetranol-5-thia-8-aza-10-oxaprost-13-enoic acid,

(13) (15α,13E)-9-oxo-15-hydroxy-16-phenyl-17,18,19,20-tetranol-5-thia-8-aza-10-oxaprost-13-enoic acid,

(14) (15α,13E)-9-oxo-15-hydroxy-16-(3-propylphenyl)-17,18,19,20-tetranol-5-thia-8-aza-10-oxaprost-13-enoic acid,

(15) (15α,13E)-9-oxo-15-hydroxy-16-(3-methoxymethylphenyl)-17,18,19,20-tetranol-5-thia-8-aza-10-oxaprost-13-enoic acid,

(16) (15α,13E)-9-oxo-15-hydroxy-16-(3-ethyl-4-fulorophenyl)-17,18,19,20-tetranol-5-thia-8-aza-10-oxaprost-13-enoic acid,

(17) (15α,13E)-9-oxo-15-hydroxy-16-phenyl-5-(4-carboxythiazol-2-yl)-1,2,3,4,17,18,19,20-octanol-5-thia-8-aza-10-oxaprost-13-ene,

(18) (15α,13E)-9-oxo-15-hydroxy-16-(3-methylphenyl)-5-(4-carboxythiazol-2-yl)-1,2,3,4,17,18,19,20-octanol-5-thia-8-aza-10-oxaprost-13-ene,

(19) (15α,13E)-9-oxo-15-hydroxy-16-(4-fulorophenyl)-5-(4-carboxythiazol-2-yl)-1,2,3,4,17,18,19,20-octanol-5-thia-8-aza-10-oxaprost-13-ene,

(20) (15α,13E)-9-oxo-15-hydroxy-16-(naphthalene-2-yl)-5-(4-carboxythiazol-2-yl)-1,2,3,4,17,18,19,20-octanol-5-thia-8-aza-10-oxaprost-13-ene,

(21) (15α,13E)-9-oxo-15-hydroxy-16-(3-phenylphenyl)-5-(4-carboxythiazol-2-yl)-1,2,3,4,17,18,19,20-octanol-5-thia-8-aza-10-oxaprost-13-ene,

(22) (15α,13E)-9-oxo-15-hydroxy-16-(3-phenylphenyl)-5-(5-carboxythiophene-2-yl)-1,2,3,4,17,18,19,20-octanol-5-thia-8-azaprost-13-ene,

(23) (15α,13E)-9-oxo-15-hydroxy-16-(naphthalene-2-yl)-5-(5-carboxythiophene-2-yl)-1,2,3,4,17,18,19,20-octanol-5-thia-8-azaprost-13-ene,

(24) (15α,13E)-9-oxo-15-hydroxy-16-(4-fuloro-3-phenylphenyl)-5-(5-carboxythiophene-2-yl)-1,2,3,4,17,18,19,20-octanol-5-thia-8-azaprost-13-ene,

(25) (15α,13E)-9-oxo-15-hydroxy-16-(3-ethylphenyl)-5-(5-carboxythiophene-2-yl)-1,2,3,4,17,18,19,20-octanol-5-thia-8-azaprost-13-ene,

(26) (15α,13E)-9-oxo-15-hydroxy-16-(3-methylphenyl)-5-(5-carboxythiophene-2-yl)-1,2,3,4,17,18,19,20-octanol-5-thia-8-azaprost-13-ene,

(27) (15α,13E)-9-oxo-15-hydroxy-16-(3-trifuloromethoxyphenyl)-5-(5-carboxythiophene-2-yl)-1,2,3,4,17,18,19,20-octanol-5-thia-8-azaprost-13-ene,

(28) (15α,13E)-9-oxo-15-hydroxy-16-(4-fuloro-3-phenylphenyl)-5-(4-carboxythiazol-2-yl)-1,2,3,4,17,18,19,20-octanol-5-thia-8-azaprost-13-ene,

(29) (15α,13E)-9-oxo-15-hydroxy-16-(3-ethylphenyl)-5-(4-carboxythiazol-2-yl)-1,2,3,4,17,18,19,20-octanol-5-thia-8-azaprost-13-ene,

(30) (15α,13E)-9-oxo-15-hydroxy-16-(naphthalene-2-yl)-5-(4-carboxythiazol-2-yl)-1,2,3,4,17,18,19,20-octanol-5-thia-8-azaprost-13-ene,

(31) (15α,13E)-9-oxo-15-hydroxy-16-(3-trifuloromethoxyphenyl)-5-(4-carboxythiazol-2-yl)-1,2,3,4,17,18,19,20-octanol-5-thia-8-azaprost-13-ene,

(32) (15α,13E)-9-oxo-15-hydroxy-16-(3-chloro-4-fulorophenyl)-5-(4-carboxythiazol-2-yl)-1,2,3,4,17,18,19,20-octanol-5-thia-8-azaprost-13-ene,
(33) (15α,13E)-9-oxo-15-hydroxy-16-cyclopropyl-5-(4-carboxythiazol-2-yl)-1,2,3,4,17,18,19,20-octanol-5-thia-8-azaprost-13-ene,
(34) (15α,13E)-9-oxo-15-hydroxy-16-cyclohexyl-5-(4-carboxythiazol-2-yl)-1,2,3,4,17,18,19,20-octanol-5-thia-8-azaprost-13-ene,
(35) (15α,13E)-9-oxo-15-hydroxy-16-(4-fulorophenyl)-5-(5-carboxythiazol-2-yl)-1,2,3,4,17,18,19,20-octanol-5-thia-8-azaprost-13-ene,
(36) (15α,13E)-9-oxo-15-hydroxy-16-cyclobutyl-5-(4-carboxythiazol-2-yl)-1,2,3,4,17,18,19,20-octanol-5-thia-8-azaprost-13-ene,
(37) (15α,13E)-9-oxo-15-hydroxy-16-(4-chlorophenyl)-5-(4-carboxythiazol-2-yl)-1,2,3,4,17,18,19,20-octanol-5-thia-8-azaprost-13-ene,
(38) (15α,13E)-9-oxo-15-hydroxy-16-cycloheptyl-5-(4-carboxythiazol-2-yl)-1,2,3,4,17,18,19,20-octanol-5-thia-8-azaprost-13-ene,
(39) (15α,13E)-9-oxo-15-hydroxy-16-(indane-2-yl)-5-(4-carboxythiazol-2-yl)-1,2,3,4,17,18,19,20-octanol-5-thia-8-azaprost-13-ene,
(40) (15α,13E)-9-oxo-15-hydroxy-16-(tetrahydropyran-4-yl)-5-(4-carboxythiazol-2-yl)-1,2,3,4,17,18,19,20-octanol-5-thia-8-azaprost-13-ene,
(41) (15α,13E)-9-oxo-15-hydroxy-16-(7-methylnaphthalene-2-yl)-5-(4-carboxythiazol-2-yl)-1,2,3,4,17,18,19,20-octanol-5-thia-8-azaprost-13-ene,
(42) (15α,13E)-9-oxo-15-hydroxy-16-(4-fulorophenyl)-17,18,19,20-tetranol-5,10-dithia-8-azaprost-13-enoic acid,
(43) (15α,13E)-9-oxo-15-hydroxy-16-(4-fulorophenyl)-17,18,19,20-tetranol-6-thia-8-azaprost-13-enoic acid,
(44) (15α,13E)-9-oxo-15-hydroxy-16-(3-methylphenyl)-17,18,19,20-tetranol-6-thia-8-azaprost-13-enoic acid, and
(45) (15α,13E)-9-thioxo-15-hydroxy-16-(4-fulorophenyl)-17,18,19,20-tetranol-5-thia-8-azaprost-13-enoic acid.

5. The compound according to above-mentioned 1, which is represented by formula (I-2):

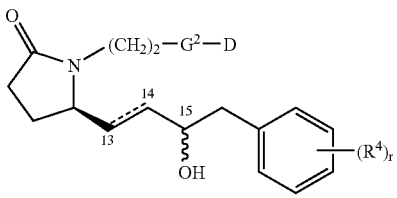

(I-2)

wherein G² is

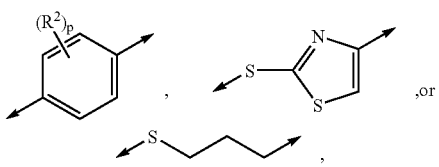

wherein left-pointing arrow represents binding to —(CH₂)₂—, and right-pointing arrow represents binding to D, R⁴ is (1) a halogen atom, (2) C1–4 alkyl (3) C1–4 alkoxy, (4) C1–4 alkyl optionally substituted with 1–5 of halogen atom(s), (5) C1–4 alkoxy optionally substituted with 1–5 of halogen atom(s), (6) phenyl or (7) 3- to 15-membered mono-, bi- or tri-heterocyclic aryl containing 1 to 4 hetero atom(s) selected from oxygen, nitrogen and sulfur atom(s) which may be partially or fully saturated, and (6) phenyl or (7) heterocyclic in the R⁴ may be substituted with 1–3 of (a) a halogen atom(s), (b) C1–4 alkyl (c) C1–4 alkoxy and/or (d) nitro,
r is an integer 1 to 5, and
other symbols have the same meanings as described in above-mentioned 1.

6. The compound according to above-mentioned 5, which is selected from the group consisting of
(1) (15α,13E)-1,6-(1,4-interphenylene)-9-oxo-15-hydroxy-16-(3,5-dimethylphenyl)-2,3,4,5,17,18,19,20-octanol-8-azaprost-13-enoic acid,
(2) (15α,13E)-1,6-(1,4-interphenylene)-9-oxo-15-hydroxy-16-(3-(benzothiazol-2-yl)phenyl)-2,3,4,5,17,18,19,20-octanol-8-azaprost-13-enoic acid,
(3) (15α,13E)-1,6-(1,4-interphenylene)-9-oxo-15-hydroxy-16-(4-fulorophenyl)-2,3,4,5,17,18,19,20-octanol-8-azaprost-13-enoic acid,
(4) (15α,13E)-9-oxo-15-hydroxy-16-(3-(5-methylbenzothiazol-2-yl)phenyl)-5-(4-carboxythiazol-2-yl)-1,2,3,4,17,18,19,20-octanol-5-thia-8-azaprost-13-ene,
(5) (15α,13E)-1,6-(1,4-interphenylene)-9-oxo-15-hydroxy-16-(3-(5-methylbenzoxazol-2-yl)phenyl)-2,3,4,5,17,18,19,20-octanol-8-azaprost-13-enoic acid,
(6) (15α,13E)-9-oxo-15-hydroxy-16-(3-(6-methylbenzoxazol-2-yl)phenyl)-5-(4-carboxythiazol-2-yl)-1,2,3,4,17,18,19,20-octanol-5-thia-8-azaprost-13-ene,
(7) (15α,13E)-1,6-(1,4-interphenylene)-9-oxo-15-hydroxy-16-(3-(6-methylbenzoxazol-2-yl)phenyl)-2,3,4,5,17,18,19,20-octanol-8-azaprost-13-enoic acid,
(8) (15α,13E)-1,6-(1,4-interphenylene)-9-oxo-15-hydroxy-16-(3-(4-methylbenzothiazol-2-yl)phenyl)-2,3,4,5,17,18,19,20-octanol-8-azaprost-13-enoic acid,
(9) (15α,13E)-9-oxo-15-hydroxy-16-(3-(4-methylbenzothiazol-2-yl)phenyl)-5-(4-carboxythiazol-2-yl)-1,2,3,4,17,18,19,20-octanol-5-thia-8-azaprost-13-ene,
(10) (15α,13E)-1,6-(2-fuloro-1,4-interphenylene)-9-oxo-15-hydroxy-16-(3-methylphenyl)-2,3,4,5,17,18,19,20-octanol-8-azaprost-13-enoic acid,
(11) (15α,13E)-1,6-(3-methyl-1,4-interphenylene)-9-oxo-15-hydroxy-16-(3-methylphenyl)-2,3,4,5,17,18,19,20-octanol-8-azaprost-13-enoic acid,
(12) (15α,13E)-9-oxo-15-hydroxy-16-(3-(5,7-dimethylbenzoxazol-2-yl)phenyl)-5-(4-carboxythiazol-2-yl)-1,2,3,4,17,18,19,20-octanol-5-thia-8-azaprost-13-ene,
(13) (15α,13E)-9-oxo-15-hydroxy-16-(3-(5-chlorobenzothiazol-2-yl)phenyl)-5-(4-carboxythiazol-2-yl)-1,2,3,4,17,18,19,20-octanol-5-thia-8-azaprost-13-ene,
(14) (15α,13E)-1,6-(1,4-interphenylene)-9-oxo-15-hydroxy-16-(3-(5-chlorobenzothiazol-2-yl)phenyl)-2,3,4,5,17,18,19,20-octanol-8-azaprost-13-enoic acid,
(15) (15α)-9-oxo-15-hydroxy-16-(3-(2,4-dimethylphenyl)phenyl)-5-(4-carboxythiazol-2-yl)-1,2,3,4,17,18,19,20-octanol-5-thia-8-azaprost-13-ene,
(16) (15α,13E)-9-oxo-15-hydroxy-16-(3-(3,4-dimethylphenyl)phenyl)-5-(4-carboxythiazol-2-yl)-1,2,3,4,17,18,19,20-octanol-5-thia-8-azaprost-13-ene,
(17) (15α,13E)-1,6-(1,4-interphenylene)-9-oxo-15-hydroxy-16-(3,4-difulorophenyl)-2,3,4,5,17,18,19,20-octanol-8-azaprost-13-enoic acid,

(18) (15α,13E)-1,6-(2-methyl-1,4-interphenylene)-9-oxo-15-hydroxy-16-(3-methylphenyl)-2,3,4,5,17,18,19,20-octanol-8-azaprost-13-enoic acid,

(19) (15α,13E)-9-oxo-15-hydroxy-16-(3-(5-chlorobenzoxazol-2-yl)phenyl)-5-(4-carboxythiazol-2-yl)-1,2,3,4,17,18,19,20-octanol-5-thia-8-azaprost-13-ene,

(20) (15α,13E)-1,6-(1,4-interphenylene)-9-oxo-15-hydroxy-16-(3-methyl-4-fulorophenyl)-2,3,4,5,17,18,19,20-octanol-8-azaprost-13-enoic acid,

(21) (15α,13E)-1,6-(1,4-interphenylene)-9-oxo-15-hydroxy-16-(3-chloro-4-fulorophenyl)-2,3,4,5,17,18,19,20-octanol-8-azaprost-13-enoic acid,

(22) (15α,13E)-1,6-(3-methoxy-1,4-interphenylene)-9-oxo-15-hydroxy-16-(3-methylphenyl)-2,3,4,5,17,18,19,20-octanol-8-azaprost-13-enoic acid,

(23) (15α,13E)-9-oxo-15-hydroxy-16-(3-trifuloromethoxyphenyl)-17,18,19,20-tetranol-5-thia-8-azaprost-13-enoic acid,

(24) (15α,13E)-9-oxo-15-hydroxy-16-(3,5-difulorophenyl)-17,18,19,20-tetranol-5-thia-8-azaprost-13-enoic acid,

(25) (15α,13E)-9-oxo-15-hydroxy-16-(3-(phenyl)phenyl)-17,18,19,20-tetranol-5-thia-8-azaprost-13-enoic acid,

(26) (15α,13E)-9-oxo-15-hydroxy-16-(3-(4-fulorophenyl)phenyl)-17,18,19,20-tetranol-5-thia-8-azaprost-13-enoic acid, and

(27) (15α,13E)-9-oxo-15-hydroxy-16-(3-phenyl-4-fulorophenyl)-17,18,19,20-tetranol-5-thia-8-azaprost-13-enoic acid.

7. A pharmaceutical composition comprising the compound represented by formula (I) according to above-mentioned 1, a salt thereof, a solvate thereof, a cyclodextrin clathlate thereof, or a prodrug thereof.

8. An EP4 agonist comprising the compound represented by formula (I) according to above-mentioned 1, a salt thereof, a solvate thereof or a cyclodextrin clathlate thereof, or a prodrug thereof.

9. A method for preventing and/or treating EP4-mediated disease, which comprises administrating to a mammal an effective amount of the compound represented by formula (I) according to claim 1, a salt thereof, a solvate thereof or a cyclodextrin clathrate thereof, or a prodrug thereof.

10. Use of the compound represented by formula (I) according to above-mentioned 1, a salt thereof, a solvate thereof, a cyclodextrin clathrate thereof, or a prodrug thereof for the manufacture of an EP4 agonist.

11. A method for preparing the compound represented by formula (I) according to the above-mentioned 1, a salt thereof, a solvate thereof, a cyclodextrin clathrate thereof, or a prodrug thereof.

In the specification, C1–4 alkyl means methyl, ethyl, propyl, butyl and the isomers thereof.

In the specification, C1–4 alkylene means methylene, ethylene, trimethylene, tetramethylene and the isomers thereof.

In the specification, C1–4 alkoxy means methoxy, ethoxy, propoxy, butoxy and the isomers thereof.

In the specification, C3–7 cycloalkyl means cyclopropyl, cyclobutyl, cyclopentyl, cyclohexyl and cycloheptyl.

In the specification, halogen atom means fluorine, chlorine, bromine and iodine.

In the specification, substituent in the C3–7 cycloalkyl optionally with substituent represented by ringB means (1) halogen atom, (2) C1–4 alkyl optionally substituted with 1–5 of halogen atom(s), (3) C1–4 alkoxy optionally substituted with 1–5 of halogen atom(s), (4) C1–4 alkyl substituted with C1–4 alkoxy, (5) phenyl or (6) 3- to 15-membered mono-, bi-, or tri-heterocyclic aryl may be partially or fully saturated containing 1 to 4 hetero atom(s) selected from oxygen, nitrogen and sulfur atom(s). Among these, (5) phenyl or (6) heterocyclic ring may be substituted with 1–3 of (a) halogen atom(s), (b) C1–4 alkyl, (3) C1–4 alkoxy and/or (d) nitro.

In the specification, C1–4 alkyl substituted with 1–5 of halogen atom(s) represented by $R^4$ means fuloromethyl, difuloromethyl, trifuloromethyl, chloromethyl, dichloromethyl, trichloromethyl, bromomethyl, dibromomethyl, tribromomethyl, iodomethyl, diiodomethyl, triiodomethyl, fuloroethyl, difuloroethyl, trifuloroethyl, tetrafuloroethyl, pentafuloroethyl, chloroethyl, dichloroethyl, trichloroethyl, tetrachloroethyl, pentachloroethyl, fuloropropyl, difuloropropyl, trifiloropropyl, tetrafuloropropyl, pentafuloropropyl, chloropropyl, dichloropropyl, trichloropropyl, tetrachloropropyl, pentachloropropyl, fulorobutyl, difulorobutyl, trifulorobutyl, tetrafulorobutyl, pentafulorobutyl, chlorobutyl, dichlorobutyl, trichlorobutyl, tetrachlorobutyl, pentachlorobutyl and the isomers thereof.

In the specification, C1–4 alkyl optionally substituted with 1–5 of halogen atom(s) represented by $R^3$ means the same meaning as that of the above mentioned C1–4 alkyl or C1–4 alkyl substituted with 1–5 of halogen atom(s) represented by $R^4$.

In the specification, C1–4 alkoxy substituted with 1–5 of halogen atom(s) represented by $R^4$ means fuloromethoxy, difuloromethoxy, trifuloromethoxy, chloromethoxy, dichloromethoxy, trichloromethoxy, bromomethoxy, dibromomethoxy, tribromomethoxy, iodomethoxy, diiodomethoxy, triiodomethoxy, fuloroethoxy, difuloroethoxy, trifuloroethoxy, tetrafuloroethoxy, pentafuloroethoxy, chloroethoxy, dichloroethoxy, trichlioroethoxy, tetrachloroethoxy, pentachloroethoxy, fuloropropoxy, difuloropropoxy, trifuloropropoxy, tetrafuloropropoxy, pentafuloropropoxy, chloropropoxy, dichloropropoxy, trichloropropoxy, tetrachlioropropoxy, pentachloropropoxy, fulorobutoxy, difulorobutoxy, trifulorobutoxy, tetarfulorobutoxy, pentafulorobutoxy, chlorobutoxy, dichlorobutoxy, trichlorobutoxy, tetrachlorobutoxy, pentachlorobutoxy and the isomers thereof.

In the specification, C1–4 alkoxy optionally substituted with 1–5 of halogen atom(s) represented by $R^3$ has the same meaning as that of the above-mentioned C1–4 alkoxy or C1–4 alkoxy substituted with 1–5 of halogen atom(s) represented by $R^4$.

In the specification, 3- to 15-membered mono-, bi-, or tri-heterocyclic aryl may be partially or fully saturated containing 1 to 4 hetero atom(s) selected from oxygen, nitrogen and sulfur atom(s) represented by $R^3$ or $R^4$ means, pyrrole, imidazole, triazole, tetrazole, pyrazole, pyridine, pyrazine, pyrimidine, pyridazine, azepine, diazepine, furan, pyran, oxepine, thiophene, thiopyran, thiepine, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepine, indole, isoindole, indolizine, benzofuran, isobenzofuran, benzothiophene, isobenzothiophene, dithianaphthalene, indazole, quinoline, isoquinoline, quinolizine, purine, phthalazine, pteridine, naphthyridine, quinoxaline, quinazoline, cinnoline, benzoxazole, benzothiazole, benzimidazole, chromene, benzoxepine, benzoxazepine, benzoxadiazepine, benzothiepine, benzothiazepine, benzothiadiazepine, benzazepine, benzodiazepine, benzofurazan, benzothiadiazole, benzotriazole, carbazole, beta-carboline, acridine, phenazine, dibenzofuran, xanthene, dibenzothiophene, phenothiazine, phenoxazine, phenoxathiin, thianthrene, phenanthridine, phenanthroline, perimidine, aziridine, azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, oxirane, oxetane, dihydrofuran, tetrahydrofuran, dihydropyran, tetrahydropyran, dihydrooxepine, tetrahydrooxepine, perhydrooxepine, thiirane, thietane, dihydrothiophene, tetrahydrothiophene, dihydrothiopyran, tetrahydrothiopyran, dihydrothiepine, tetrahydrothiepine, perhydrothiepine, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzoxathiane, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dihydrobenzazepine, tetrahydrobenzazepine, dihydrobenzodiazepine, tetrahydrobenzodiazepine, benzodioxepane, dihydrobenzoxazepine, tetrahydrobenzoxazepine, dihydrocarbazole, tetrahydrocarbazole, perhydrocarbazole, dihydroacridine, tetrahydroacridine, perhydroacridine, dihydrodibenzofuran, dihydrodibenzothiophene, tetrahydrodibenzofuran, tetrahydrodibenzothiophene, perhydrodibenzofuran, perhydrodibenzothiophene, dioxolane, dioxane, dithiolane, dithiane, dioxaindan, benzodioxane, chroman, benzodithiolane, benzodithiane, 8-aza-1,4-dioxaspiro[4.5]decane, 3-azaspiro[5.5]undecane, 1,3,8-triazaspiro[4.5]decane and so on.

In the specification, a connectable bond represented by Y means that —(CH$_2$)$_2$— binds directly to G.

In the present invention, unless otherwise specified, the symbol ⁓ means that the α-configuration substituent, the symbol ⁓ means that the β-configuration substituent, the symbol ⁓ means α-configuration, β-configuration or a voluntary mixture of α-configuration and β-configuration, and the symbol ⁓ means that there is a voluntary mixture of α-configuration and β-configuration as would be clear to the person skilled in the art.

Unless otherwise specified, all isomers are included in the present invention. For example, alkyl, alkenyl, alkynyl, alkoxy, alkylthio, alkylene alkenylene and alkynylene group means straight-chain or branched-chain ones. In addition, isomers on double bond, ring, fused ring (E-, Z-, cis-, trans-isomer), isomers generated from asymmetric carbon atom(s) (R-, S-isomer, α-, β-configuration, enantiomer, diastereomer), optically active isomers (D-, L-, d-, 1-isomer), polar compounds generated by chromatographic separation (more polar compound, less polar compound), equilibrium compounds, rotational isomers, mixtures thereof at voluntary ratios and racemic mixtures are also included in the present invention.

The compounds represented by formula (I) may be converted into the salts by conventional means. As salts, pharmaceutically acceptable salts are preferred.

The salts include salts of alkali metals, salts of alkaline earth metals, ammonium salts, amine salts, acid addition salts and so on.

As the salts, water soluble salts are preferred. The suitable salts include for example, salts of alkali metals (e.g. potassium, sodium, lithium, etc.), salts of alkaline earth metals (e.g. calcium, magnesium, etc.), ammonium salts (e.g. tetramethylammonium salt, tetrabutylammonium salt, etc.), pharmaceutical acceptable salts of organic amine (e.g. triethylamine, methylamine, dimethylamine, cyclopentylamine, benzylamine, phenethylamine, piperidine, monoethanolamine, diethanolamine, tris(hydroxymethyl)aminomethane, lysine, arginine, N-methyl-D-glucamine, etc.).

As acid addition salts, water soluble salts are preferred. The suitable acid addition salts include for example, salts of inorganic acids (e.g. hydrochloride, hydrobromide, hydroiodide, sulfate, phosphate, nitrate, etc.), and salts of organic acids (e.g. acetate, trifluoroacetate, lactate, tartrate, oxalate, fumarate, maleate, benzoate, citrate, methanesulfonate, ethanesulfonate, benzenesulfonate, toluenesulfonate, isethionate, glucuronate, gluconate, etc.).

The compounds represented by formula (I) and salts thereof may be converted into the solvate.

Non-toxic and water-soluble solvates are preferred. The suitable solvates include for example, hydrates, solvates of the alcohols (e.g. ethanol, etc.), and so on.

The compounds represented by formula (I) or pharmaceutically acceptable salts thereof are all preferred. They include concretely, the compounds described in Example or pharmaceutically acceptable salts thereof.

The compounds of the present invention may be converted into the corresponding cyclodextrin clathrates by the method described in the specification of JP-B-50-3362 (U.S. Pat. No. 4,054,736), 52-31404 or 61-52146 using α-, β- or γ-cyclodextrin or a mixture thereof. Converting into the corresponding cyclodextrin clathrates serves to increase the stability and solubility in water of the compounds, and therefore it is preferred in the use for pharmaceuticals.

The prodrug of the compounds represented by formula (I) means a compound is the compound represented by formula (I) by reaction with enzymes, gastric acids and so on within an organism. The prodrug of the compounds represented by formula (I) include, when the compounds represented by formula (I) have amino, the prodrug is the compounds the amino of which is acylated, alkylated, phosphorylated (e.g. the compounds are that the amino of the compounds represented by formula (I) is eicosanoated, alanylated, pentylaminocarbonylated, (5-methyl-2-oxo-1,3-dioxolane-4-yl)methoxycarbonylated, tetrahydrofuranated, pyrrolidylmethylated, pivaloyloxymethylated, acetoxymethylated, tert-butylated, etc.); when the compounds represented by formula (I) have hydroxyl, the prodrug is the compounds the hydroxyl of which are acylated, alkylated, phosphorylated, borated (e.g. the compounds are that the hydroxyl of the compounds represented by formula (I) are acetylated, palmitoylated, propanoylated, pivaloylated, succinylated, fumarylated, alanylated, dimethylaminomethylcarbonylated, etc.); when the compounds represented by formula (I) have carboxyl, the prodrug is the compound the carboxyl of which are esterified, amidated (e.g. the compounds are that the carboxyl of the compounds represented by formula (I) is ethylesterified, isopropylesterified, phenylesterified, carboxymethylesterified, dimethylaminomethylesterified, pivaloyloxymethylesterified, ethoxycarbonyloxyethylesterified, phthalidylesterified, (5-methyl-2-oxo-1,3-dioxolene-4-yl)methylesterified, cyclohexyloxycarbonyletlhylesterified, methylamidated, etc.); and so on. In addition, the above-mentioned carboxyl may be esterified with alcohol or phenol, for example

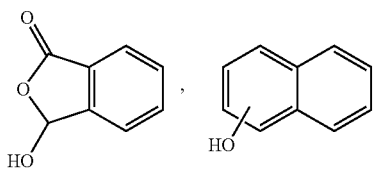

and so on. These alcohol or phenol may be substituted with carboxyl and so on.

These compounds can be manufactured by the conventional methods. In addition, the prodrugs of the compounds represented by formula (I) may be either solvates or non-solvates.

EP4 agonists of the present invention have only to have EP4 agonistic action, whichever they are selective EP4 agonist, or non-selective EP4 agonist is allowed. Selective EP4 agonist is preferred.

In the present invention, 13–14 position being a double bond is preferred in the formula (I), (I-1) and (I-2).

In the present invention, hydroxyl of 15 position being α-configuration is preferred in the formula (I), (I-1) and (I-2).

In the present invention, each group represented by ring A, ring B, D, G, T, X, Y, $R^1$, $R^2$ and $R^3$ is all preferred in the formula (I), (I-1) and (I-2). In particular, the group described below is preferred.

In the present invention, as ringA,

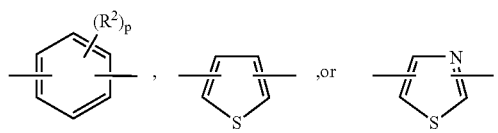

(wherein, all the symbols have the same meanings as the above-mentioned.) is preferred in the formula (I).

In the present invention, as ringB,

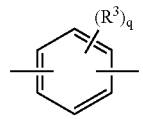

(wherein, all the symbols have the same meanings as the above-mentioned.) is preferred in the formula (I).

In the present invention, as D, $COOR^1$ is preferred in the formula (I) and (I-2).

In the present invention, as G, ringA, trimethylene or tetramethylene is preferred in the formula (I).

In the present invention, as T, oxygen atom or sulfur atom is preferred in the formula (I) and (I-1).

In the present invention, as X, —$CH_2$—, —O— or —S— is preferred in the formula (I) and (I-1).

In the present invention, as Y, connectable bond or —S— is preferred in the formula (I).

In the present invention, as $R^1$, hydrogen atom, methyl or isopropyl is preferred in the formula (I), (I-1) and (I-2).

In the present invention, as $R^2$, fluorine, chlorine, methyl or methoxy is preferred in the formula (I).

In the present invention, as $R^3$, fluorine, chlorine, methyl, ethyl, propyl, trifuloromethyl, trifuloromethoxy or methoxymethyl is preferred in the formula (I).

In the present invention, each group represented by ring$A^1$, ring$B^1$, and $G^1$ is all preferred in the formula (I-1). In particular, the group described below is preferred.

In the present invention, as ring$A^1$,

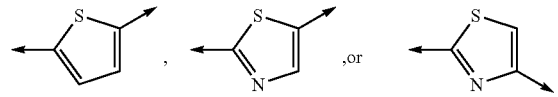

(wherein, all the symbols have the same meanings as the above-mentioned.) is preferred in the formula (I-1).

In the present invention, as ring$B^1$,

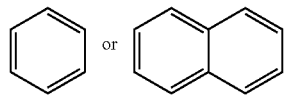

(wherein, all the symbols have the same meanings as the above-mentioned.) is preferred in the formula (I-1).

In the present invention, as $G^1$, ring$A^1$, trimethylene or tetramethylene is preferred in the formula (I-1).

In the present invention, each group represented by $G^2$ and $R^4$ is all preferred in the formula (I-2). In particular, the group described below is preferred. In the present invention, as $G^2$,

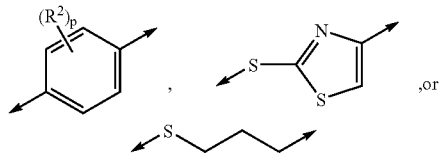

(wherein, all the symbols have the same meanings as the above-mentioned.) is preferred in the formula (I-2).

In the present invention, as $R^4$, fluorine, methyl, trifluoromethoxy, phenyl or heterocyclic ring is preferred in the formula (I-2).

In the present invention, n is preferably 1 or 2 in the formula (I), (I-1) and (I-2).

In the present invention, p is preferably 0 or 1 in the formula (I), (I-1) and (I-2).

In the present invention, q is preferably 1 or 2 in the formula (I), (I-1) and (I-2).

In the present invention, r is preferably 1 or 2 in the formula (I), (I-1) and (I-2).

In the present invention, all the compounds described in Examples are preferred.

Processes for the Preparation of the Compound of the Present Invention

The compound of the present invention represented by formula (I) can be prepared by the processed described in WO03/009872, the following processes, the pursuant these processes, and the processes shown in Examples. Still, ingredients may be used as salts in the following each processes for the preparation. As these salts, the salts described as the salts in the above-mentioned formula (I) are used.

[1] Among the compounds represented by formula (I), the compound 13–14 position of which is a double bond, i.e. the compound represented by formula (I-A)

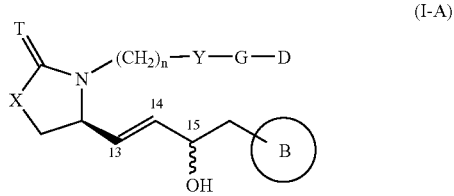

(wherein, all the symbols have the same meanings as the above-mentioned.) can be prepared by the following processes.

The compound represented by formula (I-A) can be prepared by subjecting to a reduction reaction a compound represented by formula (II),

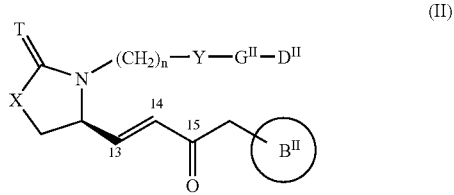

(wherein, $B^{II}$, $D^{II}$ and $G^{II}$ have the same meanings as that of B, D and G, but carboxyl, hydroxyl, amino and mercapto included the group represented by $B^{II}$, $D^{II}$ and $G^{II}$ are, if necessary, protected. The other symbols have the same meanings as the above-mentioned.), additionally, if necessary, by subjecting to a deprotection reaction of protecting group.

The above-mentioned reduction reaction is known, for example, it can be performed under the reductant (borane.tetrahydrofuran complex, borane.dimethylsulfide complex, diborane, etc.) and asymmetry induced agent ((R)-2-methyl-CBS-oxazaborolidine, (S)-2-methyl-CBS-oxazaborolidine, etc.), in organic solvents (tetrahydrofuran, dimethoxyethane, toluene, methylene chloride, diethylether, 1,4-dioxane, etc.) at the temperature of –20 to 50° C.

The deprotection reaction of a protective group for carboxyl, hydroxyl, amino, or mercapto is known, and it includes;

(1) alkaline hydrolysis, (2) deprotection reaction under acidic conditions, (3) deprotection reaction by hydrogenolysis, (4) deprotection reaction of a silyl group, (5) deprotection reaction using metals, (6) deprotection reaction using metal complexes, and so on.

These methods are described concretely as follows.

(1) The deprotection reaction by alkaline hydrolysis is, for example, carried out in an organic solvent (e.g. methanol, tetrahydrofuran, or 1,4-dioxane, etc.) using a hydroxide of an alkali metal (e.g. sodium hydroxide, potassium hydroxide, or lithium hydroxide, etc.), a hydroxide alkaline earth metal (e.g. barium hydroxide, or calcium hydroxide, etc.), or a carbonate (e.g. sodium carbonate or potassium carbonate, etc.), or an aqueous solution thereof, or a mixture thereof at a temperature of 0 to 40° C.

(2) The deprotection reaction under acidic conditions is carried out, for example, in an organic solvent (e.g. methylene chloride, chloroform, 1,4-dioxane, ethyl acetate, or anisole, etc.) in the presence or absence of 2,2,2-trifluoroethanol in an organic acid (e.g. acetic acid, trifluoroacetic acid, methansulfonic acid, or p-tosylate, etc.), or an inorganic acid (e.g. hydrochloric acid, or sulfuric acid, etc.) or a mixture thereof (e.g. hydrogen bromide/acetic acid, etc.) at a temperature of 0 to 100° C.

(3) The deprotection reaction by hydrogenolysis is carried out, for example, in a solvent (e.g. ethers (e.g., tetrahydrofuran, 1,4-dioxane, dimethoxyethane, or diethylether, etc.), alcohols (e.g., methanol, or ethanol, etc.), benzenes (e.g. benzene, or toluene, etc.), ketones (e.g. acetone, or methylethylketone, etc.), nitriles (e.g. actetonitrile, etc.), amides (e.g., dimethylformamide, etc.), water, ethyl acetate, acetic acid, or a mixed solvent of at least two of these, etc.) in the presence of a catalyst (e.g. palladium-carbon, palladium black, palladium hydroxide-carbon, platinum oxide, or Raney nickel, etc.) under the hydrogen atmosphere at normal pressure or under pressurization, or in the presence of ammonium formate at a temperature of 0 to 200° C.

(4) The deprotection reaction of a silyl group is carried out, for example, in a water-miscible organic solvent (e.g. tetrahydrofuran, or acetonitrile, etc.) using tetrabutylammonium fluoride at a temperature of 0 to 40° C.

(5) The deprotection reaction using metals is carried out, for example, in an acidic solvent (e.g. acetic acid, pH4.2–7.2 buffer solution, or a mixture of a solution thereof and an organic solvent of tetrahydrofran, etc.) in the presence of zinc powder, if necessary sonicating, at the temperature of 0 to 40° C.

(6) The deprotection reaction using metal complexes is carried out, for example, in an organic solvent (e.g. methylene chloride, N,N-dimethylformamide, tetrahydrofran, ethyl acetate, acetonitrile, 1,4-dioxane, ethanol, etc.), water, or a mixture thereof, in the presence of a trap reagent (e.g. tributyltine hydride, triethylsilane, dimedone, morpholine, diethylamine, pyrrolidine, etc.), an organic acid (e.g. acetic acid, formic acid, 2-ethyl hexanoic acid, etc.) and/or salts of organic acid (e.g., sodium 2-ethylhexanoate, potassium 2-ethylhexanoate, etc.), in the presence or absence of a phosphine reagent (e.g. triphenylphosphine, etc.), using metal complexes (e.g. tetrakistriphenylphosphinepalladium (0), dichlorobis(triphenylphosphine)palladium(II), palladium acetate(II), tris(triphenylphosphine)rhodium(I) chloride, etc.) at the temperature of 0 to 40° C.

In addition, the deprotection reaction except the above-mentioned processes can be carried out, for example, by the process described in T. W. Greene, *Protective Groups in Organic Synthesis*, Wiley, New York, 1999.

The protection group for carboxyl includes, for example, methyl, ethyl, allyl, t-butyl, trichloroethyl, benzyl (Bn), phenacyl, p-methoxybenzyl, trytyl, 2-chlorotrytyl, or a solid phase carrier bound of a structure thereof and so on.

The protection group for hydroxyl includes, for example, methyl, trytyl, methoxymethyl (MOM), 1-ethoxyethyl (EE), methoxyethoxymethyl (MEM), 2-tetrahydropyranyl (THP), trimethylsyryl (TMS), triethylsyryl (TES), t-butyldimethylsyryl (TBDMS), t-butyldiphenylsyryl (TBDPS), acetyl (Ac), pivaloyl, benzoyl, benzyl (Bn), p-methoxybenzyl, allyloxycarbonyl (Alloc), 2,2,2-trichloroethoxycarbonyl (Troc), and so on.

The protection group of amino includes benzyloxycarbonyl, t-butoxycarbonyl, allyloxycarbonyl (Alloc), 1-methyl-1-(4-biphenyl)ethoxycarbonyl (Bpoc), trifluoroacetyl, 9-fluorenylmethoxycarbonyl, benzyl (Bn), p-methoxybenzyl, benzyloxymethyl (BOM), 2-(trimethylsyryl)ethoxymethyl (SEM) and so on.

The protection group of mercapto includes, for example, benzyl, methoxybenzyl, methoxymethyl (MOM), 2-tetrahydropyranyl (THP), diphenylmethyl, acetyl (Ac) and so on.

The protective group for carboxyl, hydroxyl, amino or mercapto is not particularly limited to the above mentioned groups, so long as it can be easily and selectively left. For example, those described in T. W. Greene, *Protective Groups in Organic Synthesis*, Wiley, New York, 1999 can be used.

As is easily understood by those skilled in the art, an object compound of the present invention can be produced easily by using a different deprotection reaction depending on usage.

[2] Among the compounds represented by formula (I), the compound 13–14 position of which is a single bond, i.e. the compound represented by formula (I-B)

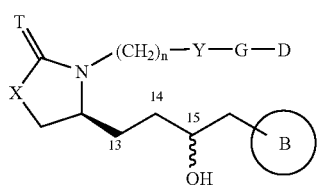

(I-B)

(wherein, all the symbols have the same meanings as the above-mentioned.) can be prepared by the following processes.

The compound represented by formula (I-B) can be prepared by subjecting to a hydrogenation reaction a compound represented by formula (III),

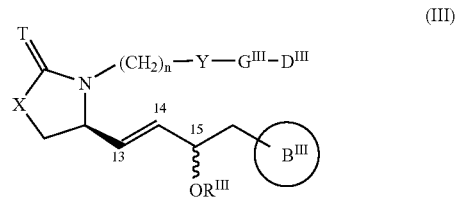

(III)

(wherein, $B^{III}$, $D^{III}$ and $G^{III}$ have the same meanings as that of B, D and G, but carboxyl, hydroxyl, amino and mercapto included the group represented by $B^{III}$, $D^{III}$ and $G^{III}$ are, if necessary, protected. $R^{III}$ is a hydrogen atom or protection group of hydroxyl. The other symbols have the same meanings as the above-mentioned.), additionally, if necessary, by subjecting to a deprotection reaction of protecting group.

The hydrogenation reaction is known, for example, it can be performed in organic solvents (ethers(e.g. tetrahydrofuran, 1,4-dioxane dimethoxyethane, diethylether, etc.), alcohols (e.g. methanol, ethanol, etc.), benzenes (e.g. benzene, toluene, etc.), ketones (e.g. acetone, methylethylketone, etc.), nitriles (e.g. acetonitrile, etc.), amides (e.g. N,N-dimethylformamide, etc.) in the presence of a catalyst (e.g. palladium-carbon, palladium black, palladium hydroxide, platinum oxide, or Raney nickel, etc.), under the hydrogen atmosphere at normal pressure or under pressurization, or in the presence of ammonium formate at a temperature of 0 to 200° C.

The deprotection reaction of protection group can be carried out by the same method as that of the above-mentioned.

[3] Among the compounds represented by formula (I), the compound is that T is an oxygen atom and X is —CH$_2$—, i.e. the compound represented by formula (I-C)

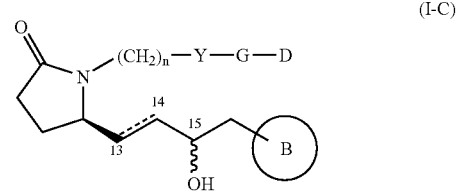

(I-C)

(wherein, all the symbols have the same meanings as the above-mentioned.) can be prepared by the following processes.

The compound represented by formula (I-C) can be prepared by subjecting to a reductive amination reaction a compound represented by formula (IV),

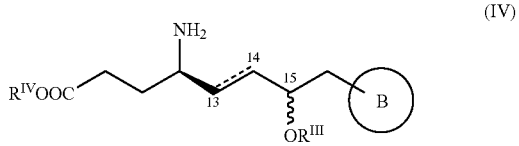

(IV)

(wherein, $R^{IV}$ is a protection group of carboxylic acid. The other symbols have the same meanings as the above-mentioned.) and the compound represented by formula (V),

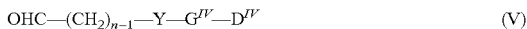

(wherein, $D^{IV}$ and $G^{IV}$ have the same meanings as the above-mentioned. And if necessary, carboxyl, hydroxyl, amino and mercapto included groups represented by $D^{IV}$ and $G^{IV}$ may be protected. The other symbols have the same meanings as the above-mentioned.), additionally, if necessary, by subjecting to a deprotection reaction of protecting group.

The reactive amination reaction is known, for example, it can be performed in organic solvents (e.g. ethyl acetate, dichloroethane, methylene chloride, N,N-dimethylformamido, tetrahydrofuran, acetic acid and the mixture thereof, etc.), in the presence of reductant (e.g. triacetoxy sodium boron hydride, sodium boron cyano hydride, sodium boron hydride, zinc boron hydride, diisobutylalminum hydride, etc.) at a temperature of −15 to 100° C., or in organic solvents (e.g. ethyl acetate, dichloroethane, methylene chloride, methanol, ethanol, acetic acid, etc.) in the presence of a catalyst (e.g. palladium-carbon, palladium black, palladium hydroxide, platinum oxide, or Raney nickel, etc.), under the hydrogen atmosphere at normal pressure or under pressurization at a temperature of 0 to 80° C.

The deprotection reaction of protection group can be carried out by the same method as that of the above-mentioned.

The compounds represented by formula (II), (III), (IV) and (V) used in the present invention are known in themselves, or can be easily prepared by known method, for example, the method described in *Comprehensive Organic Transformations: A Guide to Functional Group Preparations,* 2nd Edition, Richard C. Larock, Wiley & Sons Inc, 1999.

In each reaction in the present specification, as it is clear for those skilled in the art, a reaction with heat can be carried out using water bath, oil bath, sand bath, or microwave.

In each reaction in the present specification, a reaction may be carried out by using a solid-phase supported reagent supported in the high polymer (e.g. polystyrene, polyacrylamide, polypropylene, polyethyleneglycol, etc.).

In each reaction in the present specification, reaction products may be purified in an ordinary manner, for example, through normal-pressure or reduced-pressure distillation, or through high-performance liquid chromatography with silica gel or magnesium silicate, thin-layer chromatography, ion-exchange resin, scavenger resin or column chromatography, or through washing or recrystallization and so on. The purification may be effected in each reaction stage or after some reaction stages.

Toxicity:

Toxicity of the compound represented by formula (I), the salt thereof, the solvate thereof or cyclodextrin clathlate thereof, or the prodrug thereof is very low, and it is safe enough to use as a pharmaceutical agent.

INDUSTRIAL AVAILABILITY

Application to Pharmaceutical Preparations:

The compounds of the invention represented by formula (I) act on PGE receptor $EP_4$ subtype specifically and strongly and thus are considered useful for the prevention and/or treatment of immunological diseases (autoimmune diseases such as amyotrophic lateral sclerosis (ALS), multiple sclerosis, Sjoegren's syndrome, chronic rheumarthrosis and systemic lupus erythematosus, etc., and rejection after organ transplantation, etc.), asthma, neuronal cell death, arthritis, lung failure, pulmonary fibrosis, pulmonary emphysema, bronchitis, chronic obstructive pulmonary disease, liver damage, acute hepatitis, nephritis (acute nephritis, chronic nephritis), renal insufficiency, hypertension, myocardial ischemia, systemic inflammatory response syndrome, sepsis, hemophagous syndrome, macrophage activation syndrome, Still's disease, Kawasaki disease, burn, systemic granulomatosis, ulcerative colitis, Crohn's disease, hypercytokinemia at dialysis, multiple organ failure, shock and glaucoma and so on. It is also thought that $EP_4$ subtype receptor relates to protecting of mucosa. Therefore, the compounds which can bind on $EP_4$ subtype receptor are expected to be useful for the prevention and/or treatment of ulcer of gastrointestinal tract such as gastric ulcer and duodenal ulcer and so on, and stomatitis. It is also thought that $EP_4$ subtype receptor relates to hair growth function. Therefore, the compounds which can bind on $EP_4$ subtype receptor are expected to be useful for the prevention and/or treatment of hair-disadvantaged and alopecia. Furthermore, it is also thought that $EP_4$ subtype receptor relates to maturation of cervix. Therefore, the compounds which can bind on $EP_4$ subtype receptor are expected to be useful for the promoter of maturation of cervix.

Furthermore, the compounds which can bind on $EP_4$ subtype receptor also have an action of accelerating bone formation, so it is expected to be useful for the prevention and/or treatment of diseases associated with loss in bone mass, for example, 1) primary osteoporosis (e.g., primary osteoporosis followed by aging, postmenopausal primary osteoporosis, primary osteoporosis followed by ovariectomy, etc.), 2) secondary osteoporosis (e.g., glucocorticoid-induced osteoporosis, hyperthyroidism-induced osteoporosis, immobilization-induced osteoporosis, heparin-induced osteoporosis, immunosuppressive-induced osteoporosis, osteoporosis due to renal failure, inflammatory osteoporosis, osteoporosis followed by Cushing's syndrome, rheumatoid osteoporosis, etc.), and 3) bone diseases such as bone metastasis of cancer, hypercalcemia, Paget's disease, bone loss (alveolar bone loss, mandibular bone loss, childhood idiopathic bone loss, etc.), osteonecrosis, etc. Besides treatment of the above diseases, the present invention also includes a pharmaceutical composition for accelerating bone formation after bone operation (e.g., bone formation after fractures, bone formation after bone grafting, bone formation after operation of artificial joint, bone formation after spinal fusion and bone formation after the other operation for bone regeneration, etc.), or promoting treatment thereof, or alternative treatment for bone grafting.

It is also thought that $EP_4$ subtype receptor relates to induction of physiological sleeping and suppression of blood platelet aggregation, the compounds which can bind on EP4 receptor selectively are expected to be useful for the prevention and/or treatment of sleep disorder and thrombosis.

The compound which can bind on $EP_4$ receptor selectively do not have inducing pain which may be caused by $EP_1$ and uterine contraction which may be caused by $EP_3$, so they are thought to be agents having no effect on the above actions.

Among the compounds represented by formula (I) are those which bind $EP_4$ receptor as well as $EP_2$ receptor. The compound which binds on $EP_2$ receptor is considered useful for the prevention and/or treatment of immunological diseases (autoimmune diseases such as amyotrophic lateral sclerosis (ALS), multiple sclerosis, Sjoegren's syndrome, chronic rheumarthrosis and systemic lupus erythematosus, etc., and rejection after organ transplantation, etc.), asthma, neuronal cell death, premature birth, miscarriage, pars nervosa retinae trouble such a glaucoma, erectile dysfunction, arthritis, lung failure, pulmonary fibrosis, pulmonary emphysema, bronchitis, chronic obstructive pulmonary disease, liver damage, acute hepatitis, shock, nephritis, renal insufficiency, circulatory system disorder (e.g., hypertension, myocardial ischemia, chronic arterial obstruction, vibration disease), systemic inflammatory response syndrome, sepsis, hemophagous syndrome, macrophage activation syndrome, Still's disease, Kawasaki disease, burn, systemic granulomatosis, ulcerative colitis, Crohn's disease, hypercytokinemia at dialysis, multiple organ failure and bone disease (e.g., fracture, refracture, intractable fracture, bone union insufficiency, pseudarthrosis, osteomalacia, bone Paget's disease, spondylism, transfer of cancer to bone, osteroarthritis, destruction of bone/cartilage due to these analogous diseases, etc.) and so on. The compound which binds on $EP_2$ receptor is also considered useful as an agent for accelerating the osteogenesis/treatment after bone surgery (e.g., osteogenesis after fracture, osteogenesis after bone graft, osteogenesis after artificial arthrogenesis, osteogenesis after spinal fusion, osteogenesis after surgery for such as, multiple myeloma, lung cancer, breast cancer, etc., osteogenesis after other bone repair, etc.) or substitute for bone transfer. This compound is further considered useful as an agent for accelerating the regeneration of peridontium in peridontium disease.

The compound which binds to both $EP_4$ receptor and $EP_2$ receptor can be expected to exert an additive or synergistic effect on diseases related to both the receptors.

The compound represented by formula (I) or the salt thereof, the solvate thereof or the cyclodextrin clathlate thereof, or the prodrug thereof may be administered in combination with other pharmaceutical preparations to accomplish the following purposes:

1) To compensate for and/or enhance the preventive and/or treatment effect of the compound to be combined;

2) To improve the kinetics/absorption of the compound to be combined and reduce the dose of the compound; and/or 3) To eliminate the side effect of the compound to be combined The compound represented by formula (I) and other pharmaceutical preparations may be administered in the form of formulation having these components incorporated in one preparation or may be administered in separate preparations. In the case where these pharmaceutical preparations are administered in separate preparations, they may be administered simultaneously or at different times. In the latter case, the compound represented by formula (I) may be administered before the other pharmaceutical preparations. Alternatively, the other pharmaceutical preparations may be administered before the compound represented by formula (I). The method for the administration of these pharmaceutical preparations may be the same or different.

The diseases on which the preventive and/or treatment effect of the above-mentioned combined preparations works are not specifically limited but may be those for which the preventive and/or treatment effect of the compound represented by formula (I) is compensated for and/or enhanced.

Examples of the other pharmaceutical preparations for compensating for and/or enhancing the preventive and/or treatment effect of the compound represented by formula (I) on bone diseases include phosphodiesterase-4 inhibitor, bisphosphonate preparation, vitamin D preparation, calcium adjuvant, estrogen preparation, calcitonin preparation, isoflavone-based preparation, anabolic steroid preparation, vitamin K preparation, cathepsin K inhibitor, prostaglandins, statin, parathyroid hormones, growth factors and so on.

Examples of the other pharmaceutical preparations for compensating for and/or enhancing the preventive and/or treatment effect of the compound represented by formula (I) on chronic obstructive pulmonary diseases and/or asthma include phosphodiesterase-4 inhibitor, steroids, $\beta_2$ adrenoreceptor stimulant, leukotriene receptor antagonist, thromboxane synthetase inhibitor, thromboxane $A_2$ receptor antagonist, mediator releasing inhibitor, antihistamines, xanthine derivatives, anticholinergic agent, cytokine inhibitor, prostaglandins, forskolin, elastase inhibitor, metalloproteinase inhibitor, expectorant, antibiotic and so on.

Examples of the other pharmaceutical preparations for compensating for and/or enhancing the preventive and/or treatment effect of the compound represented by formula (I) on arthritis or chronic articular rheumatism include metalloproteinase inhibitor, immunosuppressant, nonsteroidal antiinflammatory drugs (NSAID), steroids, phosphodiesterase-4 inhibitor and so on.

Examples of the other pharmaceutical preparations for compensating for and/or enhancing the preventive and/or treatment effect of the compound represented by formula (I) on erectile dysfunction include phosphodiesterase-5 inhibitor and so on.

Examples of the other pharmaceutical preparations for compensating for and/or enhancing the preventive and/or treatment effect of the compound represented by formula (I) on shock include elastase inhibitor and so on.

Examples of the other pharmaceutical preparations for compensating for and/or enhancing the preventive and/or treatment effect of the compound represented by formula (I) on colitis include NO synthase inhibitor, poly(ADP-ribose) polymerase inhibitor, phosphodiesterase-4 inhibitor, elastase inhibitor, interleukin-8 antagonist and so on.

Examples of the other pharmaceutical preparations for compensating for and/or enhancing the preventive and/or treatment effect of the compound represented by formula (I) on acute/chronic nephritis include steroids, phosphodiesterase-4 inhibitor, nonsteroidal antiinflammatory drugs, thromboxane $A_2$ receptor antagonist, leukotriene receptor antagonist, angiotensin II antagonist, angiotensin converting enzyme inhibitor, diuretic and so on.

Examples of the other pharmaceutical preparations for compensating for and/or enhancing the preventive and/or treatment effect of the compound represented by formula (I) on hypertension include calcium antagonist, angiotensin II antagonist, angiotensin converting enzyme inhibitor, phosphodiesterase-4 inhibitor, diuretic and so on.

Examples of the phosphodiesterase-4 inhibitor include rolipram, cilomilast (trade name: Ariflo), Bay 19-8004, NIK-616, cipamfylline (BGL-61063), atizolam (CP-80633), SCH-351591, YM-976, V-11294A, PD-168787, D-4386, IC-485 and so on.

Examples of the phosphodiesterase-5 inhibitor include sildenafil and so on.

Examples of the bisphonate preparation include sodium alendronate, disodium chlodronate, disodium pamidronate, disodium ethydronate, ivandronate, disodium incadronate, minodronate, olpadronate, sodium risedronate, tildronate, zoledronate and so on.

Examples of the calcitonin preparation include calcitonin, elcatonin and so on.

Examples of the prostaglandins (hereinafter abbreviated as "PG") include PG receptor agonist, PG receptor antagonist and so on.

Examples of PG receptor include PGE receptors ($EP_1$, $EP_2$, $EP_3$, and $EP_4$), PGD receptors (DP), PGF receptors (FP), PGI receptors (IP) and so on.

Examples of the steroids for external application include clobetasol propionate, diflorasone acetate, fluocinonide, mometasone furancarboxylate, betametasone dipropionate, betametasone butyropropionate, betametasone valerate, difluprednate, budesonide, diflucortolone valerate, amcinonide, halcinonide, dexamethasone, dexamethasone propionate, dexamethasone valerate, dexamethasone acetate, hydrocortisone acetate, hydrocortisone butyrate, hydrocortisone acetopropionate, deprodone propionate, prednisolone valeroacetate, fluocinolone acetonide, beclometasone propionate, triamcinolone acetonide, flumethasone pivalate, alclometasone propionate, clobetasone butyrate, prednisolone, beclometasone propionate, fludroxycortide and so on.

Examples of the steroids for internal use or injection include cortisone acetate, hydrocortisone, hydrocortisone sodium phosphate, hydrocortisone sodium succinate, fludrocortisone acetate, prednisolone, prednisolone acetate, prednisolone sodium succinate, prednisolone butylacetate, prednisolone sodium phosphate, halopredon acetate, methyl prednisolone, methyl prednisolone acetate, methyl prednisolone sodium succinate, triamicinolon, triamicinolon acetate, triamicinolon acetonide, dexamethasone, dexamethasone acetate, dexamethasone sodium phosphate, dexamethasone palmitate, paramethasone acetate, betametasone and so on.

Examples of the steroids as an inhalant include beclomethasone propionate, fluticasone propionate, budesonide, flunisolide, triamicinolon, ST-126P, ciclesonide, dexamethasone palomitionate, monometasone furancarbonate, prasterone sulfonate, deflazacort, methyl prednisolone sreptanate, methyl prednisolone sodium succinate and so on.

Examples of the $β_2$ adrenoreceptor stimulant include fenoterol hydrobromide, salbutamol sulfate, terbutaline sulfate, formoterol fumarate, salmeterol xinafoate, isoprotenol sulfate, orciprenalin sulfate, chloroprenalin sulfate, epinephrine, trimetoquinol hydrochloride, hexoprenalinmesyl sulfate, procaterol hydrochloride, tulobuterol hydrochloride, tulobuterol, pirbuterol hydrochloride, clenbuterol hydrochloride, mabuterol hydrochloride, ritodrine hydrochloride, bambuterol, dopexamin hydrochloride, meradrin tartrate, AR-C68397, levosalbutamol, R,R-formoterol, KUR-1246, KUL-7211, AR-C89855, S-1319 and so on.

Examples of the leukotriene receptor antagonist include pranlukast hydrate, montelukast, zafirlukast, seratrodast, MCC-847, KCA-757, CS-615, YM-158, L-740515, CP-195494, LM-1484, RS-635, A-93178, S-36496, BIIL-284, ONO-4057 and so on.

Examples of the thromboxane synthetase inhibitor include ozagrel hydrochloride, imitrodast sodium and so on.

Examples of the thromboxane $A_2$ receptor antagonist include seratrodast, ramatroban, domitroban calcium hydrate, KT-2-962 and so on.

Examples of the mediator releasing inhibitor include tranilast, sodium cromoglicate, anlexanox, repirinast, ibudilast, tazanolast, pemilolast potassium and so on.

Examples of the antihistamines include ketotifen fumarate, mequitazine, azelastine hydrochloride, oxatomide, terfenadine, emedastine fumarate, epinastine hydrochloride, astemizole, ebastin, cetirizine hydrochloride, bepotastine, fexofenadine, lolatadine, deslolatadine, olopatadine hydrochloride, TAK-427, ZCR-2060, NIP-530, mometasone furoate, mizolastine, BP-294, andolast, auranofin, acribastin and so on.

Examples of the xanthine derivatives include aminophylline, thoeophyline, doxophylline, cipamphilline, diprophilline and so on.

Examples of the anticholinergic agent include ipratropium bromide, oxitropium bromide, flutropium bromide, temiverine, tiotropium bromide, revatropate (UK-112166) and so on.

Examples of the cytokine inhibitor include suplatast tosilate (trade name: IPD) and so on.

Examples of the expectorant include foeniculated ammonia spirit, sodium hydrogen carbonate, bromhexine hydrochloride, carbocisteine, ambroxol hydrochloride, sustained release ambroxol hydrochloride, methylcysteine hydrochloride, acetyl cysteine, L-ethylcysteine hydrochloride, tyloxapol and so on.

Examples of the growth factors include fibroblast growth factor (FGF), vascular endothelium growth factor (VEGF), hepatocyte growth factor (HGF), insulin-like growth factor and so on.

Examples of the nonsteroid-based antiphlogistic include sasapyrine, sodium salicylate, aspirin, aspirin dialuminate formulation, diflunisal, indomethacin, suprofen, ufenamate, dimethylisopropyl azulen, bufexamac, felbinac, diclofenac, tolmetin sodium, clinoril, fenbufen, napmetone, proglumetacin, indomethacin farnesil, acemetacin, proglumetacin maleate, amfenac sodium, mofezolac, etodolac, ibuprofen, ibuprofen piconol, naproxen, flurbiprofen, flurbiprofen axethyl, ketoprofen, fenoprofen calcium, tiaprofen, oxaprozin, pranoprofen, loxoprofen sodium, aluminoprofen, zaltoprofen, mefenamic adid, aluminum mefenamate, tolfenamic acid, floctafenine, ketophenylbutazone, oxyfenbutazone, piroxicam, tenoxicam, anpiroxicam, napageln cream, epirizole, tiaramide hydrochloride, tinoridine hydrochloride, emorfazone, sulpryrine, Migrenin, Saridon, Sedes G, Amipylo N, Sorbon, pyrine system antipyretics, acetaminophen, phenacetin, dimethothiazine mesylate, simetride formulation, antipyrine system aphipyretics and so on.

Examples of the diuretic include mannitol, furosemide, acetazolamide, diclofenamide, matazolamide, trichlormethiazide, mefruside, spinolactone, aminophylline and so on.

The weight proportion of the compound represented by formula (I) and the other pharmaceutical preparations is not specifically limited.

Arbitrary two or more of the other pharmaceutical preparations may be administered in combination.

Examples of the other pharmaceutical preparations for compensating for and/or enhancing the preventive and/or treatment effect of the compound represented by formula (I) include not only those which have so far been found but also those which will be found on the basis of the above-mentioned mechanism.

In order to use the compound of the invention represented by formula (I) or the compound represented by formula (I) in combination with the other pharmaceutical preparations, these compounds are normally administered to the entire of human body or topically orally or parenterally.

The dose of these compounds depends on the age, weight and symptom of the patient, the remedial value, the administration method, the treatment time, etc. In practice, however, these compounds are administered orally once or several times per day each in an amount of from 1 ng to 100 mg per adult, parenterally once or several times per day each in an amount of from 0.1 ng to 10 mg per adult or continuously administered into vein for 1 hour to 24 hours per day.

It goes without saying that the dose of these compounds may be less than the above-mentioned value or may need to exceed the above-mentioned range because the dose varies under various conditions as mentioned above.

When the compounds of the invention represented by formula (I) or the compound represented by formula (I) is administered in combination with the other pharmaceutical preparations, they are used in the form of solid or liquid agent for oral administration, injection, agent for external application, suppository, eye drops or inhalant for parenteral administration or the like.

Examples of the solid agent for oral administration include tablet, pill, capsule, powder, and pellet. Examples of the capsule include hard capsule, and soft capsule.

In such a solid agent for internal application, one or more active materials are used in the form of preparation produced by an ordinary method singly or in admixture with a vehicle (e.g., lactose, mannitol, glucose, microcrystalline cellulose, starch, etc.), binder (e.g., hydroxypropyl cellulose, polyvinyl pyrrolidone, magnesium metasilicoaluminate, etc.), disintegrant (e.g., calcium fibrinoglycolate, etc.), glidant (e.g., magnesium stearate, etc.), stabilizer, dissolution aid (e.g., glutamic acid, aspartic acid, etc.) or the like. The solid agent may be coated with a coating agent (e.g., white sugar, gelatin, hydroxypropyl cellulose, hydroxypropyl methyl cellulose phthalate, etc.) or two or more layers. Alternatively, the solid agent may be capsulized by an absorbable material such as gelatin.

Examples of the liquid agent for oral administration include pharmaceutically acceptable aqueous solution, suspension, emulsion, syrup, and elixir. In such a liquid agent, one or more active agents are dissolved, suspended or emulsified in a commonly used diluent (e.g., purified water, ethanol, mixture thereof, etc.). Furthermore, such a liquid agent may comprise a wetting agent, a suspending agent, an emulsifier, a sweetening agent, a flavor, a preservative, a buffer, etc.

The agent for parenteral administration may be in the form of, e.g., ointment, gel, cream, wet compress, paste, liniment, nebula, inhalant, spray, aerosol, eye drops, collunarium or the like. These agents each contain one or more active materials and are prepared by any known method or commonly used formulation.

The ointment is prepared by any known or commonly used formulation. For example, one or more active materials are triturated or dissolved in a base to prepare such an ointment. The ointment base is selected from known or commonly used materials. In some detail, higher aliphatic acid or higher aliphatic acid ester (e.g., adipic acid, myristic acid, palmitic acid, stearic acid, oleic acid, adipic acid ester, myristic acid ester, palmitic acid ester, stearic acid ester, oleic acid ester, etc.), wax (e.g., beeswax, whale wax, ceresin, etc.), surface active agent (e.g., polyoxyethylenealkylether phosphoric acid ester, etc.), higher alcohol (e.g., cetanol, stearyl alcohol, setostearyl alcohol, etc.), silicon oil (e.g., dimethyl polysiloxane, etc.), hydrocarbon (e.g., hydrophilic petrolatum, white petrolatum, purified lanolin, liquid paraffin, etc.), glycol (e.g., ethylene glycol, diethylene glycol, propylene glycol, polyethylene glycol, macrogol, etc.), vegetable oil (e.g., castor oil, olive oil, sesame oil, turpentine oil), animal oil (mink oil, vitelline oil, squalane, squalene), water, absorption accelerator and rash preventive may be used singly or in admixture of two or more thereof. The base may further comprise a humectant, a preservative, a stabilizer, an antioxidant, a perfume, etc.

The gel is prepared by any known or commonly used formulation. For example, one or more active materials are dissolved in a base to prepare such a gel. The gel base is selected from known or commonly used materials. For example, lower alcohol (e.g., ethanol, isopropyl alcohol, etc.), gelling agent (e.g., carboxymethyl cellulose, hydroxyethyl cellulose, hydroxypropyl cellulose, ethyl cellulose, etc.), neutralizing agent (e.g., triethanolamine, diisopropanolamine, etc.), surface active agent (e.g., polyethylene glycol monostearate, etc.), gums, water, absorption accelerator, and rash preventive are used singly or in admixture of two or more thereof. The gel base may further comprise a preservative, an antioxidant, a perfume, etc.

The cream is prepared by any known or commonly used formulation. For example, one or more active materials are dissolved in a base to prepare such a cream. The cream base is selected from known or commonly used materials. For example, higher aliphatic acid ester, lower alcohol, hydrocarbon, polyvalent alcohol (e.g., propylene glycol, 1,3-butylene glycol, etc.), higher alcohol (e.g., 2-hexyl decanol, cetanol, etc.), emulsifier (e.g., polyoxyethylene alkyl ethers, aliphatic acid esters, etc.), water, absorption accelerator, and rash preventive are used singly or in admixture of two or more thereof. The cream base may further comprise a preservative, an antioxidant, a perfume, etc.

The wet compress is prepared by any known or commonly used formulation. For example, one or more active materials are dissolved in a base to prepare a kneaded mixture which is then spread over a support to prepare such a wet compress. The wet compress base is selected from known or commonly used materials. For example, thickening agent (e.g., polyacrylic acid, polyvinyl pyrrolidone, gum arabic, starch, gelatin, methyl cellulose, etc.), wetting agent (e.g., urea, glycerin, propylene glycol, etc.), filler (e.g., kaolin, zinc oxide, talc, calcium, magnesium, etc.), water, dissolution aid, tackifier, and rash preventive may be used singly or in admixture of two or more thereof. The wet compress base may further comprise a preservative, an antioxidant, a perfume, etc.

The pasting agent is prepared by any known or commonly used formulation. For example, one or more active materials are dissolved in a base to prepare a kneaded mixture which is then spread over a support to prepare such a pasting agent. The pasting agent base is selected from known or commonly used materials. For example, polymer base, fat and oil, higher aliphatic acid, tackifier and rash preventive may be used singly or in admixture of two or more thereof. The pasting agent base may further comprise a preservative, an antioxidant, a perfume, etc.

The liniment is prepared by any known or commonly used formulation. For example, one or more active materials are dissolved, suspended or emulsified in water, alcohol (e.g., ethanol, polyethylene glycol, etc.), higher aliphatic acid, glycerin, soap, emulsifier, suspending agent, etc., singly or in combination of two or more thereof, to prepare such a liniment. The liniment may further comprise a preservative, an antioxidant, a perfume, etc.

The nebula, inhalant, spray and aerosol each may comprise a commonly used diluent, additionally, a stabilizer such as sodium hydrogen sulfite and a buffer capable of providing isotonicity such as isotonic agent (e.g., sodium chloride, sodium citrate, or citric acid, etc.). For the process for the preparation of spray, reference can be made to U.S. Pat. Nos. 2,868,691 and 3,095,355.

The injection for parenteral administration consists of solid injection used to be dissolved or suspended in the form of solution, suspension, emulsion and a solvent to be dissolved before use. The injection is prepared by dissolving, suspending or emulsifying one or more active materials in a solvent. As such a solvent there may be used distilled water for injection, physiological saline, vegetable oil, alcohol such as propylene glycol, polyethylene glycol and ethanol, etc., singly or in combination thereof. The injection may further comprise a stabilizer, a dissolution aid (e.g., glutamic acid, aspartic acid, Polysolvate 80 (trade name), etc.), a suspending agent, an emulsifier, a soothing agent, a buffer, a preservative, etc. The injection is sterilized at the final step or prepared by an aseptic process. Alternatively, an aseptic solid agent such as freeze-dried product which has previously been prepared may be rendered aseptic or dissolved in an aseptic distilled water for injection or other solvents before use.

The eye drops for parenteral administration may be in the form of liquid, suspension, emulsion, formulation to be dissolved before use, or ointment or may be dissolved in a solvent in use.

These eye drops are prepared by any known method. For example, one or more active materials are dissolved, suspended or emulsified in a solvent. As such a solvent for eye drops there may be used sterilized purified water, physiological saline and other aqueous or nonaqueous solvents (e.g., vegetable oil, etc.), singly or in combination thereof. The eye drops may comprise an isotonic agent (e.g., sodium chloride, concentrated glycerin, etc.), a buffering agent (e.g., sodium phosphate, sodium acetate, etc.), a surface active agent (e.g., Polysolvate 80 (trade name), polyoxyl stearate 40, polyoxyethylene-hardened castor oil, etc.), a stabilizer (sodium citrate, sodium edentate, etc.), a preservative (e.g., benzalconium chloride, Paraben, etc.), etc. properly selectively as necessary. The eye drops are sterilized at the final step or prepared by an aseptic process. Alternatively, an aseptic solid agent such as freeze-dried product which has previously been prepared may be rendered aseptic or dissolved in aseptic distilled water for injection or other solvent before use.

The inhalant for parenteral administration may be in the form of aerosol, powder for inhalation or liquid for inhalation. The liquid for inhalation may be dissolved or suspended in water or other proper medium in use.

These inhalants are prepared by a known method.

For example, the liquid for inhalation is prepared from materials properly selected from preservatives (e.g., benzalconium chloride, Paraben, etc.), colorants, buffering agents (e.g., sodium phosphate, sodium acetate, etc.), isotonic agents (e.g., sodium chloride, concentrated glycerin, etc.), thickening agents (e.g., carboxyvinyl polymer, etc.), absorption accelerators, etc. as necessary.

The powder for inhalation is prepared from materials properly selected from glidants (e.g., stearic acid and salt thereof, etc.), binders (e.g., starch, dextrin, etc.), vehicles (e.g., lactose, cellulose, etc.), colorants, preservatives (e.g., benzalconium chloride, Paraben, etc.), absorption accelerators, etc., if necessary.

In order to administer the liquid for inhalation, a sprayer (e.g., atomizer, nebulizer, etc.) is normally used. In order to administer the powder for inhalation, a powder inhaler is normally used.

Other examples of the composition for parenteral administration include suppository for rectal administration and pessary for vaginal administration prepared by an ordinary formulation comprising one or more active materials.

[Local Application]

Referring to the local administration of the invention, $EP_4$ agonist may be locally administered to site of disease (particularly bone diseases involved in loss of bone mass). The form of $EP_4$ agonist is not limited to its administration method. $EP_4$ agonist may be in the form of injection, solid agent such as embedding agent; pellet and powder, ointment to be administered to intramuscular, subcutaneous, organic or articular site.

The sustained release formulation of the invention is not limited to its form so far as $EP_4$ agonist can be continuously administered to site of disease (particularly bone diseases involved in loss of bone mass). The sustained release formulation may be in the form of, e.g., sustained release injection (e.g., microcapsuled formulation, microspheric formulation, nanospheric formulation), embedding formulation (e.g., film-like formulation) or the like.

The microcapsuled formulation, microspheric formulation and nanospheric formulation of the invention each are a finely divided pharmaceutical composition with an biodegradable polymer comprising as active components the compound represented by formula (I) optionally in combination with other pharmaceutical preparations.

Examples of the biodegradable polymer of the invention include aliphatic acid ester polymers and copolymers thereof, polyacrylic acid esters, polyhydroxybutyric acids, polyalkylene oxalates, polyorthoesters, polycarbonates, and polyaminoacids. These compounds may be used singly or in admixture of two or more thereof. Examples of the aliphatic acid ester polymers and copolymers thereof include polylactic acid, polyglycolic acid, polycitric acid, polymalic acid, and lactic acid-glycolic acid copolymer. These compounds may be used singly or in admixture of two or more thereof. Besides these compounds, poly-α-cyanoacrylic acid esters, poly-β-hydroxybutyric acids, polytrimethyleneoxalates, polyorthoesters, polyorthocarbonates, polyethylene carbonates, poly-γ-benzyl-L-glutamic acids and poly-L-alanines may be used singly or in admixture of two or more thereof. Preferred among these compounds are polylactic acids, polyglycolic acids and lactic acid-glycolic acid copolymers, more preferably lactic acid-glycolic acid copolymers.

The average molecular weight of these biodegradable polymers to be used in the invention is preferably from about 2,000 to 800,000, more preferably from about 5,000 to 200,000. For example, the polylactic acid preferably has a weight-average molecular weight of from about 5,000 to 100,000, more preferably from about 6,000 to 50,000. The polylactic acid can be synthesized according to any known preparation method per se. In the lactic acid-glycolic acid copolymer, the composition ratio of the lactic acid to the glycolic acid is preferably from about 100/0 to 50/50 (w/w), particularly from about 90/10 to 50/50. The weight-average molecular weight of the lactic acid-glycolic acid copolymer is preferably from about 5,000 to 100,000, more preferably from about 10,000 to 80,000. The lactic acid-glycolic acid copolymer can be synthesized according to any known preparation method per se.

The term "weight-average molecular weight" as used herein is meant to indicate molecular weight in polystyrene equivalence determined by gel permeation chromatography (GPC).

The above-mentioned biodegradable polymer may be changed depending on the intensity of pharmacological activity of the compounds represented by formula (I) and the desired medicines to be released so far as the above-mentioned aims of the invention are accomplished. For example, the biodegradable polymer may be used in an amount of from about 0.2 to 10,000 times (by weight), preferably from about 1 to 1,000 times (by weight), more preferably from about 1 to 100 times (by weight) that of the physiologically active material.

Examples of the process for the preparation of microspheric, microcapsuled and nanospheric formulations include submerged drying method (e.g., o/w method, w/o/w method, etc.), phase separation method, spray drying method, granulation method by ultracritical fluid, and methods analogous thereto.

The submerged drying method (o/w method) and spray drying method will be further described hereinafter.

(1) In the submerged drying method (o/w method), a solution of a biodegradable polymer in an organic solvent is prepared at first. The organic solvent to be used in the preparation of the microspheric, microcapsuled and nanospheric formulations preferably has a boiling point of 120° C. or less. Examples of the organic solvent employable herein include halogenated hydrocarbons (e.g., methylene chloride, chloroform, etc.), aliphatic esters (e.g., ethyl acetate, etc.), ethers, aromatic hydrocarbons, and ketones (e.g., acetone, etc.). These compounds may be used in admixture of two or more at a proper ratio. Preferred among these organic solvents are methylene chloride and acetonitrile, particularly methylene chloride. The concentration of the biodegradable polymer in the organic solution depends on the molecular weight of the biodegradable polymer, the kind of the organic solvent, etc., but is normally predetermined to be from about 0.01 to 80% (v/w), preferably from about 0.1 to 70% (v/w), more preferably from about 1 to 60% (v/w).

The compound represented by formula (I) or is then added to and dissolved in the solution of the biodegradable polymer in an organic solvent thus obtained, optionally in combination with other pharmaceutical preparations. The amount of the compound represented by formula (i) to be added optionally in combination with the other pharmaceutical preparations depends on the kind of the pharmaceutical preparations to be added, the action of the pharmaceutical preparations in osteogenesis, the duration of the action, etc. but is normally from about 0.001% to 90% (w/w), preferably from about 0.01% to 80% (w/w), more preferably from about 0.3 to 30% (w/w) as calculated in terms of concentration in the solution of biodegradable polymer in an organic solvent.

Subsequently, the organic solution thus prepared is added to an aqueous phase which is then processed by an agitator, emulsifier or the like to form an o/w emulsion. The volume of the aqueous phase during this procedure is predetermined to be from about 1 to 10,000 times, preferably from about 2 to 5,000 times, particularly from about 5 to 2,000 times that of the oil phase. An emulsifier may be added to the aqueous phase which is an external phase. As such an emulsifier there may be normally used any material capable of forming a stable o/w emulsion. Examples of the emulsifier employable herein include anionic surface active agents, nonionic surface active agents, polyoxyethylene castor oil derivatives, polyvinyl pyrrolidone, polyvinyl alcohol, carboxymethyl cellulose, lecitine, and gelatin. These compounds may be used in proper combination. The concentration of the emulsifier in the external aqueous phase is preferably from about 0.001% to 20% (w/w), more preferably from about 0.01% to 10% (w/w), particularly from about 0.05% to 5% (w/w).

The evaporation of the solvent which is an oil phase can be accomplished by any commonly used method. In some detail, the evaporation of the solvent may be effected at ordinary pressure or gradually falling pressure with stirring by an agitator, magnetic stirrer or the like or may be effected while the pressure is being adjusted using a rotary evaporator. The microspheric formulation thus obtained is then fractionated by centrifugal separation or filtration. The microspheric formulation is washed with a surface active agent solution, alcohol or the like several times to remove the free compound represented by formula (I), optionally in combination with other pharmaceutical preparations, and the emulsifier from the surface thereof, again dispersed in distilled water or a dispersant containing a vehicle (e.g., mannitol, sorbitol, lactose, etc.), and then freeze-dried. In the above-mentioned o/w method, the microspheric formulation may be prepared by a method involving the dispersion of the compound represented by formula (I) in a solvent of a biodegradable polymer in an organic solvent, optionally in combination with other pharmaceutical preparations, i.e., s/o/w method.

(2) In order to prepare the microspheric formulation by the spray drying method, an organic solvent or emulsion having the biodegradable polymer and the compound represented by formula (I), optionally in combination with other pharmaceutical preparations, dissolved therein is sprayed into the drying chamber of a spray dryer apparatus (spray dryer) through a nozzle so that the organic solvent or water in the atomized droplets is evaporated in an extremely short period of time to prepare a microspheric formulation. Examples of the nozzle employable herein include two liquid nozzle, pressure nozzle, and rotary disc. It is useful to spray an organic solvent or an aqueous solution of an aggregation inhibitor (e.g., mannitol, lactose, gelatin, etc.) at the same time with the spray of o/w emulsion as necessary for the purpose of inhibiting the aggregation of microspheres. The microspheric formulation thus obtained is then put under reduced pressure optionally under heating to remove water and solvent more completely.

Examples of the film formulation include film material obtained by dissolving the above-mentioned biodegradable polymer and compound represented by formula (I), optionally in combination with other pharmaceutical preparations, in an organic solvent, and then subjecting the solution to evaporation to dryness and gelled material obtained by dissolving the above-mentioned biodegradable polymer and compound represented by formula (I), optionally in combination with other pharmaceutical preparations, in a proper solvent, and then adding a granulating agent (e.g., cellulose, polycarbonate, etc.) to the solution.

The microsphere, microcapsule and nanosphere of the invention may be used as they are. Alternatively, a spherical, rod-like, acicular, pelletized, film or cream pharmaceutical composition may be processed as a starting material to provide preparations in various forms.

Furthermore, this preparation may be used as a parenteral for local administration (e.g., injection such as intramuscular injection, subcutaneous injection, injection to organs, and injection to articular site, solid agent such as embedding agent, pellet and powder, liquid agent such as suspension, ointment, etc.). For example, in order to make an injection from the microspheric formulation, the microspheric formulation is suspended with a dispersant, a preservative, an isotonic agent, a buffer, a pH adjustor, etc. to make an aqueous suspension as a practical preparation for injection. Alternatively, the microspheric formulation may be dispersed with a vegetable oil optionally in admixture with a phospholipid such as lecitine or with a middle-chain aliphatic acid triglyceride (e.g., Mygliol-812) to make an oil suspension as an injection which can be practically used.

The particle diameter of the microspheric formulation may be arbitrary so far as it suffices the desired dispersibility and passage through syringe if the preparation is used as a suspension for injection. By way of example, the average particle diameter of the microspheric formulation is from about 0.1 to 300 μm, preferably from about 1 to 150 μm, more preferably from about 2 to 100 μm. The pharmaceutical composition of the invention is preferably in the form of suspension as above-mentioned. The pharmaceutical composition of the invention is also preferably in particulate form. This is because the pharmaceutical composition gives less excessive pain to patients when administered through a syringe for use in ordinary subcutaneous or intramuscular injection. It is particularly preferred that the pharmaceutical composition of the invention be in the form of injection. Examples of the method for rendering the microspheric formulation aseptic include method which is aseptic throughout the entire steps, method involving sterilization by gamma rays, and method involving the addition of preservative. However, the invention is not limited to these methods.

The pharmaceutical composition of the invention can be used for the treatment of bone diseases involved in loss of bone mass because the compound represented by formula (I), optionally in combination with other pharmaceutical preparations, can be gradually released normally for 1 week to 3 months, though depending on the kind and added amount of the biodegradable polymer. Among these bone disease treatments, particularly, the treatment of fracture often requires that the affected part be fixed and covered with a plaster bandage and the administration of pharmaceutical preparations be conducted only once rather than frequently. Accordingly, the pharmaceutical preparations thus administered are required to accelerate treatment continuously. Thus, the pharmaceutical composition of the invention is useful particularly in this treatment.

The dose of the pharmaceutical composition of the invention depends on the kind, content and form of the compound represented by formula (I), optionally in combination with other pharmaceutical preparations, the duration of release of pharmaceutical preparations, the animal to be administered, etc., but may be the effective amount of the compound represented by formula (I), optionally in combination with other pharmaceutical preparations. When administered to fracture as a microspheric formulation, for example, one time dose for adult (weight: 50 kg) is from about 0.001 mg to 500 mg, preferably from about 0.01 mg to 0.50 mg as calculated in terms of effective component. The pharmaceutical composition of the invention may be administered once 1 week to 3 months in the above-mentioned amount.

EFFECT OF THE INVENTION

The compounds of the present invention bind specifically to subtype EP4 receptor, hardly to the other subtype receptor such as EP1, EP3, etc. Therefore, they are thought to hardly have actions of inducing pain which may be caused by EP, and of uterine contraction which may be caused by $EP_3$. They have advantages of generating no side effects with those actions.

BEST MODE FOR CARRYING OUT THE INVENTION

The following Examples are intend to illustrate, but not to limit the present invention.

The solvents in parentheses at chromatographic separations section and TLC section show the developing or eluting solvents and the ratios of the solvents used are indicated by volume.

Without special explanation, NMR data was determined in $^1$H-NMR. And the solvents in parentheses show solvents used in determination, but in case of no description heavy chloroform used in determination.

All compounds described in the specification are named by organic chemistry nomenclature recommended by IUPAC, or by using of ACD/Name (Advanced Chemistry Development Inc.).

EXAMPLE 1

(4R,5E)-4-tert-butoxycarbonylamino-7-oxo-8-(3,5-dimethylphenyl)oct-5-enoic acid ethyl ester Under atmosphere of argon, a suspension of 60% sodium hydride (50 mg) was added by a solution of dimethyl (2-oxo-3-(3,5-dimethylphenyl)propyl)phosphonate (373 mg) in tetrahydrofuran (5 mL) at the temperature of 0° C. The mixture was stirred for an hour and then a solution of ethyl (4R)-4-(tert-butoxycarbonylamino)-4-formylbutanoate (298 mg) in tetrahydrofuran (5 mL) was added to the mixture. The mixture was stirred for an hour. To the mixture, metyl tert-butyl ether and water were added, and then 1N a solution of sodium hydroxide was added. The organic layer was washed with saturated brine, dried over an anhydrous magnesium sulfate, concentrated and was purified by column chromatography on silica gel (hexane:ethyl acetate=4:1) to give the title compound (300 mg) having the following physical data.

TLC: Rf 0.76 (hexane:ethyl acetate=1:1)

EXAMPLE 2

(4R,5E,7S)-4-tert-butoxycarbonylamino-7-hydroxy-8-(3,5-dimethylphenyl)oct-5-enoic acid ethyl ester Under atmosphere of argon, a solution of the compound prepared in Example 1 (295 mg) in tetrahydrofuran (7.3 mL) was added by 1.0 mol/l (R)-2-metyl-CBS-oxazaborolidine/toluene solution (0.22 mL) at the temperature of 0° C. Then 1.0 mol/l borane tetrahydrofuran complex/tetrahydrofuran solution was dropped to the mixture, and then the mixture was stirred for 45 minutes. Additionally, 1.0 mol/l (R)-2-methyl-CBS-oxazaborolidine/toluene solution (0.22 mL) and 1.0 mol/l borane tetrahydrofuran complex/tetrahydrofuran solution were dropped to the mixture and then the mixture was stirred for 20 minutes at a temperature of 0° C. To the mixture, small quantity of ethanol and water was added and raised till room temperature. The mixture was extracted with ethyl acetate. The organic layer was washed with diluted hydrochloric acid, saturated sodium bicarbonate water and saturated brine successively, dried over an anhydrous magnesium sulfate, concentrated and was purified by column chromatography on silica gel (hexane:ethyl acetate=from 4:1 to 3:1) to give the title compound (251 mg) having the following physical data.

TLC: Rf 0.59 (hexane:ethyl acetate=1:1);

NMR: δ 6.87, 6.82, 5.72, 5.57, 4.50, 4.33, 4.17–4.09, 2.79, 2.67, 2.32, 2.30, 1.90–1.63, 1.44, 1.26.

EXAMPLE 3

(4R,5E,7S)-4-amino-7-hydroxy-8-(3,5-dimethylphenyl)oct-5-enoic acid ethyl ester hydrochloride

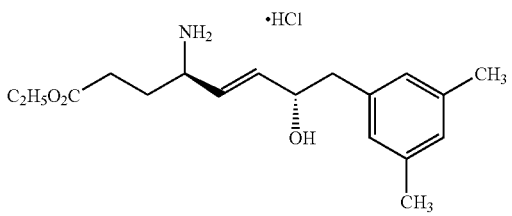

A solution of the compound prepared in Example 2 (243 mg) in ethanol (1 mL) was dropped by 4N hydrochloride/dioxane (0.5 mL) at a temperature of 0° C. and the mixture was stirred for 3 hours at room temperature. The mixture was concentrated to give the title compound (205 mg) having the following physical data. The compound was not purified any more and as is to be used in the next reaction.

TLC: Rf 0.29 (chloroform:methanol:acetic acid=9:1:0.1);
NMR: δ 6.83, 5.90, 5.54, 4.40–4.34, 4.14, 3.76–3.68, 2.82–2.67, 2.27, 2.26, 2.10–1.94, 1.85–1.72, 1.26

EXAMPLE 4

(15α,13E)-1,6-(1,4-interphenylene)-9-oxo-5-hydroxy-16-(3,5-dimethylphenyl)-2,3,4,5,17,18,19,20-octanol-8-azaprost-13-enoic acid methyl ester

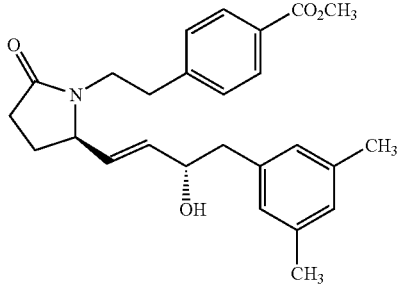

Under atmosphere of argon, a solution of the compound prepared in Example 3 (195 mg) in dry tetrahydrofuran (2 mL) was added by a solution of methyl (4-formylmethyl)benzoate (122 mg) in dry tetrahydrofuran (2 mL) and the mixture was stirred for an hour. To the mixture, triacetoxy sodium boron hydride (70 mg) was added and the mixture was stirred overnight at room temperature. The mixture was added by water and was extracted by ethyl acetate. The organic layer was washed with water and saturated brine successively, dried over an anhydrous magnesium sulfate, concentrated and was purified by column chromatography on silica gel (hexane:ethyl acetate=from 1:3 to 1:20) to give the title compound (136 mg) having the following physical data.

TLC: Rf 0.49 (ethyl acetate);
NMR: δ 7.96, 7.22, 6.89, 6.82, 5.62, 5.36, 4.34, 3.91, 3.77–3.69, 3.07–2.98, 2.93–2.70, 2.40–2.05, 2.29, 1.71–1.50, 1.26

EXAMPLE 5

(15α,13E)-1,6-(1,4-interphenylene)-9-oxo-15-hydroxy-16-(3,5-dimethylphenyl)-2,3,4,5,17,18,19,20-octanol-8-azaprost-13-enoic acid

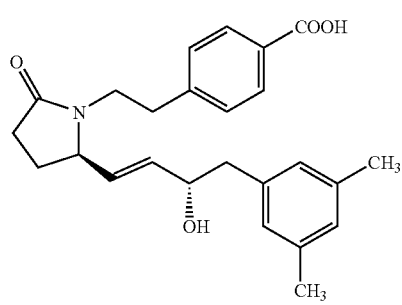

A mixed solution of the compound prepared in Example 4 (130 mg) in 1,2-dimethoxyethane (4 mL) and methanol (4 mL) was added by 2N sodium hydroxide solution and the mixture was stirred for an hour at room temperature. To the mixture, methyl tert-butyl ether was added and was extracted by 1N sodium hydroxide solution. The aqueous layer was acidic added by 2N hydrochloric acid and extracted by ethyl acetate. The layer of ethyl acetate was washed with saturated brine, dried over anhydrous magnesium sulfate, concentrated and was purified by column chromatography on silica gel (chloroform:methanol=from 100:1 to 20:1) to give the title compound (125 mg) having the following physical data.

TLC: Rf 0.31 (ethyl acetate);
NMR: δ 8.00, 7.24, 6.88, 6.82, 5.64, 5.38, 4.37, 3.82–3.70, 3.62, 3.10–3.01, 2.94–2.69, 2.40–2.25, 2.29, 2.18–2.06, 1.72–1.60

EXAMPLE 5(1)–5(26)

By the same procedure as described in Example 1, 2, 3, 4 and 5 using the corresponding phosphonate derivatives instead of dimethyl (2-oxo-4-(3,5-dimethylphenyl)butyl) phosphonate and the corresponding aldehyde derivatives instead of methyl (4-formylmethyl)benzoate, the following compound of the present invention were obtained.

EXAMPLE 5(1)

(15α,13E)-1,6-(1,4-interphenylene)-9-oxo-15-hydroxy-16-(3-(benzothiazol-2-yl)phenyl)-2,3,4,5,17,18,19,20-octanol-8-azaprost-13-enoic acid

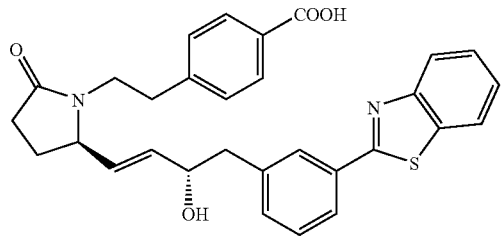

TLC: Rf 0.54 (chloform:methanol:acetic acid=9:1:0.1);
NMR: δ 8.18–7.86, 7.62–7.10, 5.61, 5.32, 4.46–4.40, 3.76–3.62, 3.07–2.98, 2.93, 2.87–2.75, 2.44–2.22, 2.14–2.02, 1.79, 1.67–1.55.

EXAMPLE 5(2)

(15α,13E)-1,6-(1,4-interphenylene)-9-oxo-15-hydroxy-16-(4-fulorophenyl)-2,3,4,5,17,18,1,9,20-octanol-8-azaprost-13-enoic acid

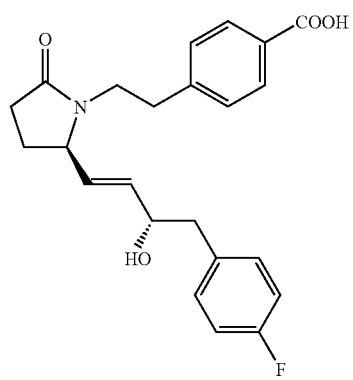

TLC: Rf 0.21 (chloroform:methanol=10:1);
NMR: δ 1.64, 2.11, 2.34, 2.83, 2.98, 3.75, 4.34, 5.35, 5.59, 6.97, 7.16, 7.24, 7.99.

EXAMPLE 5(3)

(15α,13E)-9-oxo-15-hydroxy-16-(3-(5-methylbenzothiazol-2-yl)phenyl)-5-(4-carboxythiazol-2-yl)-1,2,3,4,17,18,19,20-octanol-5-thia-8-azaprost-13-ene

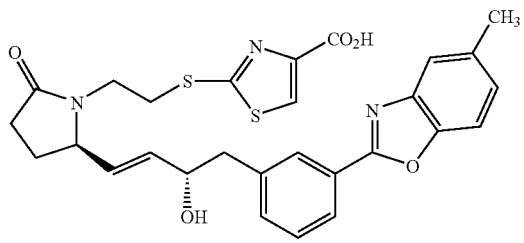

TLC: Rf 0.22 (chloroform:methanol=5:1);
NMR: δ 8.47, 8.14, 8.04, 7.65, 7.52–7.36, 7.21, 5.94, 5.81, 4.63, 4.17, 3.55–3.24, 3.00, 2.84, 2.51, 2.46–2.18, 1.81.

EXAMPLE 5(4)

(15α,13E)-1,6-(1,4-interphenylene)-9-oxo-15-hydroxy-16-(3-(5-methylbenzoxazol-2-yl)phenyl)-2,3,4,5,17,18,19,20-octanol-8-azaprost-13-enoic acid

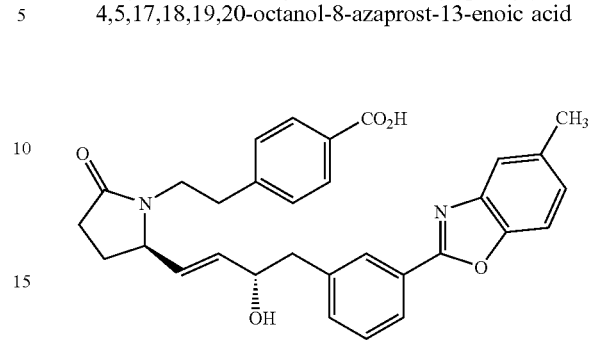

TLC: Rf 0.58 (chloroform:methanol=5:1);
NMR(DMSO-$d_6$): δ 8.05, 7.98, 7.81, 7.63, 7.57, 7.46, 7.25–7:18, 5.65, 5.29, 5.05, 4.29, 3.83, 3.46, 2.90–2.60, 2.43, 2.26–1.95, 1.51.

EXAMPLE 5(5)

(15α,13E)-9-oxo-15-hydroxy-16-(3-(6-methylbenzoxazol-2-yl)phenyl)-5-(4-carboxythiazol-2-yl)-1,2,3,4,17,18,19,20-octanol-5-thia-8-azaprost-13-ene

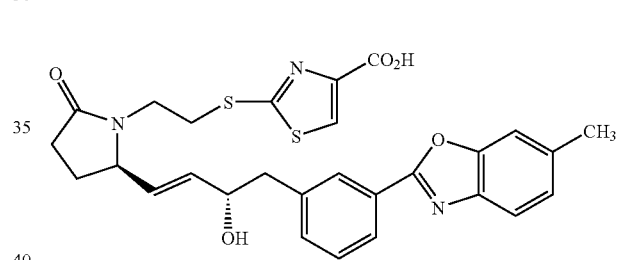

TLC: Rf 0.35 (chloroform:methanol:acetic acid=9:1:0.1);
NMR: δ 1.75, 2.33, 2.90, 3.34, 3.60, 4.19, 4.49, 5.62, 5.92, 7.20, 7.42, 7.66, 8.05, 8.20.

EXAMPLE 5(6)

(15α,13E)-1,6-(1,4-interphenylene)-9-oxo-15-hydroxy-16-(3-(6-methylbenzoxazol-2-yl)phenyl)-2,3,4,5,17,18,19,20-octanol-8-azaprost-13-enoic acid

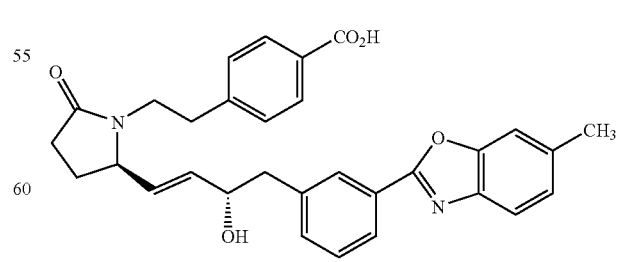

TLC: Rf 0.47 (chloroform:methanol:acetic acid=9:1:0.1);
NMR: δ 1.62, 2.21, 2.52, 2.85, 3.70, 4.42, 5.35, 5.62, 7.20, 7.42, 7.62, 7.95, 8.08.

EXAMPLE 5(7)

(15α,13E)-1,6-(1,4-interphenylene)-9-oxo-15-hydroxy-16-(3-(4-methylbenzothiazol-2-yl)phenyl)-2,3,4,5,17,18,19,20-octanol-8-azaprost-13-enoic acid

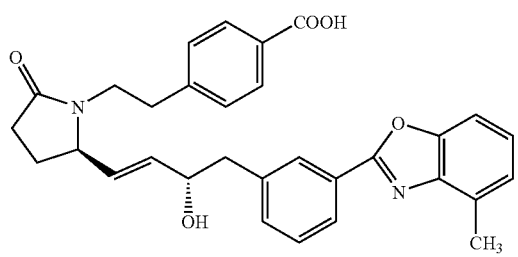

TLC: Rf 0.25 (chloroform:methanol=10:1);
NMR: δ 1.65, 2.10, 2.30, 2.67, 2.77, 2.95, 3.69, 4.43, 5.34, 5.62, 7.22, 7.41, 7.95, 8.11.

EXAMPLE 5(8)

(15α,13E)-9-oxo-15-hydroxy-16-(3-(4-methylbenzoxazol-2-yl)phenyl)-5-(4-carboxythiazol-2-yl)-1,2,3,4,17,18,19,20-octanol-5-thia-8-azaprost-13-ene

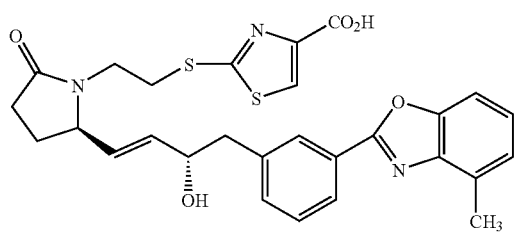

TLC: Rf 0.41 (chloroform:methanol=5:1);
NMR: δ 1.74, 2.24, 2.37, 2.68, 2.91, 3.29, 3.40, 3.63, 4.20, 4.43, 5.53, 5.88, 7.17, 7.27, 7.35, 7.44, 8.08, 8.16.

EXAMPLE 5(9)

(15α,13E)-1,6-(2-fuloro-1,4-interphenylene)-9-oxo-15-hydroxy-16-(3-methylphenyl)-2,3,4,5,17,18,19,20-octanol-8-azaprost-13-enoic acid

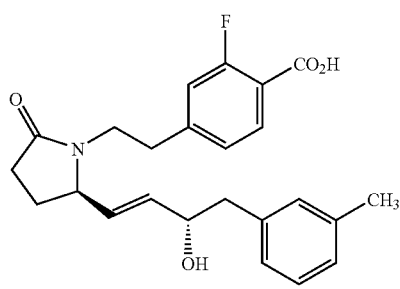

TLC: Rf 0.31 (chloroform:methanol=5:1);
NMR: δ 7.90, 7.19, 7.09–6.91, 5.67, 5.40, 4.40, 3.83, 3.71, 3.02, 2.90–2.73, 2.44–2.25, 2.33, 2.14, 1.67.

EXAMPLE 5(10)

(15α,13E)-1,6-(3-methyl-1,4-interphenylene)-9-oxo-15-hydroxy-16-(3-methylphenyl)-2,3,4,5,17,18,19,20-octanol-8-azaprost-13-enoic acid

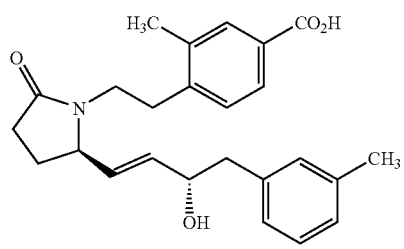

TLC: Rf 0.57 (chloroform:methanol=5:1);
NMR: δ 7.88, 7.84, 7.23–7.15, 7.07–6.97, 5.64, 5.41, 4.37, 3.81, 3.68, 3.06–2.71, 2.48–2.27, 2.38, 2.32, 2.15, 1.68.

EXAMPLE 5(11)

(15α,13E)-9-oxo-15-hydroxy-16-(3-(5,7-dimethylbenzoxazol-2-yl)phenyl)-5-(4-carboxythiazol-2-yl)-1,2,3,4,17,18,19,20-octanol-5-thia-8-azaprost-13-ene

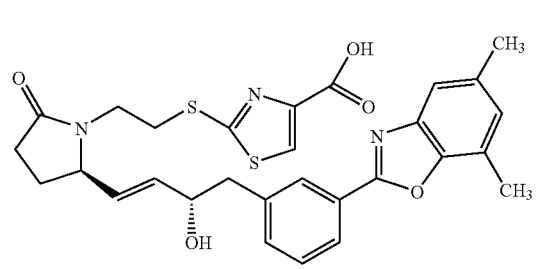

TLC: Rf 0.40 (chloroform:methanol:acetic acid=50:10:1);
NMR: δ 1.81, 2.39, 2.83, 3.01, 3.39, 4.15, 4.63, 5.81, 7.01, 7.42, 8.06, 8.14, 8.48.

EXAMPLE 5(12)

(15α,13E)-9-oxo-15-hydroxy-16-(3-(5-chlorobenzothiazol-2-yl)phenyl)-5-(4-carboxythiazol-2-yl)-1,2,3,4,17,18,19,20-octanol-5-thia-8-azaprost-13-ene

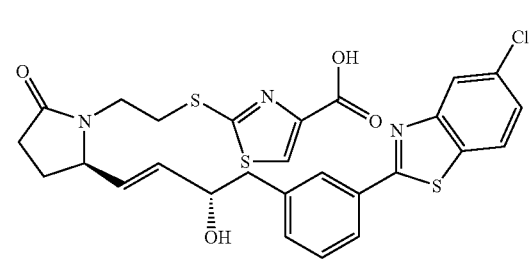

TLC: Rf 0.22 (chloroform:methanol:acetic acid=50:10:1);

NMR(DMSO-d$_6$): δ 1.55, 2.11, 2.83, 3.20, 3.55, 4.10, 4.25, 5.05, 5.33, 5.72, 7.45, 7.90, 8.15, 8.31.

EXAMPLE 5(13)

(15α,13E)-1,6-(1,4-interphenylene)-9-oxo-15-hydroxy-16-(3-(5-chlorobenzothiazol-2-yl)phenyl)-2,3,4,5,17,18,19,20-octanol-8-azaprost-13-enoic acid

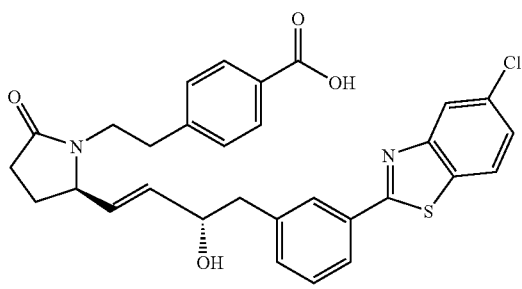

TLC: Rf 0.59 (chloroform:methanol:acetic acid=50:10:1);

NMR(DMSO-d$_6$): δ 1.52, 2.09, 2.73, 3.46, 3.85, 4.28, 5.06, 5.29, 5.66, 7.20, 7.43, 7.51, 7.81, 7.92, 8.11, 8.18.

EXAMPLE 5(14)

(15α)-9-oxo-15-hydroxy-16-(3-(2,4-dimethylphenyl)phenyl)-5-(4-carboxythiazol-2-yl)-1,2,3,4,17,18,19,20-octanol-5-thia-8-azaprost-13-ene

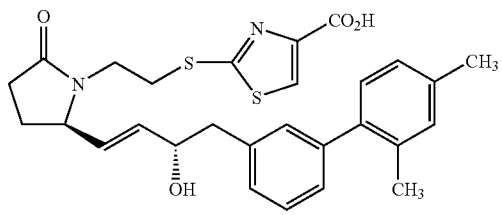

TLC: Rf 0.49 (chloroform:methanol=7:1);
NMR: δ 1.74, 2.23, 2.33, 2.36, 2.88, 3.24, 3.71, 4.12, 4.44, 5.53, 5.82, 7.15, 7.35, 8.07.

EXAMPLE 5(15)

(15α,13E)-9-oxo-15-hydroxy-16-(3-(3,4-dimethylphenyl)phenyl)-5-(4-carboxythiazol-2-yl)-1,2,3,4,17,18,19,20-octanol-5-thia-8-azaprost-13-ene

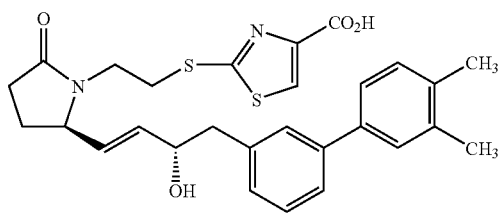

TLC: Rf 0.49 (chloroform:methanol=7:1);
NMR: δ 1.70, 2.30, 2.31, 2.33, 2.91, 3.13, 3.24, 3.68, 4.10, 4.46, 5.50, 5.82, 7.15, 7.40, 8.06.

EXAMPLE 5(16)

(15α,13E)-1,6-(1,4-interphenylene)-9-oxo-15-hydroxy-16-(3,4-difulorophenyl)-2,3,4,5,17,18,19,20-octanol-8-azaprost-13-enoic acid

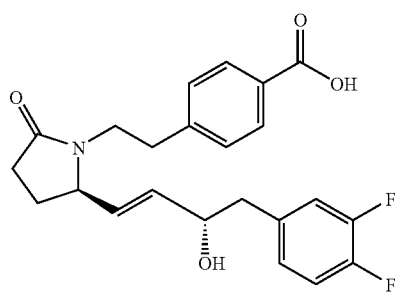

TLC: Rf 0.33 (ethyl acetate:methanol=10:1);
NMR(CD$_3$OD): δ 1.64, 2.23, 2.86, 3.65, 3.92, 4.29, 5.36, 5.64, 7.07, 7.28, 7.94.

EXAMPLE 5(17)

(15α,13E)-1,6-(2-methyl-1,4-interphenylene)-9-oxo-15-hydroxy-16-(3-methylphenyl)-2,3,4,5,17,18,19,20-octanol-8-azaprost-13-enoic acid

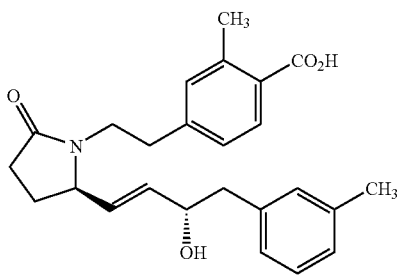

TLC: Rf 0.60 (chloroform:methanol=5:1);
NMR: δ 7.97, 7.19, 7.10–6.98, 5.63, 5.40, 4.39, 3.82–3.68, 3.00, 2.90–2.69, 2.62, 2.45–2.26, 2.32, 2.12, 1.67.

EXAMPLE 5(18)

(15α,13E)-9-oxo-15-hydroxy-16-(3-(5-chlorobenzoxazol-2-yl)phenyl)-5-(4-carboxythiazol-2-yl)-1,2,3,4,17,18,19,20-octanol-5-thia-8-azaprost-13-ene

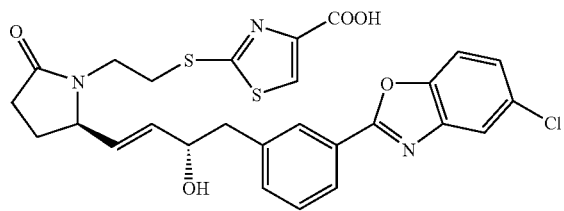

TLC: Rf 0.28 (chloroform:methanol=6:1);
NMR: δ 1.78, 2.34, 2.87, 2.99, 3.29, 3.45, 4.15, 4.60, 5.75, 5.93, 7.44, 7.83, 8.05, 8.12, 8.38.

EXAMPLE 5(19)

(15α,13E)-1,6-(1,4-interphenylene)-9-oxo-15-hydroxy-16-(3-methyl-4-fulorophenyl)-2,3,4,5,17,18,19,20-octanol-8-azaprost-13-enoic acid

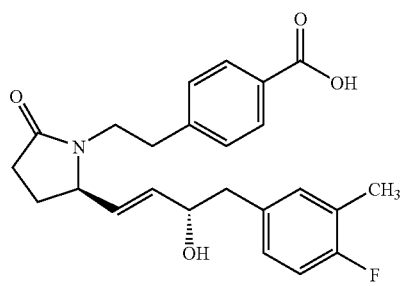

TLC: Rf 0.42 (chloroform:methanol=5:1);
NMR: δ 1.65, 2.24, 2.88, 3.77, 4.33, 5.38, 5.62, 6.96, 7.26, 8.01.

EXAMPLE 5(20)

(15α,13E)-1,6-(1,4-interphenylene)-9-oxo-15-hydroxy-16-(3-chloro-4-fulorophenyl)-2,3,4,5,17,18,19,20-octanol-8-azaprost-13-enoic acid

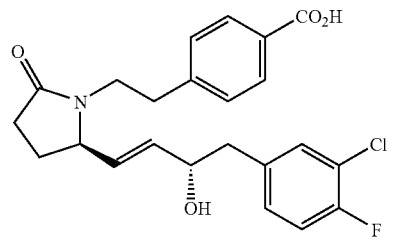

TLC: Rf 0.43 (chloroform:methanol=5:1);
NMR: δ 8.01, 7.29–7.23, 7.06, 5.60, 5.37, 4.36, 3.92–3.72, 3.06–2.71, 2.45–2.25, 2.12, 1.61.

EXAMPLE 5(21)

(15α,13E)-1,6-(3-methoxy-1,4-interphenylene)-9-oxo-15-hydroxy-16-(3-methylphenyl)-2,3,4,5,17,18,19,20-octanol-8-azaprost-13-enoic acid

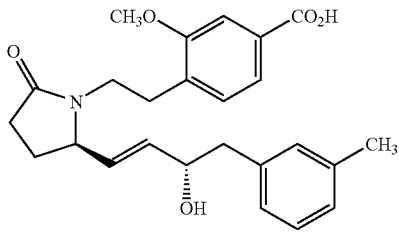

TLC: Rf 0.45 (chloroform:methanol=5:1);
NMR: δ 7.62, 7.53, 7.21–7.15, 7.08–6.96, 5.63, 5.40, 4.38, 3.88, 3.88–3.63, 3.04, 2.97–2.73, 2.43–2.25, 2.32, 2.11, 1.66.

EXAMPLE 5(22)

(15α,13E)-9-oxo-15-hydroxy-16-(3-trifuloromethoxyphenyl)-17,18,19,20-tetranol-5-thia-8-azaprost-13-enoic acid

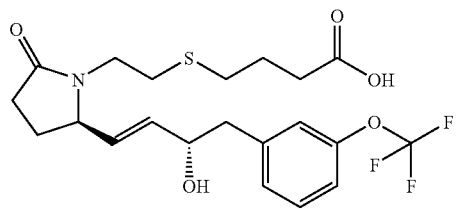

TLC: Rf 0.53 (chloroform:methanol=5:1);
NMR: δ 7.34, 7.17–7.07, 5.75, 5.52, 4.44, 4.12, 3.63, 2.97, 2.87, 2.67–2.33, 2.22, 1.98–1.82, 1.69.

EXAMPLE 5(23)

(15α,13E)-9-oxo-15-hydroxy-16-(3,5-difulorophenyl)-17,18,19,20-tetranol-5-thia-8-azaprost-13-enoic acid

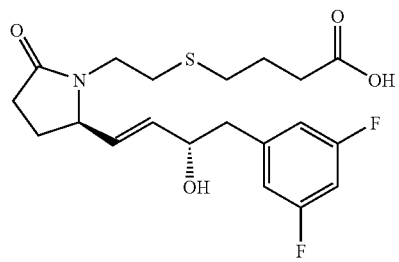

TLC: Rf 0.53 (chloroform:methanol=5:1);
NMR: δ 6.80–6.64, 5.75, 5.52, 4.43, 4.13, 3.64, 2.99, 2.87, 2.70–2.37, 2.23, 1.98–1.82, 1.70.

EXAMPLE 5(24)

(15α,13E)-9-oxo-15-hydroxy-16-(3-(phenyl)phenyl)-17,18,19,20-tetranol-5-thia-8-azaprost-13-enoic acid

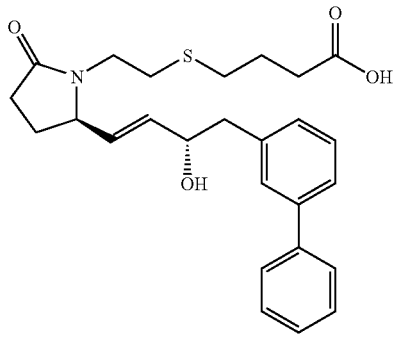

TLC: Rf 0.56 (chloroform:methanol=5:1);

NMR: δ 7.59–7.55, 7.49–7.33, 7.17, 5.76, 5.46, 4.45, 4.09, 3.57, 2.98–2.82, 2.61–2.26, 2.18, 1.92–1.78, 1.63.

EXAMPLE 5(25)

(15α,13E)-9-oxo-15-hydroxy-16-(3-(4-fulorophenyl)phenyl)-17,18,19,20-tetranol-5-thia-8-azaprost-13-enoic acid

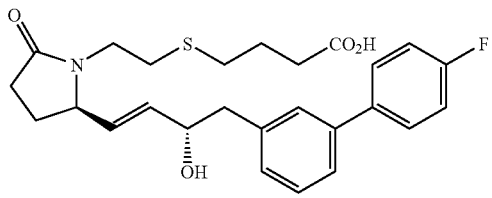

TLC: Rf 0.54 (chloroform:methanol=5:1);

NMR: δ 7.56–7.51, 7.45–7.35, 7.20–7.10, 5.78, 5.50, 4.47, 4.10, 3.59, 3.00–2.86, 2.61–2.30, 2.21, 1.97–1.80, 1.67.

EXAMPLE 5(26)

(15α,13E)-9-oxo-15-hydroxy-16-(3-phenyl-4-fulorophenyl)-17,18,19,20-tetranol-5-thia-8-azaprost-13-enoic acid

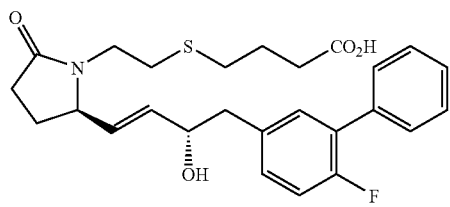

TLC: Rf 0.40 (chloroform:methanol=7:1);

NMR: δ 7.56–7.51, 7.48–7.34, 7.28, 7.18–7.06, 5.77, 5.51, 4.43, 4.11, 3.61, 2.95, 2.87, 2.61–2.33, 2.21, 1.95–1.78, 1.67.

EXAMPLE 6

(4R)-4-({[tert-butyl(dimethyl)silyl]oxy}metyl)-1,3-oxazolidine-2-one

Under atmosphere of argon, a solution of (4S)-4-(hydroxymethyl)-1,3-oxazolidine-2-one (34.1 g) in N,N-dimethylformamide (300 mL) was added by imidazole (25.7 g) and was cooled down to the temperature of 0° C. To the mixture, a solution of tert-butyldimethylsilylchloride (48.2 g) in N,N-dimethylformamide (300 mL) was moderately dropped and the mixture was stirred overnight at room temperature. The mixture was diluted with ethyl acetate and water and was washed with saturated brine. The organic layer was dried over an anhydrous magnesium sulfate and concentrated to give the title compound (64.8 g) having the following physical data, which was used for the next reaction without purification.

TLC: Rf 0.83 (ethyl acetate:methanol=20:1).

EXAMPLE 7

(4R)-4-({[tert-butyl(dimethyl)silyl]oxy}methyl)-3-(2-hydroxyethyl)-1,3-oxazolidine-2-one Under atmosphere of argon, a solution of the compound prepared in Example 6 (64.8 g) was dissolved in tetrahydrofuran (600 mL), cooled down to the temperature of 0° C. and the mixture was added by potassium tert-butoxide (39.2 g) and then was stirred for 30 minutes. The mixture was dropped by a solution of bromo ethyl acetate (38.7 mL) in tetrahydrofuran (50 mL), stirred for two hours at room temperature, diluted with ethyl acetate and water and washed with saturated brine. The organic layer was dried over an anhydrous magnesium sulfate and concentrated. Under atmosphere of argon, the solution of the obtained residue in tetrahydrofuran (200 mL) was dropped to a mixed solution of sodium boron hydride (22.0 g) in ethanol/tetrahydrofuran (400 mL/400 mL) at a temperature of 0° C. and the mixture was stirred for three hours at room temperature. The mixture was cooled in the iced water bath, added by saturated ammonium chloride solution and water and extracted by ethyl acetate. The organic layer was dried over an anhydrous magnesium sulfate and concentrated to give the title compound (70.9 g) having the following physical data, which was used for the next reaction without purification.

TLC: Rf 0.32 (hexane:ethyl acetate=1:2).

EXAMPLE 8

S-{2-[(4R)-4-({[tert-butyl(dimethyl)silyl]oxy}methyl)-2-oxo-1,3-oxazolidine-3-yl]ethyl}ethane thioate Under atmosphere of argon, a solution of the compound prepared in Example 7 (2.5 g) in tetrahydrofuran (200 mL) was cooled down, added by triethylamine (10.7 mL), methanesulfonylchloride (4.19 mL) and the mixture was stirred for 20 minutes. The mixture was added by methanol (1.10 mL), stirred for 30 minutes and then added by N,N-dimethylformamide (200 mL), potassium carbonate (12.6 g) and potassium thioacetic acid (10.4 g) and stirred for three hours at the temperature of 60° C. The mixture was cooled down to the room temperature, added by tert-butylmethylether (400 mL) and washed with water and saturated brine. The obtained organic layer was added by magnesium sulfate and activated carbon, filtrated, concentrated to give the title compound (16.0 g) having the following physical data, which was used for the next reaction without purification.

TLC: Rf 0.63 (hexane:ethyl acetate=1:1).

EXAMPLE 9 butyl 4-({2-[(4S)-4-({[tert-butyl(dimethyl)silyl]oxy}methyl)-2-oxo-1,3-oxazolidine-3-yl]ethyl}thio)butanoate Under atmosphere of argon, a solution of the compound prepared in Example 8 (16.0 g) in tetrahydrofuran (40 mL) was added by ethyl 4-bromobutanoate (7.83 mL), potassium tert-butoxide (6.17 g) and n-butanol (16.6 mL) and was stirred for three hours and a half at room temperature, for three hours at a temperature of 50° C., and additionally for an hour at a temperature of 80° C. The mixture was cooled down to the room temperature, added by tert-butyl methyl ether (400 mL) and washed with water and saturated brine. The organic layer was dried over an anhydrous magnesium sulfate, concentrated and the obtained residue was purified by column chromatography on silica gel (hexane:ethyl acetate=from 50:1 to 1:1). Under atmosphere of argon, a solution of the obtained compound in n-butanol (40 mL) was added by potassium carbonate (12.0 g), stirred overnight at the temperature of 100° C., cooled down to the room temperature and the mixture was diluted by ethyl acetate to be poured into water. The mixture was extracted by ethyl acetate and the obtained organic layer was washed with water and saturated brine. The organic layer was dried over magnesium sulfate and concentrated to give the title compound having the following physical data, which was used for the next reaction without purification.

TLC: Rf 0.72 (hexane:ethyl acetate=1:1).

EXAMPLE 10 butyl 4-({2-[(4S)-4-(hydroxymethyl)-2-oxo-1,3-oxazolidine-3-yl]ethyl}thio)butanoate Under atmosphere of argon, a solution of the compound prepared in Example 9 in tetrahydrofuran (85 mL) was dropped by 1M tetrabutylammonium fluoride in tetrahydrofuran solution (52 mL) and stirred for an hour at the room temperature. The mixture was added by saturated ammonium chloride solution, extracted by ethyl acetate and the obtained organic layer was washed with water and saturated brine. The organic layer was dried over magnesium sulfate, concentrated and purified by column chromatography on silica gel (hexane:ethyl acetate=1:1 to ethyl acetate) to give the title compound (11.9 g) having the following physical data.

TLC: Rf 0.08 (hexane:ethyl acetate=1:1).

EXAMPLE 11

(13E)-9,15-dioxo-16-(3-phenylphenyl)-17,18,19,20-tetranol-5-thia-8-aza-10-oxaprost-13-enoic acid.n-butylester Under atmosphere of argon, the compound purified in Example 10 (150 mg) was dissolved in ethyl acetate/dimethylsulfoxide (3 mL/2 mL) mixed solution, added by diisopropylethylamine (0.49 mL) and the mixture was cooled down to the temperature of 0° C. The mixture was added by sulfur trioxide.pyridine complex (224 mg), stirred for an hour and the mixture was added by 2N hydrochloric acid and ethyl acetate, extracted and washed with water, saturated sodium bicarbonate solution and saturated brine. The organic layer was dried over a sodium sulfate. Under atmosphere of argon, the obtained residue (150 mg) in acetonitrile solution (5 mL) was added by a suspended solution that a solution of dimethyl (3-biphenyl-3-yl-2-oxopropyl)phosphonate (179 mg) cooled down to the temperature of 0° C. in acetonitrile solution (6 mL) was added by diisopropylethylamine (0.098 mL) and lithium chloride (24 mg), stirred for an hour at the room temperature and prepared, and stirred for two hours. The mixture was added by water and 2N hydrochloric acid, extracted by ethyl acetate and washed with saturated sodium hydrocarbonate solution and saturated brine. The organic layer was dried over a magnesium sulfate, concentrated and purified by column chromatography on silica gel (hexane:ethyl acetate=1:1) to give the title compound (240 mg) having the following physical data.

TLC: Rf 0.32 (hexane:ethyl acetate=1:1).

EXAMPLE 12

(15α,13E)-9-oxo-15-hydroxy-16-(3-phenylphenyl)-17,18,19,20-tetranol-5-thia-8-aza-10-oxaprost-13-enoic acid n-butylester Under atmosphere of argon, a solution of the compound prepared in Example 11 (240 mg) in tetrahydrofuran (3 mL) was added by 1 mol/L (R)-2-methyl-CBS-oxazaborolidine in toluene solution (0.091 mL) at a temperature of 0° C. The mixture was dropped by 1 mol/L borane-tetrahydrofuran complex in tetrahydrofuran solution (0.36 mL) and stirred for an hour. To the mixture, 1N hydrochloric acid added and the mixture was extracted by ethyl acetate and washed with 1N hydrochloric acid, saturated sodium hydrocarbonate solution and saturated brine. The organic layer was dried over a magnesium sulfate, concentrated and purified by column chromatography (hexane:ethyl acetate=1:2) to give the title compound (96 mg) having the following physical data.

TLC: Rf 0.27 (hexane:ethyl acetate=1:2).

EXAMPLE 13

(15α,13E)-9-oxo-15-hydroxy-16-(3-phenylphenyl)-17,18,19,20-tetranol-5-thia-8-aza-10-oxaprost-13-enoic acid

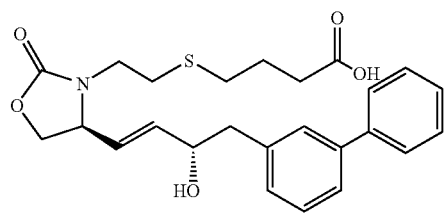

Under atmosphere of argon, a solution of the compound prepared in Example 12 (96 mg) in methanol (1 mL) was added by 2N sodium hydroxide solution (0.28 mL) and stirred for an hour at the room temperature. The mixture was added by 1N hydrochloric acid and extracted by ethyl acetate. The organic layer was washed with saturated brine, dried over an anhydrous sodium sulfate, concentrated and purified by column chromatography (chloroform: methanol=from 50:1 to 9:1) to give the title compound (75 mg) having the following physical data.

TLC: Rf 0.33 (methylene chloride:methanol=9:1);
NMR: δ 1.88, 2.50, 2.96, 3.40, 3.88, 4.34, 4.51, 5.55, 5.90, 7.17, 7.49.

EXAMPLE 13(1)–13(15)

By the same procedure as described in Example 11, 12 and 13 using the corresponding phosphate ester instead of dimethyl (3-biphenyl-3-yl-2-oxopropyl)phosphonate, the following compound of the present invention were obtained.

EXAMPLE 13(1)

(15α,13E)-9-oxo-15-hydroxy-16-(3-ethylphenyl)-17,18,19,20-tetranol-5-thia-8-aza-10-oxaprost-13-enoic acid TLC: Rf 0.45 (methylene chloride:methanol=9:1);
NMR: δ 1.24, 1.89, 2.65, 3.10, 3.45, 3.91, 4.40, 5.58, 5.90, 7.01, 7.11, 7.23.

EXAMPLE 13(2)

(15α,13E)-9-oxo-15-hydroxy-16-(3-chloro-4-fulorophenyl)-17,18,19,20-tetranol-5-thia-8-aza-10-oxaprost-13-enoic acid TLC: Rf 0.36 (methylene chloride:methanol=9:1);
NMR: δ 1.90, 2.65, 3.11, 3.47, 3.91, 4.38, 5.59, 5.88, 7.09, 7.23.

EXAMPLE 13(3)

(15α,13E)-9-oxo-15-hydroxy-16-(naphthalene-2-yl)-17,18,19,20-tetranol-5-thia-8-aza-10-oxaprost-13-enoic acid TLC: Rf 0.33 (methylene chloride:methanol=9:1);
NMR: δ 1.85, 2.50, 2.97, 3.34, 3.87, 4.34, 4.55, 5.54, 5.91, 7.32, 7.47, 7.64, 7.80.

EXAMPLE 13(4)

(15α,13E)-9-oxo-15-hydroxy-16-(3-trifuloromethoxyphenyl)-17,18,19,20-tetranol-5-thia-8-aza-10-oxaprost-13-enoic acid TLC: Rf 0.33 (methylene chloride:methanol=9:1);
NMR: δ 1.91, 2.57, 2.87, 3.10, 3.46, 3.89, 4.41, 5.59, 5.89, 7.11, 7.36.

EXAMPLE 13(5)

(15α,13E)-9-oxo-15-hydroxy-16-(4-fuloro-3-phenylphenyl)-17,18,19,20-tetranol-5-thia-8-aza-10-oxaprost-13-enoic acid TLC: Rf 0.42 (methylene chloride:methanol=9:1);
NMR: δ 1.87, 2.53, 2.87, 3.07, 3.44, 3.89, 4.40, 5.58, 5.90, 7.12, 7.26, 7.46.

EXAMPLE 13(6)

(15α,13E)-9-oxo-15-hydroxy-16-(4-fuloro-3-methylphenyl)-17,18,19,20-tetranol-5-thia-8-aza-10-oxaprost-13-enoic acid TLC: Rf 0.33 (methanol:chloroform=1:9);
NMR(CD$_3$OD): δ 1.86, 2.23, 2.40, 2.56, 2.71, 2.83, 2.96, 3.37, 3.91, 4.39, 5.45, 5.85, 6.95.

EXAMPLE 13(7)

(15α,13E)-9-oxo-15-hydroxy-16-(3,5-difulorophenyl)-17,18,19,20-tetranol-5-thia-8-aza-10-oxaprost-13-enoic acid TLC: Rf 0.30 (methanol:chloroform=1:9);
NMR: δ 1.91, 2.63, 3.10, 3.47, 3.91, 4.41, 5.60, 5.88, 6.72.

EXAMPLE 13(8)

(15α,13E)-9-oxo-15-hydroxy-16-(3-fulorophenyl)-17,18,19,20-tetranol-5-thia-8-aza-10-oxaprost-13-enoic acid TLC: Rf 0.30 (methanol:chloroform=1:9);
NMR: δ 1.93, 2.58, 2.86, 3.10, 3.44, 3.90, 4.41, 5.57, 5.88, 6.97, 7.30.

EXAMPLE 13(9)

(15α,13E)-9-oxo-15-hydroxy-16-(4-fuloro-3-trifuloromethylphenyl)-17,18,19,20-tetranol-5-thia-8-aza-10-oxaprost-13-enoic acid TLC: Rf 0.29 (methanol:chloroform=1:9);
NMR: δ 1.90, 2.68, 3.13, 3.48, 3.90, 4.41, 5.61, 5.90, 7.16, 7.41.

EXAMPLE 13(10)

(15α,13E)-9-oxo-15-hydroxy-16-(3-trifuloromethylphenyl)-17,18,19,20-tetranol-5-thia-8-aza-10-oxaprost-13-enoic acid TLC: Rf 0.30 (methanol:chloroform=1:9);
NMR: δ 1.90, 2.57, 2.92, 3.10, 3.46, 3.88, 4.42, 5.58, 5.90, 7.45.

EXAMPLE 13(11)

(15α,13E)-9-oxo-15-hydroxy-16-(3,4-difulorophenyl)-17,18,19,20-tetranol-5-thia-8-aza-10-oxaprost-13-enoic acid TLC: Rf 0.29 (methanol:chloroform=1:9);
NMR: δ 1.91, 2.64, 3.12, 3.48, 3.91, 4.40, 5.60, 5.88, 6.92, 7.09.

EXAMPLE 13(12)

(15α,13E)-9-oxo-15-hydroxy-16-phenyl-17,18,19,20-tetranol-5-thia-8-aza-10-oxaprost-13-enoic acid TLC: Rf 0.31 (methanol:chloroform=1:9); NMR: δ 1.90, 2.62, 3.06, 3.45, 3.89, 4.38, 5.55, 5.89, 7.28.

EXAMPLE 13(13)

(15α,13E)-9-oxo-15-hydroxy-16-(3-propylphenyl)-17,18,19,20-tetranol-5-thia-8-aza-10-oxaprost-13-enoic acid TLC: Rf 0.32 (methanol:chloroform=1:9);
NMR: δ 0.94, 1.63, 1.92, 2.62, 3.10, 3.45, 3.90, 4.39, 5.58, 5.90, 7.04, 7.22.

EXAMPLE 13(14)

(15α,13E)-9-oxo-15-hydroxy-16-(3-methoxymethylphenyl)-17,18,19,20-tetranol-5-thia-8-aza-10-oxaprost-13-enoic acid TLC: Rf 0.32 (methanol:chloroform=1:9);
NMR: δ 1:89, 2.58, 3.20, 3.39, 3.43, 3.92, 4.41, 4.47, 5.63, 5.92, 7.24.

EXAMPLE 13(15)

(15α,13E)-9-oxo-15-hydroxy-16-(3-ethyl-4-fulorophenyl)-17,18,19,20-tetranol-5-thia-8-aza-10-oxaprost-13-enoic acid TLC: Rf 0.30 (ethyl acetate);
NMR: δ 1.22, 1.89, 2.62, 3.13, 3.48, 3.92, 4.39, 5.60, 5.90, 6.98.

EXAMPLE 14(1)–14(5)

By the same procedure as described in Example 9, 10, 11, 12 and 13 using ethyl 2-bromo-1,3-thiazol-4-carboxylate instead of ethyl 4-bromobutanoate and the corresponding phosphate ester instead of dimethyl (3-biphenyl-3-yl-2-oxopropyl)phosphonate, the following compound of the present invention were obtained.

EXAMPLE 14(1)

(15α,13E)-9-oxo-15-hydroxy-16-phenyl-5-(4-carboxythiazol-2-yl)-1,2,3,4,17,18,19,20-octanol-5-thia-8-aza-10-oxaprost-13-ene

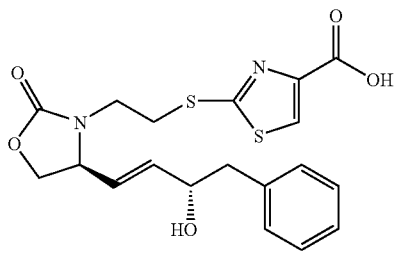

TLC: Rf 020 (chloroform:methanol=5:1);
NMR: δ 2.85, 3.30, 3.54, 3.92, 4.38, 5.53, 5.92, 7.24, 8.10.

EXAMPLE 14(2)

(15α,13E)-9-oxo-15-hydroxy-16-(3-methylphenyl)-5-(4-carboxythiazol-2-yl)-1,2,3,4,17,18,19,20-octanol-5-thia-8-aza-10-oxaprost-13-ene TLC: Rf 0.21 (chloroform:methanol=5:1);
NMR: δ 2.33, 2.80, 3.31, 3.57, 3.93, 4.40, 5.55, 5.92, 6.96, 7.06, 7.19, 8.10.

EXAMPLE 14(3)

(15α,13E)-9-oxo-15-hydroxy-16-(4-fulorophenyl)-5-(4-carboxythiazol-2-yl)-1,2,3,4,17,18,19,20-octanol-5-thia-8-aza-10-oxaprost-13-ene TLC: Rf 0.14 (chloroform:methanol=5:1);
NMR: δ 2.81, 3.35, 3.59, 3.93, 4.39, 5.57, 5.92, 6.99, 7.13, 8.11.

EXAMPLE 14(4)

(15α,13E)-9-oxo-15-hydroxy-16-(naphthalene-2-yl)-5-(4-carboxythiazol-2-yl)-1,2,3,4,17,18,19,20-octanol-5-thia-8-aza-10-oxaprost-13-ene TLC: Rf 0.26 (methylene:methanol=5:1);
NMR: δ 2.98, 3.38, 3.88, 4.33, 4.53, 5.51, 5.95, 7.30, 7.45, 7.60, 7.78, 8.05.

EXAMPLE 14(5)

(15α,13E)-9-oxo-15-hydroxy-16-(3-phenylphenyl)-5-(4-carboxythiazol-2-yl)-1,2,3,4,17,18,19,20-octanol-5-thia-8-aza-10-oxaprost-13-ene TLC: Rf 0.34 (methylene:methanol=5:1);
NMR: δ 2.27, 2.90, 3.26, 3.55, 3.91, 4.34, 4.49, 5.55, 5.95, 7.15, 7.46, 8.08.

EXAMPLE 15(1)–15(20)

By the same procedure as described in Example 6, 7, 8, 9, 10, 11, 12 and 13 using (5R)-5-(hydroxymethyl)pyrrolidine-2-one instead of (4S)-4-(hydroxymethyl)-1,3-oxazolidine-2-one, the corresponding bromoester instead of ethyl 4-bromobutanoate and the corresponding phosphate ester instead of dimethyl (3-biphenyl-3-yl-2-oxopropyl)phosphonate, the following compound of the present invention were obtained.

EXAMPLE 15(1)

(15α,13E)-9-oxo-15-hydroxy-16-(3-phenylphenyl)-5-(5-carboxythiophen-2-yl)-1,2,3,4,17,18,19,20-octanol-5-thia-8-azaprost-13-ene

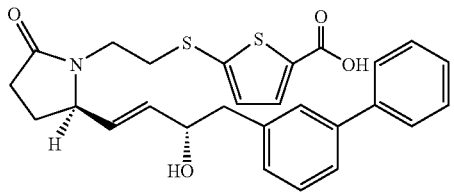

TLC: Rf 0.21 (chloroform:methanol=5:1);
NMR: δ 1.69, 2.19, 2.35, 2.89, 3.00, 3.61, 4.09, 4.43, 5.46, 5.73, 7.02, 7.16, 7.38, 7.56, 7.66.

EXAMPLE 15(2)

(15α,13E)-9-oxo-15-hydroxy-16-(naphthalene-2-yl)-5-(5-carboxythiophen-2-yl)-1,2,3,4,17,18,19,20-octanol-5-thia-8-azaprost-13-ene TLC: Rf 0.21 (chloroform:methanol=5:1);
NMR: δ 1.69, 2.19, 2.34, 2.92, 3.52, 4.05, 4.48, 5.44, 5.74, 7.02, 7.30, 7.44, 7.62, 7.66, 7.78.

EXAMPLE 15(3)

(15α,13E)-9-oxo-15-hydroxy-16-(4-fuloro-3-phenylphenyl)-5-(5-carboxythiophen-2-yl)-1,2,3,4,17,18,19,20-octanol-5-thia-8-azaprost-13-ene TLC: Rf 0.21 (chloroform:methanol=5:1);
NMR: δ 1.71, 2.16, 2.36, 2.81, 3.04, 3.66, 4.12, 4.38, 5.48, 5.73, 7.03, 7.10, 7.23, 7.41, 7.53, 7.66.

EXAMPLE 15(4)

(15α,13E)-9-oxo-15-hydroxy-16-(3-ethylphenyl)-5-(5-carboxythiophen-2-yl)-1,2,3,4,17,18,19,20-octanol-5-thia-8-azaprost-13-ene TLC: Rf 0.22 (chloroform:methanol=5:1);
NMR: δ 1.23, 1.73, 2.21, 2.38, 2.63, 2.78, 3.06, 3.67, 4.12, 4.39, 5.48, 5.73, 7.00, 7.08, 7.23, 7.69.

EXAMPLE 15(5)

(15α,13E)-9-oxo-15-hydroxy-16-(3-methylphenyl)-5-(carboxythiophen-2-yl)-1,2,3,4,17,18,19,20-octanol-5-thia-8-azaprost-13-ene TLC: Rf 0.21 (chloroform:methanol=5:1);
NMR: δ 1.72, 2.20, 2.33, 2.38, 2.77, 3.07, 3.66, 4.12, 4.38, 5.47, 5.72, 7.04, 7.19, 7.69.

EXAMPLE 15(6)

(15α,13E)-9-oxo-15-hydroxy-16-(3-trifuloromethoxyphenyl)-5-(5-carboxythiophen-2-yl)-1,2,3,4,17,18,19,20-octanol-5-thia-8-azaprost-13-ene TLC: Rf 0.21 (chloroform:methanol=5:1);
NMR: δ 1.72, 2.16, 2.38, 2.83, 3.08, 3.67, 4.12, 4.40, 5.50, 5.72, 7.09, 7.33, 7.69.

EXAMPLE 15(7)

(15α,13E)-9-oxo-15-hydroxy-16-(4-fuloro-3-phenylphenyl)-5-(4-carboxythiazol-2-yl)-1,2,3,4,17,18,19,20-octanol-5-thia-8-azaprost-13-ene TLC: Rf 0.21 (chloroform:methanol=5:1);
NMR: δ 1.73, 2.34, 2.86, 3.25, 3.74, 4.13, 4.44, 5.54, 5.82, 7.11, 7.26, 7.40, 7.53, 8.07.

EXAMPLE 15(8)

(15α,13E)-9-oxo-15-hydroxy-16-(3-ethylphenyl)-5-(4-carobxythiazol-2-yl)-1,2,3,4,17,18,19,20-octanol-5-thia-8-azaprost-13-ene TLC: Rf 0.21 (chloroform:methanol=5:1);
NMR: δ 1.22, 1.74, 2.31, 2.63, 2.82, 3.25, 3.72, 4.11, 4.42, 5.51, 5.81, 7.00, 7.08, 7.23, 8.08.

EXAMPLE 15(9)

(15α,13E)-9-oxo-15-hydroxy-16-(naphthalene-2-yl)-5-(4-carboxythiazol-2-yl)-1,2,3,4,17,18,19,20-octanol-5-thia-8-azaprost-13-ene TLC: Rf 0.21 (chloroform:methanol=5:1);
NMR: δ 1.72, 2.30, 3.11, 3.65, 4.11, 4.51, 5.50, 5.83, 7.31, 7.46, 7.63, 7.80, 8.05.

EXAMPLE 15(10)

(15α,13E)-9-oxo-15-hydroxy-16-(3-trifuloromethoxyphenyl)-5-(4-carboxythiazol-2-yl)-1,2,3,4,17,18,19,20-octanol-5-thia-8-azaprost-13-ene TLC: Rf 0.20 (chloroform:methanol=5:1);
NMR: δ 1.73, 2.33, 2.87, 3.27, 3.75, 4.12, 4.42, 5.55, 5.80, 7.11, 7.33, 8.09.

EXAMPLE 15(11)

(15α,13E)-9-oxo-15-hydroxy-16-(3-chloro-4-fulorophenyl)-5-(4-carboxythiazol-2-yl)-1,2,3,4,17,18,19,20-octanol-5-thia-8-azaprost-13-ene TLC: Rf 0.20 (chloroform:methanol=5:1);
NMR: δ 1.74, 2.34, 2.79, 3.32, 3.74, 4.12, 4.40, 5.54, 5.80, 7.06, 7.24, 8.10.

EXAMPLE 15(12)

(15α,13E)-9-oxo-15-hydroxy-16-cyclopropyl-5-(4-carboxythiazol-2-yl)-1,2,3,4,17,18,19,20-octanol-5-thia-8-azaprost-13-ene TLC: Rf 0.21 (chloroform:methanol=5:1);
NMR: δ 0.10, 0.50, 0.69, 1.46, 1.80, 2.35, 3.34, 3.47, 3.85, 4.13, 4.29, 5.60, 5.83, 8.10.

EXAMPLE 15(13)

(15α,13E)-9-oxo-15-hydroxy-16-cyclohexyl-5-(4-carboxythiazol-2-yl)-1,2,3,4,17,18,19,20-octanol-5-thia-8-azaprost-13-ene TLC: Rf 0.21 (chloroform:methanol=5:1);
NMR: δ 0.93, 1.35, 1.77, 2.33, 3.33, 3.46, 3.85, 4.14, 4.28, 5.55, 5.79, 8.10.

EXAMPLE 15(14)

(15α,13E)-9-oxo-15-hydroxy-16-(4-fulorophenyl)-5-(5-carboxythiazol-2-yl)-1,2,3,4,17,18,19,20-octanol-5-thia-8-azaprost-13-ene TLC: Rf 0.17 (methylene chloride:methanol:acetic acid=90:10:1);
NMR: δ 1.72, 2.31, 2.77, 3.32, 3.69, 4.13, 4.36, 4.70, 5.52, 5.76, 6.98, 7.15, 8.20.

EXAMPLE 15(15)

(15α,13E)-9-oxo-15-hydroxy-16-cyclobutyl-5-(4-carboxythiazol-2-yl)-1,2,3,4,17,18,19,20-octanol-5-thia-8-azaprost-13-ene TLC: Rf 0.31 (chloroform:methanol=5:1);
NMR: δ 1.72, 2.07, 2.39, 3.34, 3.48, 3.82, 4.12, 5.54, 5.76, 8.10.

EXAMPLE 15(16)

(15α,13E)-9-oxo-15-hydroxy-16-(4-chlorophenyl)-5-(4-carboxythiazol-2-yl)-1,2,3,4,17,18,19,20-octanol-5-thia-8-azaprost-13-ene TLC: Rf 0.42 (chloroform:methanol=4:1);
NMR: δ 1.72, 2.32, 2.80, 3.32, 3.72, 4.11, 4.39, 5.51, 5.78, 7.11, 7.30, 8.09.

EXAMPLE 15(17)

(15α,13E)-9-oxo-15-hydroxy-16-chlorophenyl-5-(4-carboxythiazol-2-yl)-1,2,3,4,17,18,19,20-octanol-5-thia-8-azaprost-13-ene TLC: Rf 0.52 (chloroform:methanol=4:1);
NMR: δ 1.50, 2.36, 3.43, 3.84, 4.18, 5.55, 5.78, 8.10.

EXAMPLE 15(18)

(15α,13E)-9-oxo-15-hydroxy-16-(indan-2-yl)-5-(4-carboxythiazol-2-yl)-1,2,3,4,17,18,19,20-octanol-5-thia-8-azaprost-13-ene TLC: Rf 0.39 (chloroform:methanol=9:1);
NMR: δ 1.75, 2.43, 3.25, 3.80, 4.14, 4.31, 5.61, 5.84, 7.15, 8.07.

EXAMPLE 15(19)

(15α,13E)-9-oxo-15-hydroxy-16-(tetrahydropyran-4-yl)-5-(4-carboxythiazol-2-yl)-1,2,3,4,17,18,19,20-octanol-5-thia-8-azaprost-13-ene TLC: Rf 0.13 (methylene chloride:methanol=5:1);
NMR: δ 1.52, 2.37, 3.42, 3.80, 3.96, 4.15, 4.30, 5.58, 5.82, 8.10.

EXAMPLE 15(20)

(15α,13E)-9-oxo-15-hydroxy-16-(7-methylnaphthalene-2-yl)-5-(4-carboxythiazol-2-yl)-1,2,3,4,17,18,19,20-octanol-5-thia-8-azaprost-13-ene TLC: Rf 0.34 (ethyl acetate);
NMR: δ 1.72, 2.33, 2.50, 3.23, 4.11, 4.51, 5.49, 5.82, 7.26, 7.54, 7.70, 7.74, 8.06.

EXAMPLE 16

(15α,13E)-9-oxo-15-hydroxy-16-(4-fulorophenyl)-17,18,19,20-tetranol-5,10-dithia-8-azaprost-13-enoic acid

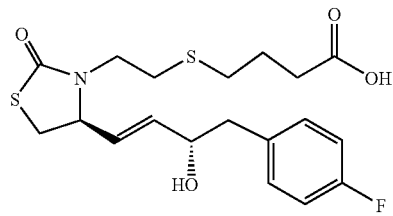

By the same procedure as described in Example 6, 7, 8, 9, 10, 11, 12 and 13 using (4S)-4-(hydroxymethyl)-1,3-thiazolidine-2-one instead of (4S)-4-(hydroxymethyl)-1,3-oxazolidine-2-one, dimethyl[3-(4-fulorophenyl)-2-oxopropyl]phosphonate instead of dimethyl (3-biphenyl-3-yl-2-oxopropyl)phosphonate, the compound having the following physical data of the present invention were obtained.

TLC: Rf 0.22 (hexane:ethyl acetate=1:3);
NMR: δ 1.90, 2.56, 2.97, 3.39, 3.61, 4.38, 5.64, 5.84, 7.01, 7.17.

EXAMPLE 17 ethyl 5-({[(2R)-2-(hydroxymethyl)-5-oxopyrrolidine-1-yl]methyl}thio)pentanoate

Under atmosphere of argon, a solution of (5R)-5-({[tert-butyl(dimethyl)silyl]oxy}methyl)pyrrolidine-2-one (2 g) in benzene (20 mL) was added by p-toluene sulfonic acid monohydrate (166 mg) and paraformic aldehyde (290 mg) and stirred for an hour at the room temperature. The mixture was added by ethyl 5-mercaptopentanoate (1.41 g) and stirred heating using Dean-Stark apparatus for three hours at the temperature of 125° C. The mixture was diluted with tert-butylmethylether solution, washed with water and saturated brine, dried over an sodium sulfate, concentrated and purified by column chromatography on silica gel (ethyl acetate:hexane=1:6). Under atmosphere of argon, the purified compound (1.9 g) in tetrahyrdorfuran solution (1.5 mL) was added by 1M tetrabutylammonium fluoride in tetrahydrofuran (4.7 mL) and stirred for an hour at room temperature. The mixture was diluted with ethyl acetate and washed with water and saturated brine. The organic layer was dried over sodium sulfate, concentrated and purified by column chromatography on silica gel (ethyl acetate:hexane=1:2) to give the title compound (1.05 mg) having the following physical data.

TLC: Rf 0.81 (ethyl acetate).

EXAMPLE 18(1), 18(2)

By the same procedure as described in Example 11, 12 and 13 using the compound prepared in Example 17 instead of the compound prepared in Example 10, the corresponding phosphate ester instead of dimethyl (3-biphenyl-3-yl-2-oxopropyl)phosphonate, the following compound of the present invention were obtained.

EXAMPLE 18(1)

(15α,13E)-9-oxo-15-hydroxy-16-(4-fulorophenyl)-17,18,19,20-tetranol-6-thia-8-azaprost-13-enoic acid

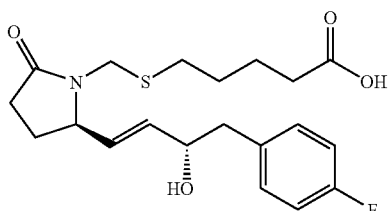

TLC: Rf 0.22 (methanol:chloroform=1:10);
NMR: δ 1.70, 2.39, 2.83, 3.48, 4.34, 4.90, 5.40, 5.78, 7.00, 7.15.

EXAMPLE 18(2)

(15α,13E)-9-oxo-15-hydroxy-16-(3-methylphenyl)-17,18,19,20-tetranol-6-thia-8-azaprost-13-enoic acid TLC: Rf 0.22 (methanol:chloroform=1:10);
NMR: δ 1.73, 2.38, 2.81, 3.45, 4.36, 4.89, 5.39, 5.79, 7.04, 7.20.

EXAMPLE 19

(15α,13E)-9-oxo-15-{[t-butyl(dimethyl)silyl]oxy}-16-(4-fulorophenyl)-17,18,19,20-tetranol-5-thia-8-azaprost-13-enoic acid.n-butyl ester Under atmosphere of argon, a solution of the butyl ester of the compound prepared in Example (3-1) of WO03/009872 (126 mg) in N,N-dimethylformamide (3 mL) was added by tert-butyldimethylsilylchloride (71 mg) and imidazole (32 mg) and stirred for an hour at the room temperature. The mixture was cooled down to the room temperature, poured into water and extracted by ethyl acetate. The obtained organic layer was washed with water and saturated brine, dried over sodium sulfate, concentrated and purified by column chromatography on silica gel (hexane:ethyl acetate=1:1) to give the title compound (158 mg) having the following physical data.

TLC: Rf 0.24 (hexane:ethyl acetate=1:1).

EXAMPLE 20

(15α,13E)-9-thioxo-15-{[t-butyl(dimethyl)silyl]oxy}-16-(4-fulorophenyl)-17,18,19,20-tetranol-5-thia-8-azaprost-13-enoic acid.n-butyl ester Under atmosphere of argon, a solution of the compound prepared in Example 19 in toluene (3 mL) was added by Lawesson reagent (68 mg) and stirred for 20 minutes at the temperature of 50° C. The mixture was cooled down to the room temperature, concentrated and the obtained residue was purified by column chromatography on silica gel (hexane:ethyl acetate=8:1) to give the title compound (146 mg) having the following physical data.

TLC: Rf 0.20 (hexane:ethyl acetate=4:1).

EXAMPLE 21

(15α,13E)-9-thioxo-15-hydroxy-16-(4-fulorophenyl)-17,18,19,20-tetranol-5-thia-8-azaprost-13-enoic acid

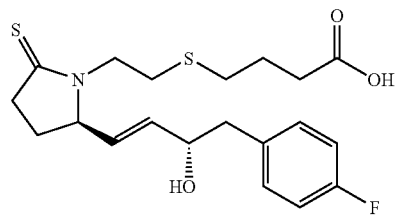

By the same procedure as described in Example 10 and 13 using the compound prepared in Example 20 instead of the compound prepared in Example 9, the following compound of the present invention were obtained.

TLC: Rf 0.44 (methylene chloride:methanol=9:1);
NMR: δ 1.75, 1.93, 2.28, 2.75, 3.35, 4.13, 4.44, 5.55, 5.79, 7.01, 7.17.

EXAMPLE 22(1)–22(12)

By the same procedure as described in Example 11, 12 and 13 using ethyl 4-({2-[(4S)-4-(hydroxymethyl)-2-oxo-1,3-thiazolidine-3-yl]ethyl}thio)butanoate instead of the compound prepared in Example 10 and the corresponding phosphate ester instead of dimethyl (3-biphenyl-3-yl-2-oxopropyl)phosphonate, the following compound of the present invention were obtained.

EXAMPLE 22(1)

4-[(2-{(4S)-4-[(1E,3S)-4-(3-ethylphenyl)-3-hydroxybut-1-enyl]-2-oxo-1,3-thiazolidine-3-yl}ethyl)sulfanil]butyric acid NMR: δ 1.23, 1.90, 2.55, 2.93, 3.39, 3.59, 4.33, 4.46, 5.67, 5.87, 7.06, 7.25;
MS(APCI, Neg. 20V):422 (M-H)$^-$;
TLC: Rf 0.43 (ethyl acetate).

EXAMPLE 22(2)

4-[(2-{(4S)-4-[(1E,3S)-3-hydroxy-4-phenylbut-1-enyl]-2-oxo-1,3-thiazolidine-3-yl}ethyl)sulfanil]butyric acid NMR: δ 1.90, 2.57, 2.96, 3.38, 3.59, 4.32, 4.46, 5.65, 5.86, 7.27;
MS(APCI, Neg. 20V):394 (M-H)$^-$;
TLC: Rf 0.45 (ethyl acetate).

EXAMPLE 22(3)

4-{[2-((4S)-4-{(1E,3S)-4-[4-fuloro-3-(trifuloromethyl)phenyl]-3-hydroxybut-1-enyl}-2-oxo-1,3-thiazolidine-3-yl)ethyl]sulfanyl}butyric acid NMR: δ 1.88, 2.57, 2.97, 3.41, 3.65, 4.40, 5.69, 5.85, 7.15, 7.43;
MS(APCI, Neg. 20V):480 (M-H)$^-$;
TLC: Rf 0.52 (ethyl acetate).

EXAMPLE 22(4)

4-[(2-{(4S)-4-[(1E,3S)-4-(3,5-difulorophenyl)-3-hydroxybut-1-enyl]-2-oxo-1,3-thiazolidine-3-yl}ethyl)sulfanyl]butyric acid NMR: δ 1.90, 2.57, 2.96, 3.41, 3.63, 4.41, 5.69, 5.84, 6.72;
MS(APCI, Neg. 20V):430 (M-H)$^-$;
TLC: Rf 0.58 (ethyl acetate).

EXAMPLE 22(5)

4-[(2-{(4S)-4-[1E,3S)-3-hydroxy-4-(3-propylphenyl)but-1-enyl]-2-oxo-1,3-thiazolidine-3-yl}ethyl)sulfanyl]butyric acid NMR: δ 0.94, 1.64, 1.90, 2.56, 2.94, 3.38, 3.60, 4.32, 4.46, 5.68, 5.87, 7.03, 7.24;
MS(APCI, Neg. 20V):436 (M-H)$^-$;
TLC: Rf 0.52 (ethyl acetate).

EXAMPLE 22(6)

4-[(2-{(4S)-4-[(1E,3S)-4-(3-ethyl-4-fulorophenyl)-3-hydroxybut-1-enyl]-2-oxo-1,3-thiazolidine-3-yl}ethyl)sulfanyl]butyric acid NMR: δ 1.22, 1.90, 2.57, 2.95, 3.39, 3.61, 4.32, 4.45, 5.68, 5.86, 6.99, 7.27;
MS(APCI, Neg. 20V):440 (M-H)$^-$;
TLC: Rf 0.55 (ethyl acetate).

EXAMPLE 22(7)

4-[(2-{(4S)-4-[(1E,3S)-4-(3,4-difulorophenyl)-3-hydroxybut-1-enyl]-2-oxo-1,3-thiazolidine-3-yl}ethyl)sulfanyl]butyric acid NMR: δ 1.91, 2.74, 3.41, 3.62, 4.39, 5.68, 5.84, 6.92, 7.07;
MS(APCI, Neg. 20V):430 (M-H)$^-$;
TLC: Rf 0.50 (ethyl acetate).

EXAMPLE 22(8)

4-{[2-((4S)-4-{(1E,3S)-3-hydroxy-4-[3-(trifuloromethyl)phenyl]but-1-enyl}-2-oxo-1,3-thiazolidine-3-yl)ethyl]sulfanyl}butyric acid NMR: δ 1.89, 2.75, 3.39, 3.61, 4.34, 4.49, 5.68, 5.85, 7.45;
MS(APCI, Neg. 20V):462 (M-H)$^-$;
TLC: Rf 0.50 (ethyl acetate).

EXAMPLE 22(9)

4-[(2-{(4S)-4-[(1E,3S)-4-(4-fuloro-3-methylphenyl)-3-hydroxybut-1-enyl]-2-oxo-1,3-thiazolidine-3-yl}ethyl)sulfanyl]butyric acid NMR: δ 1.91, 2.26, 2.74, 3.40, 3.62, 4.39, 5.67, 5.85, 6.96;
MS(APCI, Neg. 20V):426 (M-H)$^-$;
TLC: Rf 0.50 (ethyl acetate).

EXAMPLE 22(10)

4-[(2-{(4S)-4-[(1E,3S)-4-(3-fulorophenyl)-3-hydroxybut-1-enyl]-2-oxo-1,3-thiazolidine-3-yl}ethyl)sulfanyl]butyric acid NMR: δ 1.91, 2.74, 3.40, 3.61, 4.34, 4.47, 5.66, 5.85, 6.96, 7.28;
MS(APCI, Neg. 20V):412 (M-H)$^-$;
TLC: Rf 0.50 (ethyl acetate).

EXAMPLE 22(11)

4-[(2-{(4S)-4-[(1E,3S)-4-(3-chloro-4-fulorophenyl)-3-hydroxybut-1-enyl]-2-oxo-1,3-thiazolidine-3-yl}ethyl)sulfanyl]butyric acid NMR: δ 1.90, 2.67, 2.95, 3.04, 3.42, 3.63, 4.39, 5.66, 5.74, 5.83, 7.08, 7.26;
MS(APCI, Neg, 20V):446 (M-H)$^-$;
TLC: Rf 0.38 (hexane:ethyl acetate:methanol=25:75:2).

EXAMPLE 22(12)

4-{[2-((4S)-4-{(1E,3S)-3-hydroxy-4-[3-(methoxymethyl)phenyl]but-1-enyl}-2-oxo-1,3-thiazolidine-3-yl)ethyl]sulfanyl}butyric acid NMR: δ 1.88, 2.56, 2.86, 2.97, 3.07, 3.39, 3.42, 3.57, 4.32, 4.45, 4.46, 5.65, 5.67, 5.86, 7.13, 7.21, 7.29;
MS(APCI, Neg, 20V):438 (M-H)⁻;
TLC: Rf 0.35 (hexane:ethyl acetate:methanol=25:75:2).

EXAMPLE 23(1)–23(12)

By the same procedure as described in Example 11, 12 and 13 using butyl 7-[(2R)-2-(hydroxymethyl)-5-thioxo-1-pyrrolidinyl]heptanoate instead of the compound prepared in Example 10 and the corresponding phosphate ester instead of dimethyl (3-biphenyl-3-yl-2-oxopropyl)phosphonate, the following compound of the present invention were obtained.

EXAMPLE 23(1)

7-{(2R)-2-[(1E,3S)-4-(4-fulorophenyl)-3-hydroxybut-1-enyl]-5-thioxopyrrolidine-1-yl}heptanoic acid NMR: δ 1.33, 1.67, 2.28, 2.99, 4.06, 4.38, 5.53, 5.75, 7.00, 7.16;
MS(APCI, Neg. 20V):392 (M-H)⁻,
TLC: Rf 0.44 (chloroform:methanol=9:1).

EXAMPLE 23(2)

7-{(2R)-2-[(1E,3S)-4-(3,5-difulorophenyl)-3-hydroxybut-1-enyl]-5-thioxopyrrolidine-1-yl}heptanoic acid NMR: δ 1.34, 1.59, 1.78, 2.24, 2.35, 2.83, 3.04, 4.07, 4.39, 5.56, 5.76, 6.73;
MS(APCI, Neg. 20V):410 (M-H)⁻;
TLC: Rf 0.60 (ethyl acetate).

EXAMPLE 23(3)

7-((2R)-2-{(1E,3S)-4-[4-fuloro-3-(trifuloromethyl)phenyl]-3-hydroxybut-1-enyl}-5-thioxopyrrolidine-1-yl)heptanoic acid NMR: δ 1.33, 1.58, 1.76, 2.23, 2.34, 2.91, 3.13, 4.06, 4.34, 4.44, 5.58, 5.77, 7.15, 7.42;
MS(APCI, Neg. 20V):460 (M-H)⁻;
TLC: Rf 0.61 (ethyl acetate).

EXAMPLE 23(4)

7-{(2R)-2-[(1E,3S)-4-(4-fuloro-3-methylphenyl)-3-hydroxybut-1-enyl]-5-thioxopyrrolidine NMR: δ 1.33, 1.61, 1.79, 2.23, 2.24, 2.35, 2.76, 2.99, 3.11, 4.07, 4.36, 5.76, 6.97;
MS(APCI, Neg. 20V):406 (M-H)⁻;
TLC: Rf 0.58 (ethyl acetate).

EXAMPLE 23(5)

7-{(2R)-2-[(1E,3S)-4-(3-ethyl-4-fulorophenyl)-3-hydroxybut-1-enyl)-5-thioxopyrrolidine-1-yl}heptanoic acid NMR: δ 1.22, 1.35, 1.60, 1.77, 2.23, 2.35, 2.74, 3.05, 4.06, 4.38, 5.56, 5.77, 6.97, 7.26;
MS(APCI, Neg. 20V):420 (M-H)⁻;
TLC: Rf 0.59 (ethyl acetate).

EXAMPLE 23(6)

7-((2R)-2-{(1E,3S)-3-hydroxy-4-[3-(trifuloromethyl)phenyl]but-1-enyl}-5-thioxopyrrolidine-1-yl)heptanoic acid NMR: δ 1.30, 1.68, 2.22, 2.34, 3.00, 4.05, 4.33, 4.48, 5.56, 5.78, 7.44;
MS(APCI, Neg. 20V):442 (M-H)⁻;
TLC: Rf 0.72 (ethyl acetate).

EXAMPLE 23(7)

7-{(2R)-2-[(1E,3S)-4-(3-fulorophenyl)-3-hydroxybut-1-enyl]-5-thioxopyrrolidine-1-yl}heptanoic acid NMR: δ 1.35, 1.70, 2.26, 2.35, 2.95, 4.07, 4.35, 4.43, 5.54, 5.76, 6.95, 7.28;
MS(APCI, Neg. 20V):392 (M-H)⁻;
TLC: Rf 0.70 (ethyl acetate).

EXAMPLE 23(8)

7-{(2R)-2-[(1E,3S)-3-hydroxy-4-phenylbut-1-enyl]-5-thioxopyrrolidine-1-yl}heptanoic acid NMR: δ 1.30, 1.68, 2.24, 2.35, 2.97, 4.07, 4.37, 5.53, 5.77, 7.27;
MS(APCI, Neg. 20V):374 (M-H)⁻;
TLC: Rf 0.69 (ethyl acetate).

EXAMPLE 23(9)

7-{(2R)-2-[(1E,3S)-4-(3,4-difulorophenyl)-3-hydroxybut-1-enyl]-5-thioxopyrrolidine 1-yl}heptanoic acid NMR: δ 1.33, 1.71, 2.28, 2.35, 2.95, 4.07, 4.36, 5.56, 5.76, 6.92, 7.07;
MS(APCI, Neg. 20V):410 (M-H)⁻;
TLC: Rf 0.70 (ethyl acetate).

EXAMPLE 23(10)

7-{(2R)-2-[(1E,3S)-4-(3-chloro-4-fulorophenyl)-3-hydroxybut-1-enyl]-5-thioxopyrrolidine-1-yl}heptanoic acid NMR: δ 1.35, 1.72, 2.25, 2.35, 2.80, 2.99, 3.10, 4.08, 4.38, 5.55, 5.75, 7.08, 7.25;
MS(APCI, Neg. 20V):426 (M-H)⁻;
TLC: Rf 0.61 (ethyl acetate).

EXAMPLE 23(11)

7-{(2R)-2-[(1E,3S)-4-(3-ethylphenyl)-3-hydroxybut-1-enyl]-5-thioxopyrrolidine 1-yl}heptanoic acid NMR: δ 1.24, 1.35, 1.70, 2.22, 2.34, 2.64, 2.93, 4.06, 4.36, 5.55, 5.79, 7.05, 7.24;
MS(APCI, Neg. 20V):402 (M-H)⁻;
TLC: Rf 0.63 (ethyl acetate).

EXAMPLE 23(12)

7-{(2R)-2-[(1E,3S)-3-hydroxy-4-(3-propylphenyl)but-1-enyl]-5-thioxopyrrolidine-1-yl}heptanoic acid NMR: δ 0.94, 1.35, 1.70, 2.23, 2.34, 2.57, 2.97, 4.06, 4.38, 5.55, 5.79, 7.04, 7.23;
MS(APCI, Neg. 20V):416 (M-H)⁻;
TLC: Rf 0.64 (ethyl acetate).

EXAMPLE 24

3-tert-butyl 4-methyl (4R)-2,2-dimethyl-1,3-oxazolidine-3,4-dicarboxylate

Under atmosphere of argon, D-serine.methylester (284 g) and di-tert-butyl di-carbonate (400 g) were dissolved in acetonitrile (2000 mL) and the mixture was added by triethylamine (255 mL) keeping the temperature inside from 6 to 1° C. under icing down and stirred for an hour and a half at room temperature. The mixture was filtrated to defecate triethylamine chloride and then the mother water was concentrated. The obtained residue was dissolved in ethyl acetate (1500 mL), washed with water (1000 mL) and saturated brine (1000 mL) and the organic layer was dried over a sodium sulfate, filtrated and concentrated. Under atmosphere of argon, the obtained residue (380 g) was added by acetone (3000 mL) and 2,2-dimethoxypropane (1800 mL), additionally added by boron trifuloride.diethylether complex (19.3 mL) and stirred for an hour and a half at room temperature. The mixture was concentrated and the residue was dissolved in ethyl acetate (1500 mL) and washed with saturated sodium hydrogen carbonate (100 mL), water (1000 mL) and saturated brine (1000 mL). The oragnic layer was dried over a sodium sulfate, filtrated and then concentrated to give the title compound (437 g) having the following physical data, which was used for the next reaction without purification.
NMR: δ 1.40–1.70, 3.76, 4.00–4.20, 4.37;
TLC: Rf 0.50 (ethyl acetate:hexane=1:4).

EXAMPLE 25 tert-butyl (4S)-4-[(1E,3S)-4-(4-fulorophenyl)-3-hydroxy-1-butene-1-yl]-2,2-dimethyl-1,3-oxazolidine-3-caboxylate Under atmosphere of argon, the compound prepared in Example 24 (387 g) was dissolved in toluene (4500 mL) and dropped by diisobutylaluminum hydride (1.01M in toluene, 2500 mL) at the temperature of −78° C. The mixture was stirred for an hour and a half additonally, diisobutylaluminum hydride discomposed with methanol (200 mL) and then the temperature was raised moderately. The mixutre was added by 2N hydrochloric acid (7000 mL) at a temperature of 0° C. and extracted by ethyl acetate (3000 mL). The organic layer was washed with water (2000 mL) and saturated brine (2000 mL), dried over a sodium sulfate, filtrated and then concentrated and the crude aldehyde compound (342 g). Under atmosphere of argon, sodium hydride (56.8 g) was dissolved in tetrahydrofuran (2400 mL) and dropped by a solution of dimethyl 3-(4-fulorophenyl)-2-oxopropylphosphonate (391 g) dissolved in tetrahydrofuran (3600 mL) at a temperature of 50° C. The suspension of obtained anion was stirred for an hour at the room temperature and then added by a solution the above-mentioned crude aldehyde dissolved in tetrahydrofuran (1000 mL). The mixture was stirred for 15 minutes at the room temperature additionally, added by saturated ammonium chloride solution (3000 mL) and extracted by ethyl acetate (3000 mL). The organic layer was washed with water (2000 mL) and saturated brine (2000 mL), dried over a sodium sulfate, filtrated and then concentrated. The obtained residue was purified by column chromatography on silica gel (ethyl acetate:hexane=from 1:5 to 1:2) to give the enone compound (240 mg). Under atmosphere of argon, borane-tetrahydrofuran complex (716 mL) and (R)-5,5-diphenyl-2-methyl-3,4-propano-1,3,2-oxazaborolidine (CBS) (102 mL) were dissolved in tetrahydrofuran (1750 mL) and a solution of the above-mentioned enone compound dissolved in tetrahydrofuran (1750 mL) dropped to the mixture keeping the temperature inside from 5 to 12° C. for three hours. The mixture was added by methanol (100 mL) to discompose the reagent, added by ethyl acetate (4000 mL), and washed with 1N hydrochloric acid (4000 mL), water (2000 mL) and saturated brine (2000 mL). The oraganic layer was dried over sodium sulfate, filtrate and then concentrated and the obtained residue filtrate on silica gel (ethyl acetate). The solvent was concentrated to give the title compound (365 g) having the following physical data.
NMR: δ 1.34–1.70, 2.80, 3.68, 4.02, 4.37, 5.67, 6.99, 7.18;
TLC: Rf 0.38 (ethyl acetate:hexane=1:3).

EXAMPLE 26

(2S,3E,5S)-2-amino-6-(4-fulorophenyl)-3-hexene-1,5-diol.chloride

The compound prepared in Example 25 (340 g) was dissolved in methanol (3000 mL) and added by 10% hydrochloric acid/methanol (3000 mL) below 20° C. The mixture was stirred for three hours and a half and concentrated. The obtained crystal was recrystallized by ethanol (300 mL)-ethyl acetate (1200 mL) to give the title compound (105 g) having the following physical data.
NMR(DMSO-d₆): δ 2.68, 3.40, 3.51, 3.65, 4.17, 5.04, 5.36, 5.54, 5.86, 7.07, 7.23, 7.97;
TLC: Rf 0.10 (methanol:chloroform=1:5).

EXAMPLE 27 ethyl 4-[(2-{(4S)-4-[(1E,3S)-4-(4-fulorophenyl)-3-hydroxy-1-butene-1-yl]-2-oxo-1,3-oxazolidine-3-yl}ethyl)thio]butanoate ethyl 4-[(2,2-diethoxyethyl)thio]butanoate (115 g) was dissolved in a mixed solution of acetonitrile (280 mL) and water (31.5 mL), added by the compound prepared in Example 26 (95 g) and p-toluenesulfonic acid monohydrate (11.7 g) successively and under atmosphere of argon, the mixture was stirred for an hour at the room temperature. Triacetoxy sodium boron hydride (138 g) was dissolved in acetonitrile (318.5 mL) and the mixture was dropped by the above-mentioned imine at 0° C. and stirred overnight. The mixture was added by ethyl acetate (2000 mL), washed with saturated sodium hydrogen carbonate solution (1000 mL), water (1000 mL) and saturated brine (1000 mL) and the organic layer was dried over sodium sulfate, filtrate and concentrated. The obtained residue was purified by short column on silica gel (from ethyl acetate only to methanol: methyl acetate=1:5) to give amine compound (100 g). This amine compound (100 g) and triethylamine (70 mL) was dissolved in tetrahydrofuran (1000 mL), added by triphosgene (24.8 g) at a temperature of 0° C. and under atmosphere of argon, the mixture was stirred for three hours. The mixture was added by ethyl acetate (2000 mL), washed with water (1000 mL) and saturated brine (1000 mL) and the organic layer was dried over sodium sulfate, filtrated, concentrated and purified by column on silica gel (ethyl acetate: hexane=from 1:1 to 2:1 to 4:1) to give the title compound (80 g) having the following physical data.

NMR: δ 1.26, 1.90, 2.01, 2.42, 2.61, 2.82, 3.07, 3.45, 3.91, 4.12, 4.34, 4.41, 5.58, 5.88, 7.02, 7.17;

TLC: Rf 0.40 (ethyl acetate:hexane=2:1).

EXAMPLE 28

4-[(2-{(4S)-4-[(1E,3S)-4-(4-fulorophenyl)-3-hydroxy-1-butene-1-yl]-2-oxo-1,3-oxazolidine-3-yl}ethyl)thio]butyric acid The compound prepared in Example 27 (80 g) was dissolved in a mixed solution of 1,2-dimethoxyethane (1000 mL) and ethanol (500 mL) and added by 2N sodium hydroxide solution (500 mL) at the 0° C. The mixture was stirred for four hours, added by 2N hydrochloric acid (500 mL) at the 0° C. and extracted by ethyl acetate (1000 mL). The organic layer was washed with water (1000 mL) and saturated brine (1000 mL), dried over sodium sulfate, filtrated, concentrated and the obtained residue was added by ethyl acetate (80 mL) and hexane (60 mL) and stirred heating for thirty minutes at 50° C. After bringing back to the room temperature, the mixture was filtrated to give the title compound (61 g) having the following physical data. White crystal; melting point from 75 to 76° C.;

NMR: δ 1.89, 2.58, 2.82, 3.08, 3.46, 3.90, 4.39, 5.56, 5.87, 7.01, 7.16;

MS(APCI, Neg. 20V):396 (M-H)$^-$;

TLC: Rf 0.49 (ethyl acetate).

Biological Examples

For examples, the pharmacological activities of the compounds of the invention were comfirmed in experiments performed in a laboratory using the cells which express prostanoid receptor sub-types. Whole operation which was based on the basic genetic engineering method included that the cells which highly express genes were prepared and the methods which are ordinary were applicated. Additionally, the measuring method of the invention is the method which had advancement of the measurement accuracy and/or improvement of the measurement sensitivity for evaluating the compounds of the invention as follows. The detailed experimental methods showed below.

(i) Experiment for Receptor-Binding Using Cells which Express Prostanoid Receptor Sub-Types According to the method of Sugimoto et al. (*J. Biol. Chem.*, 267, 6463–6466 (1922)), CHO cells which expressed prostanoid receptor sub-types (murine $EP_1$, $EP_2$, $EP_{3\alpha}$, and $EP_4$ respectively) were prepared and used as membrane authentic samples.

A reaction solution (200 µL) containing the prepared membrane fraction (0.5 mg/ml) and $^3H$-$PGE_2$ was incubated at room temperature for an hour. The reaction was terminated with ice cold buffer (3 mL), and the reaction mixture was suction filtrated under reduced pressure through a glass filter (GF/B), on which the binding $^3H$-$PGE_2$ was trapped, and the binding radioactivity was measured by means of a liquid scintillator.

The $K_d$ value was obtained from the Scatchard plots (*Ann. N.Y. Acad. Sci.*, 51, 660 (1949)). Non-specific binding was obtained as the binding in the presence of an excess amount (2.5 µM) of unlabelled $PGE_2$. Measurement of the binding inhibition for $^3H$-$PGE_2$ with the compounds of the invention was performed by adding $^3H$-$PGE_2$ (2.5 nM) and a series of concentrations of the compounds of the invention. In this reaction, the following buffer was used in all cases.

Buffer: 10 mM potassium phosphate (pH6.0), 1 mM EDTA, 10 mM $MgCl_2$ and 0.1M NaCl.

Dissociation constant $K_i$ (µM) of each compounds was calculated from the following equation.

$$K_i = IC_{50}/(1+([C]/K_d));$$

The binding activities of all the compounds of the invention to the $EP_4$ receptor are shown the $K_i$ value of below 1 µM. For example, the $K_i$ value of the compound of Example 5 was 6.4 nM.

(ii) Activity of $EP_4$ Receptor Agonist

Experiment for measurement of the activity of an $EP_4$ receptor agonist with the cells expressing prostanoid receptor sub-types.

According to the method of Nishigaki et al. (*FEBS Lett.*, 364, 339–341 (1995)), CHO cells which expressed mouse $EP_4$ receptor sub-types were prepared, inoculated on a 24-well microplate at $10^5$ cells/well, and incubated for 2 days for use in the experiment. Each well was washed with 500 µL of MEM (Minimum Essential Medium), added 450 µL of an assay medium (MEM containing 1 mmol/L of IBMX and 1% BSA), and incubated at 37° C. for 10 minutes. Then, 50 µL of a solution containing PGE2 alone or PGE2 and a test compound was added to start the reaction, which was conducted at 37° C. for 10 minutes and terminated with addition of 500 µL of ice-cold trichloroacetic acid (10% w/v). The reaction mixture was once treated by freezing (−80° C.) and thawing, and the cells were removed with a scraper and centrifuged at 13,000 rpm for 3 minutes to give a supernatant, of which the cAMP concentration was determined with a cAMP assay kit. That is, a buffer solution provided for the [$^{125}$I] cAMP assay kit (Amersham) was added to 125 µL of the above-mentioned supernatant to be 500 µL, which was mixed with 1 mL of 0.5 mol/L tri-n-octylamine/chloroform solution to eliminate trichloroaceteic acid contained in chloroform layer. The aqueous layer as a sample was measured to determine the cAMP amount contained in the sample according to the method as described in an instruction provided in the [$^{125}$I] cAMP assay kit.

The agonistic effect ($EC_{50}$ value) of the compounds of the invention was determined by calculating 50% producitivity of cAMP when the maximum effect of $PGE_2$ alone was regarded as 100%.

(iii) Inhibitory Effect for TNF-α Production

Using of male SD rats, LPS (10 µg/2 mL/kg) was administered intravenously through the tail of rats, and after a lapse of 90 minutes the blood was collected in a heparinized condition from the abdominal vena cava to prepare the plasma. The amount of TNF-α in the plasma was determined by an ELISA kit (Rat TNF-α Immunoassay kit; Biosource).

The compound of the invention was dissolved in an equimolar amount of 0.02 mol/L sodium hydroxide solution, diluted with distilled water, and orally administered 30 minutes before administration of LPS. The concentration at which the production of TNF-α was inhibited by 50% was regarded as the effective concentration ($IC_{50}$) when the concentration of plasma TNF-α in a control group (LPS treated but no compound administered) was 100%.

(iv) Inhibitory Effect for Chronic Articular Rheumatism (1) Collagen Induced Arthritis in Rats Experiment was performed according to the method of Osterman et al. (*Inflamm. Res.*, 44, 258–263). Inducing agents (an emulsion by adding an equal volume of physiological saline and 2 equivalent volume of incomplete Freund's adjuvant to 0.3% solution of type II collagen derived from bovine) 0.1 mL each were administered intracutaneously to the 4 sites of the back of a female DA/Slc rat. After a lapse of 1 week, the same inducing agents were further administered intracutaneously to the tail root to induce arthritis. At 27th day, the four limbs were respectively scored responding to the degree of erythema and swelling and assessed as 30 was regarded as full scores. The compound of invention was dissolved in an equimolar amount of 0.02 mol/L sodium hydroxide solution, diluted with distilled water, and orally administered 3 times a day from the next day of the first administration of inducing agents.

(2) Cocktail Antibodies Induced Arthritis in Mice

Cocktail of antibodies to type II collagen was intravenously administered to male DBA/1JNCrj mice at a dose of 2 mg/0.5 ml/mouse. After a lapse of 3 days, lipopolysaccharide was intraperitoneally administered at a dose of 25 μg/0.1 mL/mouse to induce arthritis. At 10th day, the four limbs were respectively scored responding to the degree of erythema and swelling and assessed as 4 was regarded as full scores. The compound of the invention was dissolved in an equimolar amount of 0.02 mol/L sodium hydroxide solution, diluted with distilled water, and orally administered 3 times a day from 30 minutes before the administration of lipopolysaccharide.

(v) Effect on the Promotion of Osteogenesis I

Female SD rats (11 weeks of age; average weight 271 g) were employed in 5 rats for each group. Rat was cut open at the lateral abdomen under anesthesia with pentobarbital to remove the ovary and then sutured. In a sham group, incision and suture were made but no removal of the ovary was made.

From 6 days after the surgical operation, the compounds of the invention (dissolved in an equimolar amount of 0.02 mol/L sodium hydroxide solution, and diluted with distilled water) were orally administered 3 times a day for 2 months. To the control group and the sham group, physiological saline was administered. After termination of the test, the animals of each group were killed and subjected to autopsy. The bone density of trabecular bone region of left femur was measured by means of an apparatus for measuring the bone density of peripheral bone (XCTμ-960A, Norland/Stratech).

(vi) Effect on the Promotion of Osteogenesis 2

Using beagle/CSK canines of approximately 6 months of age, the effect on the promotion of osteogenesis can be examined.

The compound of the invention was dissolved in physiological saline and orally administered over 4 weeks. To the control group an equal volume of physiological saline was administered. After termination of administration, the canines of each group were killed, subjected to autopsy, and the bone area and bone density were measured.

(1) Measurement of Bone Area

The removed femur was fixed with 10% buffered formalin solution and cut in round slices perpendicularly to the bone axis in 10 mm width at the center position of 25 mm from trochlear fossa; the surface near the epiphysis was photographed with a camera at a certain distance, and the picture was sent into a computer to measure the bone area by image analysis.

(2) Measurement of Bone Density

The sample of 1 cm width used in (1) was taken radiography in side view, and the image was sent into a computer to measure the radiation amount per unit area in the area of a certain width to obtain the bone density (Micro Focus X-Ray Enlargement Camera System μFX-1000 (Fujifilm)).

(vii) Effect of Accelerating Bone Fracture Healing 1

This experiment can be achieved to the method of Markel et al. (*J. Bone and Joint Surgery*, 73A, 914–923, 1991). Using beagle/CSK canines of approximately 6 months of age, the femoral tibia is fractured under anesthesia and taken radiography periodically for 3 months to assess the progress of healing. Thus, the effect of accelerating bone fracture healing can be easily judged. The compound of the invention was orally administered every day. Distilled water was administered as control group. When the effect of accelerating bone fracture healing was confirmed, the femoral tibia was removed. Additionally the above-mentioned effect was quantitatively assessed by measuring bone density and bone strength of the removed femoral tibiae.

(viii) Inhibitory Effect for Gastric Urea

Indomethacin was orally administered to SD rats at a dose of 20 mg/kg to induce gastric ulcer. After a lapse of 6 hours, the stomach was removed to measure the ulcerous area of mucosa. The compound of the invention was orally administered 30 minutes before administration of indomethacin.

(ix) Effect of Accelerating Bone Fracture Healing 2

According to the methods of R. Sakai (*Bone*, 25, 191–196 (1999)), H. Kawaguchi (*Endocrinology*, 135, 774–781 (1994)) and T. Hoshino (*J. Biomed. Mater. Res.*, 51, 229–306 (2000)), a bone fracture model was prepared using male IGS rats of 8 weeks of age. Hair of the left hind-limb of a rat was cut under anesthesia with pentobarbital Na, and Viccillin S 500 (500 mg potency) (Meiji Seika) was intramuscularly injected at a dose of 10 mg potency/100 μL distilled water/body. Then the skin on the fibula (from the back of knee joint to Achilles' tendon) was incised to ablate the muscular tissue and the fibula was exposed. The fibula was cut off with sharp scissors approximately at the central position to make a fracture site, which was then restored to its former position, and the incised site was closed by suture with disinfection by iodine tincture/disinfectant ethanol. After making the fracture site and before closing the wound operation, a physiological saline solution containing 0.2% Tween 80 microsphere (containing 0.3 mg/kg as an active drug; about 60 μL) prepared in Formulation Example 3(1) was added only once. In addition, the Compound (1) as a control for comparison was infused continuously for 2 hours twice a day through a catheter attached to the carotid artery. This was made until the last day of the experiment. At the 21st day of the experiment, the rats were subjected to euthanasia with $CO_2$ gas, and the connective tissue of the hind-limbs, including muscle, etc., was eliminated to obtain both of the fibulae. The recovered fibulae were taken radiographs to assess development of the fracture healing based on the presence of fracture line and callus formation, etc., and the bone density and bone strength around the fracture site were measured.

(1) Measurement of the Bone Density of the Callus Region Using a Micro Focus X-Ray Enlargement Camera System The bone density of the callus region at the fracture site of the recovered fibula was measured referring to the reports of C. Matsumoto (*Calcif Tissue Int.*, 55, 324–329 (1999)), Kaoru Yamazaki (*Nihon Rinsyo*, 56, 1464–1468 (1998)), and Keiichi Nakagawa (*Sentan Iryo*, 4(6), (1996)). Radiophotographs were taken at 4 magnifications using a micro focus X-ray enlargement camera system (FUJIFILM)/imaging plate (BAS-IP MS 2025; FUJIFILM)) in a radiation condition of 40 kV tube voltage, 100 μA tube current, and radiation time 5 seconds. During photographing, a phantom for quantitative analysis of bone salt for mice (Kyoto Kagaku Co.) was set together in order to make a standard curve for measurement of bone density. The image was read by a Bio-imaging Analyzer BAS-1800 (FUJIFILM)/Image reader (FUJIFILM) and processed with an Image Gauge, ver. 3.1.12 (FUJIFILM). Based on the fracture line (surface) as a callus region, the region of interest (hereinafter sometimes referred to as ROI) was set at the position of 3 mm in the remote direction (ankle) and the proximal direction (knee) respectively to calculate the bone density of each ROI from the standard curve obtained from the phantom for quantitative analysis of bone salt. The bone density of the callus region at the fracture side was calculated from the following equation and represented by mean±standard error (mg/cm²).

> Bone density in callus region={([bone density in proximal callus region]×A)+([bone density in remote callus region]×B)}/(A+B)

A represents the ROI area in the proximal callus region;
B represents the ROI area in the remote callus region.

(2) Measurement of the Bone Strength by a Bending Test at Three Points

According to the report of T. Hoshino (*J. Biomed. Mater. Res.*, 51, 229–306 (2000)), a bending test at three points was performed. Using an Instron Universal Material Testing Machine Type 5544 (Instron Japan)/Merlin (Instron Japan; version 22043), breaking strength and energy absorption were measured in a condition of 2.5 mm/sec of bending rate and 10 mm of sample holder width. The bone strength data were calculated as relative strength of the non-fractured side versus the fractured side for the respective individuals and represented by means±standard error (% of intact).

(x) Inhibitory Effect on Ulcerous Colitis

7% Sodium dextran sulfate (hereinafter abbreviated to as DSS) was given freely to male C57BL/6 mice. From the beginning of drinking, the body weight and clinical score were recorded every other day. The clinical score was calculated as the sum of diarrhea score (normal: 0, soft feces: 2, diarrhea: 4) and hematochezia (normal: 0, bleeding: 2, heavy bleeding: 4). At 10 days after taking of the SDS aqueous solution, the blood was collected from the vena cava under ethereal anesthesia in the presence of heparin, and the hematocrit value was measured by a hemocytometer. During a period of from 0 day to 10th day after taking of the SDS aqueous solution, the compound of the invention was orally administered twice a day at a dose of 10, 30, 100 or 300 μg/10 mL/kg.

FORMULATION EXAMPLE 1

The following components were admixed in conventional method and punched out to obtain 10000 tablets each containing 0.5 mg of active ingredient.

(15α,13E)-9-oxo-15-hydroxy-16-(3-phenylphenyl)-17,18,19,20-tetranol-5-thia-8-aza-10-oxaprost-13-enoic acid 5.0 g Carboxymethylcellulose calcium 20 g Magnesium stearate 10 g Micro crystalline cellulose 920 g

FORMULATION EXAMPLE 2

The following components were admixed in conventional method, and the solution 1 mL each was filled into a vial, the vials was freeze-dried in conventional method to obtain 10000 vials each containing 0.2 mg of active ingredient.

(15α,13E)-9-oxo-15-hydroxy-16-(3-phenylphenyl)-17,18,19,20-tetranol-5-thia-8-aza-10-oxaprost-13-enoic acid 2.0 g Mannit 500 g Distilled water 10 L

The invention claimed is:

1. A compound represented by formula (I)

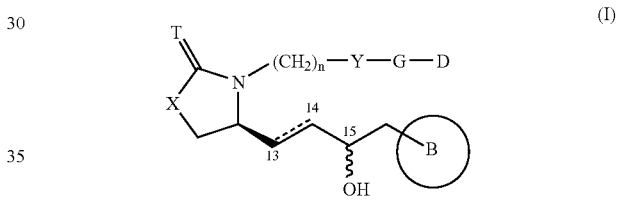

wherein ⌇ is a single bond or a double bond,
⌇ is α-configuration, β-configuration or a voluntary mixture of α-configuration and β-configuration,
D is —COOR¹,
R¹ is hydrogen or C1–4 alkyl,
G is ringA,
ringA is

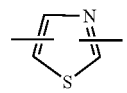

Y is —S—,
T is oxygen or sulfur,
X is —CH₂—,
ringB is,

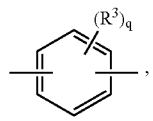

wherein R³ is (1) a halogen atom, (2) C1–4 alkyl optionally substituted with 1–5 of halogen atom(s), (3) C1–4 alkoxy optionally substituted with 1–5 of halogen atom (s), (4) C1–4 alkyl substituted with C1–4 alkoxy, (5) phenyl or (6) 3- to 15-membered mono-, bi- or tri-heterocyclic aryl containing 1 to 4 hetero atom(s) selected from the group consisting of oxygen, nitrogen and sulfur atom(s) which may be partially or fully saturated, and (5) phenyl or (6) heterocyclic aryl in $R^3$ is optionally substituted with 1–3 of (a) halogen atom (s), (b) C1–4 alkyl, (c) C1–4 alkoxy and/or (d) nitro, q is 0 or an integer of 1–5, when q is 2 or more, plural $R^3$'s are the same or different, and n is an integer of 1–4, a salt thereof, a solvate thereof, a cyclodextrin clathrate thereof, or a prodrug thereof.

2. The compound according to claim 1, which is represented by formula (I-1):

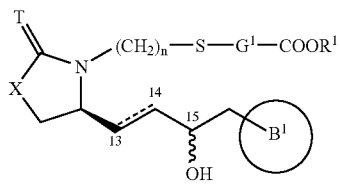

(I-1)

wherein $G^1$ is ringA$^1$, ringA$^1$ is

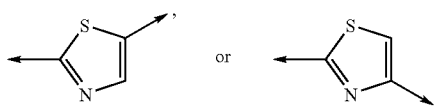

wherein left-pointing arrow represents binding to S, and right-pointing arrow represents binding to COOR$^1$, ringB$^1$ is,

ringB$^1$ may be substituted with a halogen atom, C1–4 alkyl, phenyl, methoxymethyl, trifluoromethyl and/or trifluoromethoxy, other symbols have the same meanings as described in claim 1, and wherein when T is oxygen, X is —CH$_2$—, and when n is an integer of 2–4, $G^1$ is ringA$^1$.

3. The compound according to claim 2, which is selected from the group consisting of:

(28) (15α,13E)-9-oxo-15-hydroxy-16-(4-fluoro-3-phenylphenyl)-5-(4-carboxythiazol-2-yl)-1,2,3,4,17,18,19,20-octanol-5-thia-8-azaprost-13-ene,

(29) (15α,13E)-9-oxo-15-hydroxy-16-(3-ethylphenyl)-5-(4-carboxythiazol-2-yl)-1,2,3,4,17,18,19,20-octanol-5-thia-8-azaprost-13-ene,

(31) (15α,13E)-9-oxo-15-hydroxy-16-(3-trifluoromethoxyphenyl)-5-(4-carboxythiazol-2-yl)-1,2,3,4,17,18, 19,20-octanol-5-thia-8-azaprost-13-ene,

(32) (15α,13E)-9-oxo-15-hydroxy-16-(3-chloro-4-fluorophenyl)-5-(4-carboxythiazol-2-yl)-1,2,3,4,17,18,19,20-octanol-5-thia-8-azaprost-13-ene,

(35) (15α,13E)-9-oxo-15-hydroxy-16-(4-fluorophenyl)-5-(5-carboxythiazol-2-yl)-1,2,3,4,17,18,19,20-octanol-5-thia-8-azaprost-13-ene, and

(37) (15α,13E)-9-oxo-15-hydroxy-16-(4-chlorophenyl)-5-(4-carboxythiazol-2-yl)-1,2,3,4,17,18,19,20-octanol-5-thia-8-azaprost-13-ene.

4. The compound according to claim 1, which is represented by formula (I-2):

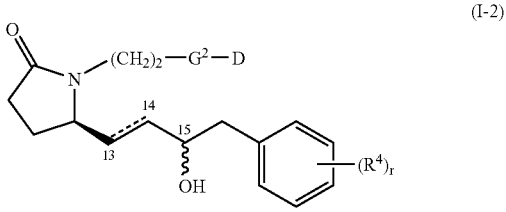

(I-2)

wherein $G^2$ is

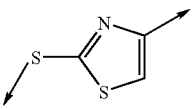

wherein left-pointing arrow represents binding to —(CH$_2$)$_2$—, and right-pointing arrow represents binding to D, $R^4$ is (1) a halogen atom, (2) C1–4 alkyl, (3) C1–4 alkoxy, (4) C1–4 alkyl optionally substituted with 1–5 of halogen atom(s), (5) C1–4 alkoxy optionally substituted with 1–5 of halogen atom(s), (6) phenyl or (7) 3- to 15-membered mono-, bi- or tri-heterocyclic aryl containing 1 to 4 hetero atom(s) selected from the group consisting of oxygen, nitrogen and sulfur atom(s) which may be partially or fully saturated, and (6) phenyl or (7) heterocyclic in the $R^4$ may be substituted with 1–3 of (a) a halogen atom(s), (b) C1–4 alkyl, (c) C1–4 alkoxy and/or (d) nitro, r is an integer 1 to 5, and other symbols have the same meanings as described in claim 1.

5. The compound according to claim 4, which is selected from the group consisting of:

(4) (15α,13E)-9-oxo-15-hydroxy-16-(3-(5-methylbenzothiazol-2-yl)phenyl)-5-(4-carboxythiazol-2-yl)-1,2,3,4, 17,18,19,20-octanol-5-thia-8-azaprost-13-ene, (6) (15α,13E)-9-oxo-15-hydroxy-16-(3-(6-methylbenzoxazol-2-yl)phenyl)-5-(4-carboxythiazol-2-yl)-1,2,3,4,17, 18,19,20-octanol-5-thia-8-azaprost-13-ene, (9) (15α,13E)-9-oxo-15-hydroxy-16-(3-(4-methylbenzothiazol-2-yl)phenyl)-5-(4-carboxythiazol-2-yl)-1,2,3,4, 17,18,19,20-octanol-5-thia-8-azaprost-13-ene,

(12) (15α,13E)-9-oxo-15-hydroxy-16-(3-(5,7-dimethylbenzoxazol-2-yl)phenyl)-5-(4-carboxythiazol-2-yl)-1,2,3,4, 17,18,19,20-octanol-5-thia-8-azaprost-13-ene,

(13) (15α,13E)-9-oxo-15-hydroxy-16-(3-(5-chlorobenzothiazol-2-yl)phenyl)-5-(4-carboxythiazol-2-yl)-1,2,3,4, 17,18,19,20-octanol-5-thia-8-azaprost-13-ene,

(15) (15α)-9-oxo-15-hydroxy-16-(3-(2,4-dimethylphenyl)phenyl)-5-(4-carboxythiazol-2-yl)-1,2,3,4,17,18,19,20-octanol-5-thia-8-azaprost-13-ene,

(16) (15α,13E)-9-oxo-15-hydroxy-16-(3-(3,4-dimethylphenyl)phenyl)-5-(4-carboxythiazol-2-yl)-1,2,3,4,17,18,19,20-octanol-5-thia-8-azaprost-13-ene, and

(19) (15α,13E)-9-oxo-15-hydroxy-16-(3-(5-chlorobenzoxazol-2-yl)phenyl)-5-(4-carboxythiazol-2-yl)-1,2,3,4,17,18,19,20-octanol-5-thia-8-azaprost-13-ene.

6. A pharmaceutical composition comprising the compound represented by formula (I) according to claim 1, a salt thereof, a solvate thereof, a cyclodextrin clathlate thereof, or a prodrug thereof, and a pharmaceutically acceptable carrier.

7. The compound according to claim 1, wherein n is 1 or 2.

* * * * *